United States Patent [19]
Kozikowski et al.

[11] Patent Number: 6,150,376
[45] Date of Patent: *Nov. 21, 2000

[54] BI- AND TRI-CYCLIC AZA COMPOUNDS AND THEIR USES

[75] Inventors: Alan P. Kozikowski, Princeton, N.J.; Miles P. Smith, Arlington, Va.

[73] Assignee: Georgetown University, Washington, D.C.

[*] Notice: Under 35 U.S.C. 154(b), the term of this patent shall be extended for 00 days.

[21] Appl. No.: 09/130,178

[22] Filed: Aug. 5, 1998

[51] Int. Cl.[7] .......................... A61K 31/44; C07D 221/02
[52] U.S. Cl. ........................... 514/299; 546/112; 546/183
[58] Field of Search .................................... 546/112, 183; 514/299

[56] References Cited

U.S. PATENT DOCUMENTS 5,998,405  12/1999  Scheel-Kruger et al. ............... 514/214

FOREIGN PATENT DOCUMENTS

WO 97/16451  5/1997  WIPO .

OTHER PUBLICATIONS

Abraham et al., 1992, "N–Modified Analogues of Cocaine: Synthesis and Inhibition of Binding to the Cocaine Receptor," *J. Med. Chem.* 35:141–144.

Kozikowski et al., 1994, "Structure–Activity Relationship Studies of N–Sulfonyl Analogs of Cocaine: Role of Ionic Interaction in Cocaine Binding," *J. Med. Chem.* 37:3440–3442.

Madras et al., 1996, "Nitrogen–Based Drugs Are Not Essential for Blockade of Monoamine Transporters," *Synapse* 24:340–348.

Smith et al., 1998, "The Synthesis of Tricyclic Cocaine Analogs via the 1,3–Dipolar Cycloaddition of Oxidopyridinium Betaines," *Tetrahedron Letters* 39:197–200.

Stoelwinder et al., 1994, "Differential Binding and Dopamine Uptake Activity of Cocaine Analogues Modified at Nitrogen," *Bioorganic & Medicinal Chemistry Letters* 4:303–308.

Thakore et al., 1996, "Treating depression with specific serotonergic acting agents," *Journal of Serotonin Research* 3:145–160.

*Primary Examiner*—Mukund J. Shah
*Assistant Examiner*—Bruck Kifle
*Attorney, Agent, or Firm*—Pennie & Edmonds LLP

[57] ABSTRACT

The present invention provides tropane-derived monoamine neurotransmitter re-uptake inhibitors which predictably exhibit selectivity for either the serotonin or dopamine transporter, pharmaceutical compositions thereof and methods for their use. The serotonin-selective re-uptake inhibitors are particularly useful for treating neurological disorders associated with the serotonergic neural system of the brain, such as depression, with significantly reduced side-effects. The dopamine-selective re-uptake inhibitors are particularly useful for treating disorders associated with dopamine re-uptake and/or acetylcholine release.

30 Claims, 3 Drawing Sheets

BI- AND TRI-CYCLIC AZA COMPOUNDS AND THEIR USES

This invention was made in part under National Institutes of Health, National Institute on Drug Abuse, Grant Nos. DA 10458 and DA 05867. The U.S. Government has certain rights in this invention.

FIELD OF THE INVENTION

The present invention relates to novel bi- and tri-cyclic aza compounds which are monoamine neurotransmitter (i.e., dopamine, serotonin and norepinephrine) re-uptake inhibitors. In particular, the invention relates to bi- and tri-cyclic aza compounds derived from tropanes which are potent and selective inhibitors of serotonin and/or dopamine re-uptake, and which are therefore useful in the treatment of disorders or diseases responsive to the inhibition of serotonin and/or dopamine re-uptake, such as depression and related disorders, panic disorders, memory deficits, attention deficit hyperactivity disorder, obesity, anxiety, cocaine and other drug addition or misuse, obsessive-compulsive disorder, and bulimic and other eating disorders.

BACKGROUND OF THE INVENTION

The brain consists of a plurality of neurons that communicate with each other via chemical messengers. Each neuron generates neurochemicals, called neurotransmitters, which act at receptors on the cellular membranes of neurons.

One group of neurotransmitters, the monoamine neurotransmitters, includes dopamine (DA), serotonin (5-HT) and norepinephrine (NE).

These monoamine neurotransmitters are released into the synaptic cleft in order to stimulate post-synaptic receptor activity. Removal or inactivation of monoamine neurotransmitters occurs mainly by a re-uptake mechanism into presynaptic terminals, which terminates monoaminergic transmission. Blocking or inhibiting the re-uptake increases the synaptic availability of the neurotransmitters, thereby potentiating the signal (Kitama et al., 1996, Jpn. J. Pharmacol. 72:195–208).

Inhibition of monoamine neurotransmitter re-uptake has been exploited to develop treatments for a large number of neurological disorders. For example, the selective dopamine transporter (DAT) antagonist benztropine is used clinically for the treatment of Parkinson's disease (Agoston et al., 1994, J. Med. Chem. 40:4329–4339) and methylphenidate (Ritalin®; CebaGeneva) is used to treat attention deficit hyperactivity disorder (Klein, 1995, Arch. Gen. Psychiatry 52:429–433).

Norepinephrine transporter (NET) re-uptake inhibitors such as desipramine, nortriptyline and protriptyline, and the mixed serotonin and norepinephrine re-uptake inhibitors imipramine and amitriptyline exhibit effective antidepressant activity (Thomas et al., 1987 Psychopharmacol. 93:193–200). However, they also exhibit a high incidence of adverse side effects (Blackwell, 1981, Drugs 21:201–219).

Serotonin-selective re-uptake inhibitors are thought to exhibit fewer side effects than the other classes of monoamine re-uptake inhibitors. The selective serotonin transporter (5-HTT) antagonists fluoxetine (Prozac®; Dista) and paroxetine (Paxil®) are used for the treatment of depression and related psychological disorders with significantly fewer side effects than other treatments (Wong et al., 1995, Life Sci. 57:411–441; Dechant et al., 1991, Drugs 41:225–253; Möller et al., 1996, Drugs 52:625–638). Other serotonin selective re-uptake inhibitors currently used to treat depression include citalopram, fluvoxamine, sertraline, nefazadone and tianeptine (Thakore et al., 1996, J. Serotonin Res. 3:145–160). These serotonin-selective re-uptake inhibitors also exhibit fewer side effects than the classical tricyclic antidepressants which are norepinephrine re-uptake inhibitors (see, Möller et al., supra). Venlafaxine, which is a dual serotonin and norepinephrine re-uptake inhibitor (with a five-fold selectivity for serotonin) also exhibits a side effect profile that is similar to the other serotonin-selective re-uptake inhibitors.

However, while the serotonin-selective re-uptake inhibitors induce fewer adverse side effects than the other classes of monoamine neurotransmitter inhibitors, they still cause sleep and gastrointestinal disturbances, as well as sexual dysfunction. Thus, new classes of clinically useful serotonin-selective re-uptake inhibitors which reduce these and other side effects would be highly desirable.

Serotonin-selective re-uptake inhibitors inhibit the serotonin transporter within minutes; however, with the exception of venlafaxine (4–7 days; Preskorn, 1994, J. Clinical Psychiatry 55 (Suppl. A):6–22) and citalopram, their full antidepressant effect is observed only after three to four weeks of treatment, indicating that re-uptake inhibition per se is not necessarily fully responsible for their anti-depressant response. Rather, further activities probably underlie their therapeutic effect. This delayed onset of anti-depressant effect is considered to be a serious drawback to current serotonin-selective re-uptake inhibitor therapeutics. As inhibition of dopamine re-uptake has been implicated in providing a more rapid onset of anti-depressant effect, development of new classes of serotonin-specific re-uptake inhibitors which also exhibit low to moderate dopamine re-uptake inhibition would be highly desirable.

Cocaine, one of the most commonly abused addictive drugs in America, also potently inhibits all three monoamine transporters. A growing body of evidence points to the ability of cocaine to bind to the DAT and to inhibit re-uptake of dopamine as being responsible for the reinforcing properties of this drug (Volkow et al., 1997, Nature 6627:830–833). However, evidence suggest 5-HTT inhibition also plays a modulatory role in cocaine's reinforcing properties (Walsh et al., 1997, Psychopharmacol. 130:41–58). A number of highly potent cocaine analogs which exhibit varying degrees of selectivity for the monoamine transporters, and information concerning their structure-activity relationships, have been reported (Clarke et al., 1973, J. Med. Chem. 16:1260–1267; Abraham et al., 1992, J. Med. Chem. 35:141–144; Kozikowski et al., 1994, J. Med. Chem. 37:3440–3442; Stoelwinder et al., 1994, Biorg. Med. Chem. Lett. 4(2):303–308). While the precise details of the binding interactions between these compounds and the various transporters are not well understood (Carroll et al., 1991, J. Med. Chem. 34:2713–2725; Carroll et al., 1993, In: Drug Design For Neuroscience, Kozikowski, Ed., Raven Press: New York, pp. 149–166), except for a small number of recently reported compounds (see, Madras et al., 1996, Synapse 24:340–348), all contain the common structural features of a phenyl group and a basic amine.

Despite these common features and the existence of a proposed pharmacophore model (Froimowitz, 1993, J. Comput. Chem. 14:934–943), little is known about the structural requirements underlying monoamine transporter selectivity. Given the different therapeutic effects exhibited by the various classes of selective monoamine transporter antagonists, the ability to develop new classes of monoamine re-uptake inhibitors showing varying degrees of specificity for the three monoamine transporters would be highly desirable. In particular, the ability to design and synthesize monoamine transporter agonists with specified selectivities for certain of the transporters would allow the development of new classes of therapeutics specifically tailored to treat disorders associated with certain of the transporters, while at the same time minimizing any undesirable side effects. Accordingly, these are objects of the present invention.

SUMMARY OF THE INVENTION

These and other objects are furnished by the present invention, which in one aspect provides novel bi- and tri-cyclic aza tropane analogs which inhibit monoamine neurotransmitter re-uptake. By constraining the conformation of the nitrogen lone pair electrons by way of a tether in a specified manner, the selectivity for the various monoamine transporters can be "tuned," thereby permitting the synthesis of compounds which specifically antagonize certain monoamine transporters, and thus re-uptake of specified monoamine neurotransmitters.

In one embodiment of the invention, the compounds are bi- or tri-cyclic tropane-derived aza compounds in which the nitrogen lone pair is constrained over the 2-carbon (ethano) bridge of the tropane moiety, and which have the structural formula (I):

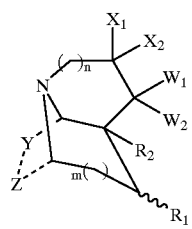

(I)

wherein:

n is 0, 1, 2 or 3;

m is 0, 1 or 2;

$X_1$, $X_2$, $W_1$ and $W_2$ taken together are $(C_5-C_{20})$ aryleno or 5–20 membered heteroaryleno, or $X_1$ and $W_1$ are each —H and $X_2$ and $W_2$ taken together form $(C_3-C_8)$ alkeno, or $X_1$ and $X_2$ are each —H and $W_1$ and $W_2$ taken together form =O, =S, =NOR$_3$, =N—CN, =N—NR$_3$R$_4$, =CR$_3$R$_4$ or $(C_3-C_8)$ alkeno, or $X_1$ and $X_2$ are each —H and $W_1$ and $W_2$ are each independently selected from the group consisting of —H, halogen, —OR$_3$, —SR$_3$, —N—NR$_3$R$_4$ or —(CH$_2$)$_o$—O—(CH$_2$)$_o$—R$_7$ where each o is independently 0, 1, 2 or 3;

Y and Z are each —H, or taken together form —(CHR$_5$)$_p$— where p is 1, 2 or 3;

R$_1$ is selected from the group consisting of $(C_5-C_{20})$ aryl, $(C_5-C_{20})$ aryl independently substituted with one or more R$_6$, 5–20 membered heteroaryl, 5–20 membered heteroaryl independently substituted with one or more R$_6$, $(C_6-C_{26})$ arylalkyl, $(C_6-C_{26})$ arylalkyl independently substituted with one or more R$_6$, 6–26 membered heteroarylalkyl and 6–26 membered heteroarylalkyl independently substituted with one or more R$_6$;

R$_2$ is —H, $(C_1-C_6)$ alkyl, $(C_2-C_6)$ alkenyl, $(C_2-C_6)$ alkynyl, $(C_5-C_{20})$ aryl, 5–20 membered heteroaryl or —(CH$_2$)$_q$—O—(CH$_2$)$_q$—R$_7$ where each q is independently 0, 1, 2 or 3;

R$_3$ and R$_4$ are each independently selected from the group consisting of —H, $(C_1-C_6)$ alkyl, $(C_2-C_6)$ alkenyl, $(C_2-C_6)$ alkynyl, $(C_5-C_{20})$ aryl, $(C_5-C_{20})$ aryl independently substituted with one or more R$_6$, 6–26 membered heteroaryl and 6–26 membered heteroaryl independently substituted with one or more R$_6$;

each R$_5$ is independently selected from the group consisting of —H, halogen, $(C_1-C_6)$ alkyl and $(C_1-C_6)$ alkyl independently substituted with one or more halogens, hydroxy or $(C_1-C_6)$ alkoxy groups;

each R$_6$ is independently selected from the group consisting of halogen, —CF$_3$, —CN, $(C_1-C_6)$ alkyl, $(C_1-C_6)$ alkenyl, $(C_1-C_6)$ alkynyl, $(C_1-C_6)$ alkoxy and $(C_3-C_6)$ cycloalkoxy; and R$_7$ is $(C_5-C_{20})$ aryl, $(C_5-C_{20})$ aryl independently substituted with one or more R$_6$, 5–20 membered heteroaryl and 5–20 membered heteroaryl independently substituted with one or more R$_6$.

In another embodiment of the invention, the compounds are tri-cyclic tropane-derived aza compounds in which the nitrogen lone pair is constrained over the 3-carbon (propano) bridge of the tropane moiety, and which have the structural formula (II) or (III):

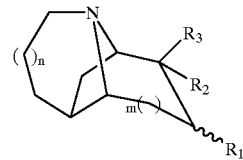

(II)

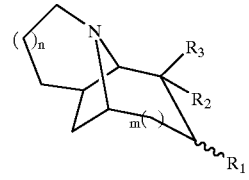

(III)

wherein n, m, R$_1$, R$_2$ and R$_3$ are as previously defined for structural formula (I).

While the compounds of formulae (I), (II) and (III) are potent inhibitors of monoamine neurotransmitter re-uptake generally, they exhibit striking differences in their selectivity. Presumably due to differences in their geometries of nitrogen lone pairs, aza compounds according to structural formulae (II) and (III) exhibit a preference for the dopamine transporter, while aza compounds according to structural formula (I) exhibit a striking preference for the serotonin transporter. Thus, while the compounds of the invention can be used to inhibit monoamine neurotransmitter re-uptake generally as a therapeutic approach towards the treatment of diseases and disorders related to this phenomenon, due to their predictable selectivity for certain monoamine transporters, the compounds of the invention provide, for the first time, the ability to tailor treatment regimens according to the transporter selectivity underlying the particular disorder's mechanism of action, as well as to design PET and SPECT imaging agents for use in diagnosing neurodegenerative disorders.

In another aspect, the present invention provides pharmaceutical compositions comprising one or more active compounds according to the invention and a pharmaceutically acceptable carrier, excipient or diluent. Such a preparation can be administered in the methods of the invention.

In still another aspect, the invention provides methods for the treatment of a variety of disorders and diseases associated with monoamine neurotransmitter re-uptake in animals, including humans. The method involves administering to a subject in need thereof an amount of at least one compound according to the invention, or a pharmaceutical composition thereof, effective to treat the disorder or disease. Disorders and diseases associated with monoamine neurotransmitter re-uptake, and which therefore can be treated with the compounds or compositions of the invention, include depression and related disorders, panic disorders, memory deficits, attention deficit hyperactivity disorder, obesity, anxiety, cocaine and other drug addiction or misuse, obsessive-compulsive disorder and bulimic and other eating disorders.

Because the compounds of the invention exhibit transporter selectivity, they are particularly useful for treating transporter-specific disorders. For example, due to their selectivity for the serotonin transporter, the aza compounds according to structural formula (I) are particularly effective for the treatment of disorders involving the serotonergic neural system of the brain, such as eating disorders, depression, obsessive-compulsive disorder, panic disorders, alcoholism, pain, memory deficits and anxiety, and disorders linked to decreased transmission of serotonin in mammals, including Ganser's syndrome, migraine headache, bulimia, obesity, pre-menstrual syndrome or late luteal phase syndrome, alcoholism, tobacco abuse, panic disorder, depression, anxiety, post-traumatic syndrome, memory loss, dementia of aging, social phobia, attention deficit hyperactivity disorder, chronic fatigue syndrome, premature ejaculation, erectile difficult, anorexia nervosa, disorders of sleep, autism, mutism and trichotillomania. These compounds have the added advantage of treating the above-described disorders with fewer adverse side-effects than currently available non-selective therapies.

Due to their selectivity for the dopamine transporter, the aza compounds according to structural formulae (II) and (III) are particularly effective for the treatment of disorders involving dopamine re-uptake activity, including Parkinsonism, depression, obesity, narcolepsy, cocaine and other drug addiction or misuse, attention deficit hyperactivity disorders and senile dementia, and disorders involving the release of acetylcholine, including memory deficits (e.g., in Alzheimer's disease and presenile dementia) and chronic fatigue syndrome.

Compounds of the invention according to structural formulae (I), (II) or (III) which exhibit appreciable inhibition of norepinephrine re-uptake are particularly useful for treating depression and for enhancing alertness, attention, arousal and vigilance.

Definitions

As used herein, the following terms shall have the following meanings:

"Alkyl:" refers to a saturated branched, straight chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In preferred embodiments, the alkyl groups are $(C_1-C_6)$ alkyl, with $(C_1-C_3)$ being particularly preferred.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, butenyl, isobutenyl, methallyl, cyclobutenyl, pentenyl, isopentenyl, cyclopentenyl, hexenyl, cyclohexenyl and the like. In preferred embodiments, the alkenyl group is $(C_2-C_6)$ alkenyl, with $(C_2-C_3)$ being particularly preferred.

"Alkynyl:" refers to an unsaturated branched, straight chain or cyclic hydrocarbon radical having at least one carbon-carbon triple bond. Typical alkynyl groups include, but are not limited to, ethynyl, propynyl, butynyl, pentynyl, hexynyl and the like. In preferred embodiments, the alkynyl group is $(C_2-C_6)$ alkynyl, with $(C_2-C_3)$ being particularly preferred.

"Alkeno:" refers to a saturated or unsaturated cyclic or acyclic hydrocarbon bridge. Typical alkeno groups include, but are not limited to, methano, ethano, propano, butano, etheno, prop[1]eno, but[1]eno, but[2]eno, buta[1,3]dieno, ethyno, prop[1]yno, but[1]yno, but[2]yno, buta[1,2]diyno, and the like. The attachement of the alkeno group may be either geminal or vicinal. Preferably, the alkeno group is a $(C_3-C_8)$ alkeno.

"Alkoxy:" refers to a radical of the formula —OR, where R is alkyl, alkenyl or alkynyl as defined herein.

"Aryloxy:" refers to a radical of the formula —OR', where R' is aryl as defined herein.

"Heteroaryloxy:" refers to a radical of the formula —OR", where R" is heteroaryl as defined herein.

"Substituted Alkyl, Alkenyl or Alkynyl:" refers to an alkyl, alkenyl or alkynyl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

"Aryl:" refers to an unsaturated cyclic or polycyclic hydrocarbon radical having a conjugated π electron system. Typical aryl groups include, but are not limited to, penta-2,4-diene, phenyl, naphthyl, acenaphthyl, anthracyl, azulenyl, chrysenyl, indacenyl, indenyl, perylenyl, phenanthrenyl, picenyl, pyrenyl, pyranthrenyl, rubicenyl and the like. In preferred embodiments, the aryl group is $(C_5-C_{20})$ aryl, with $(C_5-C_{10})$ being particularly preferred.

"Substituted Aryl:" refers to an aryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl where each R is independently —H, alkyl, alkenyl, alkynyl, aryl, arylalkyl, heteroaryl or heteroarylalkyl, as defined herein.

"Aryleno:" refers to a bivalent aromatic hydrocarbon bridge. Typical aryleno groups include, but are not limited to, benzeno, naphthaleno, anthraceno, and the like. In preferred embodiments, the aryleno group is $(C_5-C_{20})$ aryleno, with $(C_5-C_{10})$ aryleno and benzeno being particularly preferred.

"Heteroaryl:" refers to an aryl moiety wherein one or more carbon atoms are replaced with another atom, such as N, P, O, S, etc. Typical heteroaryl groups include, but are not limited to, radicals derived from acridine, benzodioxole, carbazole, β-carboline, chromane, chromene, cinnoline, furan, indazole, indole, indoline, indolizine, isobenzofuran, isochromane, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole and xanthene. In preferred embodiments, the heteroaryl group is a 5–20 membered heteroaryl, with 5–10 membered heteroaryl being particularly preferred.

"Substituted Heteroaryl:" refers to a heteroaryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, —halogen and —trihalomethyl where each R is independently —H, alkyl, alkenyl, aryl, arylalkyl, heteroaryl or heteroarylalkyl as defined herein.

"Heteroaryleno:" refers to a bivalent heterocyclic bridge. Typical heteroaryleno groups include, but are not limited to, acridino, benzodioxolo, carbazolo, β-carbolino, chromeno, cinnolino, furano, indazolo, indolo, indolizino, isobenzofurano, isochromeno, isoindolo, isoquinolino, isothiazolo, isoxazolo, naphthyridino, oxadiazolo, oxazolo, perimidino, phenanthridino, phenanthrolino, phenazino, phthalazino, pteridino, purino, pyrano, pyrazino, pyrazolo, pyridazino, pyridino, pyrimidino, pyrrolo, pyrrolizino, quinazolino, quinolino, quinolizino, quinoxalino, tetrazolo, thiadiazolo, thiazolo, thiopheno, triazole and xanthene and the like. In preferred embodiments, the heteroaryleno group is ($C_5$–$C_{20}$) aryleno, with ($C_5$–$C_{20}$) aryleno being particularly preferred.

"Arylalkyl:" refers to a straight—chain alkyl, alkenyl or alkynyl group wherein one or more of the hydrogen atoms bonded to the terminal carbon is replaced with an aryl moiety. Typical arylalkyl groups include, but are not limited to, benzyl, diphenylmethyl, naphthylmethyl, naphthobenzyl and the like. In preferred embodiments, the arylalkyl group is ($C_6$–$C_{26}$) arylalkyl, i.e., the alkyl, alkenyl or alkynyl moiety of the arylalkyl group is ($C_1$–$C_6$) and the aryl moiety is ($C_5$–$C_{20}$). In particularly preferred embodiments the arylalkyl group is ($C_6$–$C_{13}$), i.e., the alkyl, alkenyl or alkynyl moiety of the arylalkyl group is ($C_1$–$C_3$) and the aryl moiety is ($C_5$–$C_{10}$).

"Substituted Arylalkyl:" refers to an arylalkyl radical wherein one or more hydrogen atoms on the aryl moiety are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

"Heteroarylakyl:" refers to a straight-chain alkyl, alkenyl or alkynyl group where one or more of the hydrogen atoms bonded to a terminal carbon atom is replaced with a heteroaryl moiety. In preferred embodiments, the heteroarylalkyl group is a 6–26 membered heteroarylalkyl, i.e., the alkyl, alkenyl or alkynyl moiety of the heteroarylalkyl is ($C_1$–$C_6$) and the heteroaryl moiety is a 5–20-membered heteroaryl. In particularly preferred embodiments, the heteroarylalkyl is a 6–13 membered heteroarylalkyl, i.e., the alkyl, alkenyl or alkynyl moiety is ($C_1$–$C_3$) and the heteroaryl moiety is a 5–10 membered heteroaryl.

"Substituted Heteroarylakyl:" refers to an heteroarylalkyl radical wherein one or more hydrogens on the heteroaryl moiety are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

DETAILED DESCRIPTION OF THE INVENTION

Figure 1:
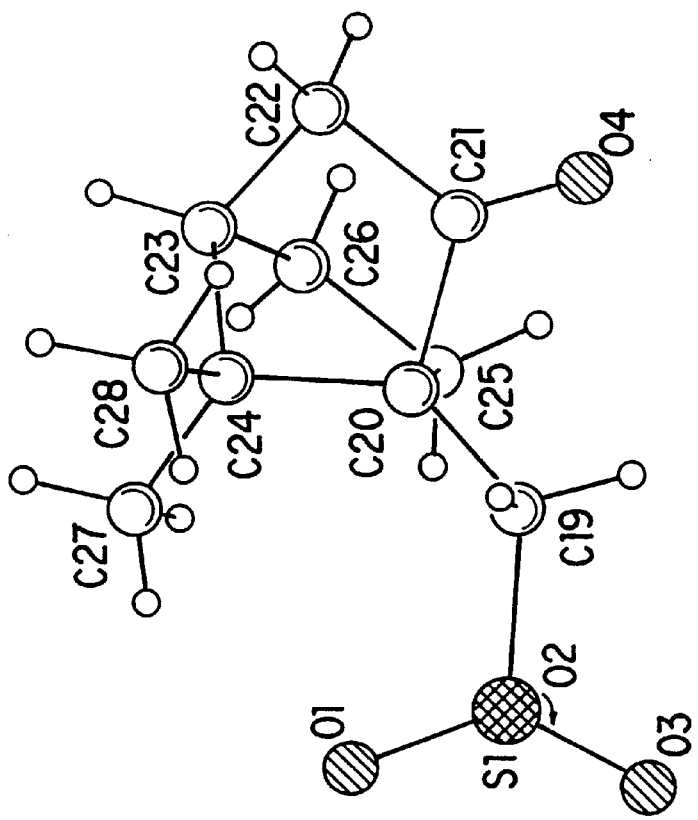
FIG. 1 shows the absolute configuration of (1R, 2S, 4R, 7S)-(−)-10-methylene-2-(p-tolyl)-8-azatricyclo [$5.2.0.0^{4,8}$] decane (Compound (−)-40), as determined by x-ray crystallography.
Figure 1:
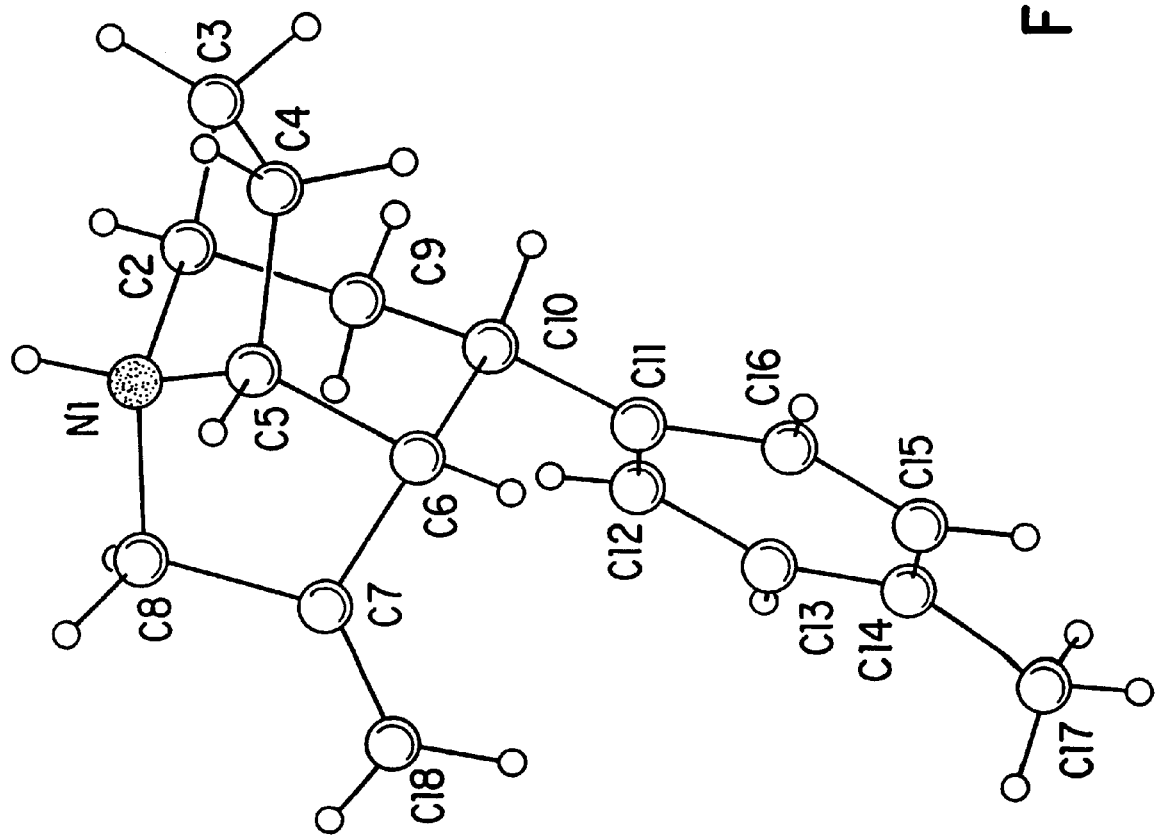

As discussed in the Background section, compounds capable of binding to the monoamine transporter and inhibiting monoamine neurotransmitter (i.e., serotonin, dopamine and/or norepinephrine) re-uptake are important classes of compounds for the treatment of a wide variety of neurological disorders and diseases. Monoamine neurotransmitter re-uptake inhibitors that selectively inhibit serotonin re-uptake, such as fluoxetine, paroxetine, citalopram, fluvoxamine, sertraline, venlafaxine, nefazadone and tianeptine, constitute a particularly important class, as these compounds induce fewer adverse side-effects than those showing little or no specificity for the serotonin transporter and/or selectivity for the dopamine or norepinephrine transporters. However, these serotonin-selective re-uptake inhibitors to varying degrees still cause several adverse side-effects, including sleep and gastrointestinal disturbances, and sexual dysfunction.

Also as discussed in the background section, inhibition of dopamine re-uptake is thought to be an important therapeutic approach towards the treatment of cocaine and other drug addiction and misuse.

The Applicants have discovered that the selectivity of tropane-like monoamine re-uptake inhibitors derives in part from the stereochemistry of the nitrogen lone pair. In particular, it has been discovered that by localizing the nitrogen lone pair over specific tropane bridge atoms by way of a tether, the specificity of the molecule for either the serotonin or dopamine transporter can be predictably adjusted. Specifically, tropane analogs in which the nitrogen lone pair is localized over the 2-carbon (ethano) bridge of the tropane moiety (front-bridged analogs) exhibit a strong preference for the serotonin transporter; tropane analogs in which the nitrogen lone pair is localized over the 3-carbon (propano) bridge of the tropane moiety (back-bridged analogs) exhibit a preference, albeit less pronounced, for the dopamine transporter. Selectivity for the norepinephrine transporter is significantly less influenced by the orientation of the nitrogen lone pair.

The stereochemistry of the nitrogen lone pair for the front-bridged and back-bridged compounds is illustrated below with exemplary compounds according to structural formulae (I), (II) and (III):

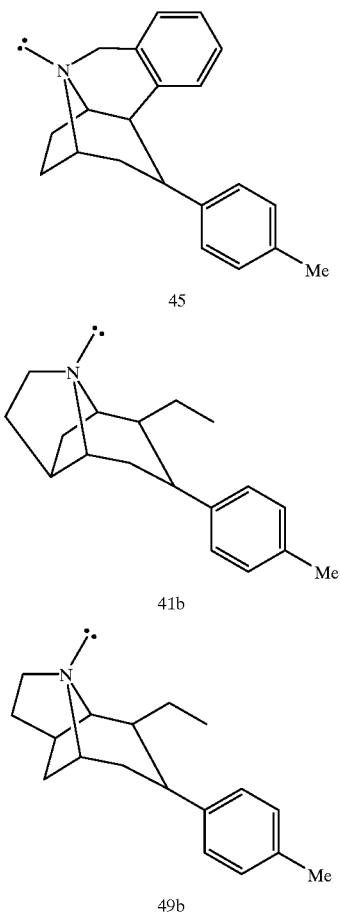

45

41b

49b

As described in the Examples section, infra, in a comparison of the ratio of re-uptake inhibition at the dopamine and serotonin transporters, the front-bridged analogs exhibited up to 77-fold greater activity at the serotonin transporter (HTT or 5-HTT), while the back-bridged analogs exhibited up to 44-fold higher activity at the dopamine transporter (DAT). While the front-bridged analogs showed up to 25-fold selectivity for the norepinephrine transporter (NET) over the dopamine transporter, the back-bridged analogs did not exhibit as dramatic a reversal in NET/DAT selectivity as observed for the HTT/DAT selectivity. Crystal structure data confirm that the observed differences in selectivity for the various monoamine transporters are due to the stereochemistry of the lone pair, and not the slight conformational changes in the tropane skeleton due to the introduction of the tether.

The discovery that differences in selectivity are induced by the stereochemistry of the nitrogen lone pair is quite surprising, particularly the DAT-selectivity of the back-bridged analogs. In previous reports, all tropane analogs bearing substituents on the 2-carbon bridge exhibited substantially reduced activity at the DAT, presumably due to adverse steric interactions in this region (Simoni et al., 1993, J. Med. Chem. 36:3975–3977; Lomenzo et al., 1997, J. Med. Chem. 40:4406–4414; Prakash et al., 1998, Med. Chem. Res. 8 (1/2):43–48) ) .

The monoamine re-uptake inhibitors of the invention find a wide variety of uses and provide significant advantages over current monoamine and serotonin-selective transporter inhibitors. For example, owing to their ability to antagonize monoamine transporters and/or inhibit monoamine re-uptake generally, the compounds of the invention are useful for treating disorders responsive to the inhibition of monoamine neurotransmitter uptake, such as depression and related disorders, panic disorders, memory deficits, attention deficit hyperactivity disorder, obesity, anxiety, cocaine and other drug addiction or misuse, obsessive-compulsive disorder and bulimic and other eating disorders. The serotonin-selective re-uptake inhibitors of the invention provide the advantage that they are able to treat the above-described disorders with fewer adverse side effects than currently available non-specific monoamine re-uptake inhibitors. The bi-cyclic serotonin-selective analogs of the invention provide the further advantage of ease of synthesis.

The ability to predictably tune the specificity of the compounds for either the dopamine or serotonin transporters provides even further advantages. For example, the dopamine transporter-selective compounds of the invention can be advantageously used to treat disorders involving dopamine re-uptake activity, such as Parkinsonism, depression, obesity, narcolepsy, cocaine and other drug addiction or misuse, attention deficit hyperactivity disorder and senile dementia, and disorders involving the release of acetylcholine, such as memory deficits (e.g., in Alzheimer's disease and presenile dementia) and chronic fatigue syndrome. The serotonin-selective compounds of the invention can be advantageously used to treat disorders involving the serotonergic neural system of the brain, such as eating disorders, depression, obsessive-compulsive disorder, panic disorders, alcoholism, pain, memory deficits and anxiety, and disorders linked to decreased transmission of serotonin in mammals, including Ganser's syndrome, migraine headache, bulimia, obesity, pre-menstrual syndrome or late luteal phase syndrome, alcoholism, tobacco abuse, panic disorder, anxiety, post-traumatic syndrome, memory loss, dementia of aging, social phobia, attention deficit hyperactivity disorder, chronic fatigue syndrome, premature ejaculation, erectile difficulties, anorexia nervosa, disorders of sleep, autism, mutism and trichotillomania.

Moreover, the transporter-selective compounds of the invention can be used in combinations specifically tailored to treat diseases involving mixed monoamine neurotransmitter re-uptake.

Compounds of the invention which exhibit dual selectivity can be used to advantageously treat disorders involving both monoamine transporters. For example compounds of the invention exhibiting activity at both the dopamine and serotonin transporters can be advantageously used to treat disorders involving both dopamine and serotonin activity, such as depression, cocaine and other drug addiction or misuse, alcoholism, and memory deficits.

Further, since the selectivity of the compounds can be predictably manipulated, they offer, for the first time, the ability to design PET and SPECT imaging agents for use in diagnosing neurodegenerative disorders. For example, compounds of the invention bearing a radiolabel (e.g., $^{11}$C, $^{15}$O, $^{13}$N, $^{18}$F, $^{67}$Ga, $^{68}$Ga, $^{123}$I, $^{131}$I, $^{99m}$Tc, or $^{201}$Tl) can be advantageously used to diagnose disorders related to a decrease in the dopamine and/or serotonin transporter population including, Parkinson's disease and other movement disorders, Ganser's syndrome, Alzheimers's disease, depression, panic disorders, anxiety, and eating disorders. Compounds labeled with $^3$H are useful for radio—ligand binding studies.

The Compounds

The compounds which exhibit increased selectivity for the serotonin transporter, and which are therefore particularly useful for treating disorders associated with the serotonergic neural system and/or decreased neurotransmission of serotonin in mammals are bi- and tricyclic aza compounds derived from tropanes in which the nitrogen lone pair is localized over the 2-carbon bridge of the tropane moiety, and which have the structural formula (I):

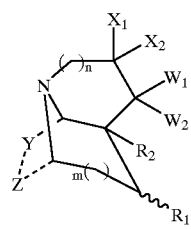

(I)

wherein:

n is 0, 1, 2 or 3;

m is 0, 1 or 2;

$X_1$, $X_2$, $W_1$ and $W_2$ taken together are $(C_5-C_{20})$ aryleno or 5–20 membered heteroaryleno, or $X_1$ and $W_1$ are each —H and $X_2$ and $W_2$ taken together form $(C_3-C_8)$ alkeno, or $X_1$ and $X_2$ are each —H and $W_1$ and $W_2$ taken together form =O, =S, =NOR$_3$, =N—CN, =N—NR$_3$R$_4$, =CR$_3$R$_4$ or $(C_3-C_8)$ alkeno, or $X_1$ and $X_2$ are each —H and $W_1$ and $W_2$ are each independently selected from the group consisting of —H, halogen, —OR$_3$, —SR$_3$, —N—NR$_3$R$_4$ or —(CH$_2$)$_o$—O—(CH$_2$)$_o$—R$_7$ where each o is independently 0, 1, 2 or 3;

Y and Z are each —H, or taken together form —(CHR$_5$)$_p$— where p is 1, 2 or 3;

$R_1$ is selected from the group consisting of $(C_5-C_{20})$ aryl, $(C_5-C_{20})$ aryl independently substituted with one or more $R_6$, 5–20 membered heteroaryl, 5–20 membered heteroaryl independently substituted with one or more $R_6$, $(C_6-C_{26})$ arylalkyl, $(C_6-C_{26})$ arylalkyl independently substituted with one or more $R_6$, 6–26 membered heteroarylalkyl and 6–26 membered heteroarylalkyl independently substituted with one or more $R_6$;

$R_2$ is —H, $(C_1-C_6)$ alkyl, $(C_2-C_6)$ alkenyl, $(C_2-C_6)$ alkynyl, $(C_5-C_{20})$ aryl, 5–20 membered heteroaryl or —(CH$_2$)$_q$—O—(CH$_2$)$_q$—R$_7$ where each q is independently 0, 1, 2 or 3;

$R_3$ and $R_4$ are each independently selected from the group consisting of —H, $(C_1-C_6)$ alkyl, $(C_2-C_6)$ alkenyl, $(C_2-C_6)$ alkynyl, $(C_5-C_{20})$ aryl, $(C_5-C_{20})$ aryl independently substituted with one or more $R_6$, 6–26 membered heteroaryl and 6–26 membered heteroaryl independently substituted with one or more $R_6$;

each $R_5$ is independently selected from the group consisting of —H, halogen, $(C_1-C_6)$ alkyl and $(C_1-C_6)$ alkyl independently substituted with one or more halogens, hydroxy or $(C_1-C_6)$ alkoxy groups;

each $R_6$ is independently selected from the group consisting of halogen, —CF$_3$, —CN, $(C_1-C_6)$ alkyl, $(C_1-C_6)$ alkenyl, $(C_1-C_6)$ alkynyl, $(C_1-C_6)$ alkoxy and $(C_3-C_6)$ cycloalkoxy; and $R_7$ is $(C_5-C_{20})$ aryl, $(C_5-C_{20})$ aryl independently substituted with one or more $R_6$, 5–20 membered heteroaryl and 5–20 membered heteroaryl independently substituted with one or more $R_6$.

The compounds which exhibit increased selectivity for the dopamine transporter, and which are therefore particularly useful for treating disorders associated with dopamine re-uptake and/or the release of acetylcholine are tri-cyclic aza compounds derived from tropanes in which the nitrogen lone pair is localized over the 3-carbon bridge of the tropane moiety, and which have the structural formula (II) or (III):

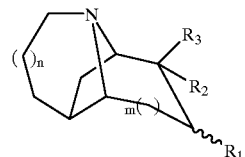

(II)

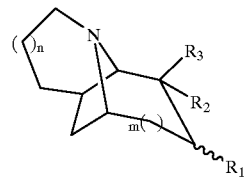

(III)

wherein n, m, $R_1$, $R_2$, and $R_3$ are as previously defined for structural formula (I).

Those of skill in the art will recognize that the compounds of structural formulae (I), (II) and (III) may exhibit the phenomena of tautomerism, conformational isomerism, geometric isomerism and/or stereoisomerism. As the formulae drawings within this specification can represent only one of the possible forms, it is to be understood that the invention encompasses any tautomeric, conformational isomeric, enantiomeric or geometric isomeric forms which exhibit biological or pharmacological activity as described herein, as well as mixtures of any of the above forms. Specifically intended to be included within the scope of the invention are the various (±), (+) and (−) stereoisomers and any mixtures thereof. Also specifically intended to be included within the scope of the invention are the chair and boat conformers, and mixtures thereof. Thus, while the various structural formulae may represent only a single stereoisomer or chair or boat conformer, unless specifically stated otherwise, the drawing is intended to include all of the various stereoisomers and conformers, as well as any mixtures of these isomeric forms. When mixtures are used, such as for example racemic mixtures, the individual components comprising the mixture need not exhibit biological or pharmacological activity, so long as the mixture exhibits activity.

The compounds of the invention can be further defined by reference to preferred embodiments, which are described below.

In one set of preferred embodiments, the compounds of the invention are compounds according to structural formula (I), with the proviso that when $R_2$ is —H, $(C_1-C_6)$ alkyl, $(C_2-C_6)$ alkenyl or $(C_2-C_6)$ alkynyl and Y and Z taken together form —(CH$_2$)—, —(CH$_2$)$_2$— or —(CH$_2$)$_3$—, then $X_1$, $X_2$, $W_1$, and $W_2$ taken together form $(C_5-C_{20})$ aryleno or 5–20 membered heteroaryleno, or $X_1$ and $W_1$ are each —H and $X_2$ and $W_2$ taken together form $(C_3-C_8)$ alkeno.

In another set of preferred embodiments, the compounds of the invention are compounds according to structural formula (I), with the proviso that when Y and Z taken together form —(CH$_2$)—, —(CH$_2$)$_2$— or —(CH$_2$)$_3$—, then $R_2$ is $(C_5-C_{20})$ aryl, 5–20 membered heteroaryl or —(CH$_2$)$_1$—O—(CH$_2$)$_q$—R$_7$ where q and $R_7$ are as previously defined.

In another set of preferred embodiments, the compounds of the invention are compounds according to structural formula (I), with the proviso that when Y and Z taken together are —(CHR)$_p$—, then at least one R$_5$ is other than —H.

In another set of preferred embodiments, the compounds of the invention are compounds according to structural formula (I), with the proviso that R$_2$ is other than —H.

In another set of preferred embodiments, the compounds of the invention are compounds according to structural formula (I), with the proviso that when Y and Z taken together form —(CH$_2$) —, —(H$_2$)$_2$— or —(CH$_2$)$_3$— and X$_1$, X$_2$ and W$_1$ are each —H, then W$_2$ is not —O—(CH$_2$)—R$_8$, where r is 0, 1, 2 or 3 and R$_8$ is (C$_5$—C$_{20}$) aryl.

In another set of preferred embodiments, the compounds of the invention are compounds according to structural formula (I), with the proviso that the compound is not any compound having the structure:

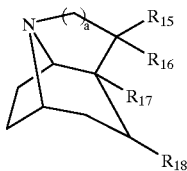

wherein:

R$_{15}$ and R$_{16}$ together form =O, =S, =NOR$_{19}$, =CR$_{20}$R$_{21}$, =N—CN, =N—NR$_{25}$R$_{26}$, —(CH$_2$)$_b$—, or —R$_{28}$—(CH$_2$)—R$_{29}$—, or one of R$_{15}$ and R$_{16}$ is —H and the other is —OR$_{22}$, —OR$_{22}$ or —NR$_{22}$R$_{23}$;

R$_{17}$ is —H or —C(O)OR$_{27}$;

R$_{20}$ and R$_{21}$ are independently —H, halogen, alkyl, cycloalkyl, cycloalkylalkyl, alkenyl, alkynyl, alkoxy, aryl, arylalkyl or —(CH$_2$)$_d$—C(O)OR$_{19}$;

R$_{19}$, R$_{22}$ and R$_{23}$ are independently —H, alkyl, cycloalkyl, cycloalkylalkyl, alkenyl, alkynyl, aryl, arylalkyl, —C (O)—alkyl or —SO$_2$-alkyl;

R$_{25}$ and R$_{26}$ are independently —H, alkyl, cycloalkyl, cycloalkylalkyl, alkenyl, alkynyl, aryl or arylalkyl;

R$_{27}$ is alkyl, alkenyl or alkynyl;

R$_{18}$ is alkyl, alkenyl alkynyl, aryl or arylalkyl, where said aryl groups my be substituted one or more times with substitutents selected from the group consisting of halogen, —CF$_3$, —CN, alkoxy, cycloalkoxy, alkyl, cycloalkyl, alkenyl, alkynyl, amino and nitro;

R$_{28}$ and R$_{29}$ are each independently O or S;

a is 1, 2, 3 or 4;

b is 2, 3, 4 or 5;

c is 1, 2, 3, 4, or 5; and d is 0, 1, 2, 3 or 4.

In another set of preferred embodiments, the compounds of the invention are compounds according to structural formula (I), with the proviso that the compound is not any compound selected from the group consisting of:

(1S,2S,4S,7R)-2-(3,4dichlorophenyl)-8-azatricyclo [5.4.0.0$^{4,8}$]undecan-11-one;

(1S,2S,4S,7R)-2-(3,4-dichlorophenyl)-8-azatricyclo [5.4.0.0$^{4,8}$]undecan-11-ol;

(1S,3S,4S,8R)-3-(3,4-dichlorophenyl)-7-azatricyclo [5.3.0.0$^{4,8}$]decan-5-one;

(1S,3S,4S,8R)-3-(3,4-dichlorophenyl)-7-azatricyclo [5.3.0.0$^{4,8}$]decan-5-one-O-methyl-oxime;

(1S,2S,4S,7R) -2- (4-chlorophenyl)-8-azatricyclo [5.4.0.0$^{4,8}$]undecan-11-one;

(1S,3S,4S,8R)-3-(3,4-dichlorophenyl)-7-azatricyclo [5.3.0.0$^{4,8}$]decan-5-ol;

(1S,3S,4S,8R)-3-(3,4-dichlorophenyl)-7-azatricyclo [5.3.0.0$^{4,8}$]dec-5-yl acetate;

(1S,3S,4S,8R)-3-(3,4-dichlorophenyl)-7-azatricyclo [5.3.0.0$^{4,8}$]dec-5-yl methane sulfate;

(1S,3S,4S,8R)-3-(3,4-dichlorophenyl)-5-methoxy-7-azatricyclo [5.3.0.0$^{4,8}$]decane;

(1S,3S,4S,8R)-3-(3,4-dichlorophenyl)-5-ethoxy-7-azatricyclo[5.3.0.0$^{4,8}$]decane;

(1S,3S,4S, 8R)-3-(4-chlorophenyl)-7-azatricyclo [5.3.0.0$^{4,8}$]decan-5-one;

(1S,3S,4S,8R)-3-(4-chlorophenyl)-7-azatricyclo [5.3.0.0$^{4,8}$]decan-5-ol;

(1S,3S,4S,8R)-3-(4-chlorophenyl)-5-ethoxy-7-azatricyclo[5.3.0.0$^{4,8}$]decane;

(1S,3S,4S,8R)-3-(3,4-dichlorophenyl)-7-azatricyclo [5.3.0.0$^{4,8}$]decan-5-one O-benzyl-oxime;

(1S,3S,4S,8R)-3-(3,4-dichlorophenyl)-7-azatricyclo [5.3.0.0 $^{4,8}$]decan-5-one O-allyl-oxime;

(1S,3S,4S,8R)-3-(3,4-dichlorophenyl)-7-azatricyclo [5.3.0.0$^{4,8}$]decan-5-one oxime;

(1S,3S,4S,8R)-3-(3,4-dichlorophenyl)-7-azatricyclo [5.3.0.0$^{4,8}$]decan-5-one O-tert-butyl-oxime;

(1S,3S,4S,8R)-3-(3,4-dichlorophenyl)-7-azatricyclo [5.3.0.0$^{4,8}$]decan-5-one O-ethyl-oxime;

(1S,3S,4S,8R)-5-allyloxy-3-(3,4-dichlorophenyl)-7-azatricyclo [5.3.0.0$^{4,8}$]decane;

Ethyl (1S,3S,4S,8R)-2-[3-(3,4-dichlorophenyl)-7-azatricyclo[5.3.0.0$^{4,8}$]dec-5-yliden]acetate;

(1S,3S,4S,8R)-3-(4-chlorophenyl)-7-azatricyclo [5.3.0.0$^{4,8}$]decan-5-one oxime;

N1-[(1S,3S,4S,8R)-3-(4-chlorophenyl)-7-azatricyclo [5.3.0.0$^{4,8}$]dec-5-yl]acetamide; and (1S,3S,4S,8R)-3-(3,4-dichlorophenyl)-7-azatricyclo [5.3.0.0$^{4,8}$]dec-5-yl amine.

Several tricyclic front-bridged inhibitors of monoamine neurotransmitter re-uptake have been described in Wo 97/16451. However, the methods reported for synthesizing these inhibitors, which utilize cocaine as a starting reagent, are not suitable for preparing (±) racemates or (+) optical enantiomers. As the synthetic methods disclosed herein are particularly suited for the preparation of these isomers, in another set of preferred embodiments, the compounds of the invention are compounds according to structure (I) which are the (±) racemates or (+) optical isomers, or mixtures thereof. Particularly preferred compounds according to this aspect of the invention are those in which Y and Z taken together form —CH$_2$—CH$_2$—.

In another set of preferred embodiments, the compounds of the invention are compounds according to structural formula (I) in which Y and Z are each —H. Particularly preferred compounds according to this aspect of the invention are those in which R$_1$ is phenyl independently substituted (preferably mono- or di-substituted) with one or more halogen (preferably —F, —Cl or —I), (C$_1$–C$_6$) alkyl (preferably methyl), (C$_2$–C$_6$) alkenyl (preferably isopropenyl), (C$_2$–C$_6$) alkynyl or (C$_1$–C$_6$) alkoxy.

In another set of preferred embodiments, the compounds of the invention are compounds according to structural formula (I), (II) or (III) in which R$_1$ is phenyl independently substituted (preferably mono- or di-substituted) with one or more halogen (preferably —F, —Cl or —I), (C$_1$–C$_6$) alkyl (preferably methyl), (C$_2$–C$_6$) alkenyl (preferably isopropenyl), (C$_2$–C$_6$) alkynyl or (C$_1$–C$_6$) alkoxy.

In another set of preferred embodiments, the compounds of the invention are compounds according to structural formulae (I) in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy; and $R_2$ is —$(CH_2)_q$—O—$(CH_2)_q$—$R_7$ where q and $R_7$ are as previously defined for structural formula (I). Particularly preferred compounds according to this aspect of the invention are those in which $X_1$, $X_2$, $W_1$ and $W_2$ are each —H, or $X_1$ and $X_2$ are each —H and $W_1$ and $W_2$ taken together form =$CH_2$.

In another set of preferred embodiments, the compounds of the invention are compounds according to structural formulae (II) or (III), with the proviso that when n is 0; m is 1; $R_1$ is phenyl or phenyl para-substituted with methyl, ($C_1$–$C_6$) alkyl, ($C_2$–$C_6$) alkenyl, ($C_2$–$C_6$) alkynyl, —Cl or halogen; and one of $R_2$ or $R_3$ is —H, then the other of $R_2$ or $R_3$ is not butyl, ($C_1$–$C_6$) alkyl, ($C_2$–$C_6$) alkenyl or ($C_2$–$C_6$) alkynyl.

In another set of preferred embodiments, the compounds of the invention are compounds according to structural formulae (II) or (III) in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy.

In still another set of preferred embodiments, the compounds of the invention are compounds according to structural formulae (I), (II) or (III) in which n is 0 and/or m is 1.

In still another set of preferred embodiments, the compounds of the invention are compounds according to structural formula (I) in which n is 1; and $X_1$, $X_2$, $W_1$, and $W_2$ taken together form ($C_5$–$C_{20}$) aryleno or 5–20 membered heteroaryleno. Particularly preferred compounds according to this aspect of the invention are those in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy.

In still another set of preferred embodiments, the compounds of the invention are compounds according to structural formula (I) in which Y and Z taken together form —CH—$CHR_5$—, where $R_5$ is halogen, ($C_1$–$C_6$) alkyl monosubstituted with a halogen, hydroxy or ($C_1$–$C_6$) alkoxy group. Particularly preferred compounds according to this aspect of the invention include those in which $X_1$ and $W_1$ are each —H and $X_2$ and $W_2$ taken together form =$CH_2$. Also particularly preferred are those compounds in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy.

In still another set of preferred embodiments, the compounds of the invention are compounds according to structural formula (I) in which $X_1$, $X_2$ and $W_1$ are each —H and $W_2$ is —$(CH_2)_p$—O—$(CH_2)_p$—$R_7$ where p and $R_7$ are as previously defined for structural formula (I). Particularly preferred compounds according to this aspect of the invention are those in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy.

In still another set of preferred embodiments, the compounds of the invention are compounds according to structural formula (I) in which $X_1$, $X_2$, $W_1$ and $W_2$ are each —H and $R_2$ is —$(CH_2)_q$—O—$(CH_2)_q$—$R_7$ where q and $R_7$ are as previously defined for structural formula (I). Particularly preferred compounds according to this aspect of the invention are those in which $R_1$ is phenyl independently substituted (preferably mono- or di-substituted) with one or more halogen (preferably —F, —Cl or —I), ($C_1$–$C_6$) alkyl (preferably methyl), ($C_2$–$C_6$) alkenyl (preferably isopropenyl), ($C_2$–$C_6$) alkynyl or ($C_1$–$C_6$) alkoxy.

In yet another preferred embodiment, the compounds of the invention are compounds according to structural formulae (I) which are selected from the group consisting of structures (III), (IV) and (V):

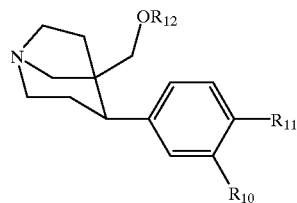

(IV)

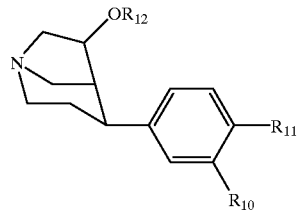

(V)

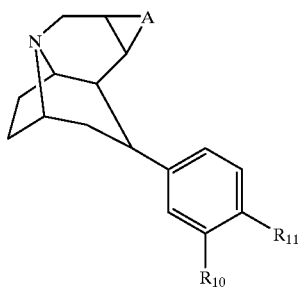

(VI)

wherein:

$R_{10}$ is halogen, —F, —Cl, —Br, —I, methyl, ($C_1$–$C_6$) alkyl, ($C_2$–$C_6$) alkenyl or ($C_2$–$C_6$) alkynyl;

$R_{11}$ is halogen, —F, —Cl, —Br, —I, methyl, ($C_1$–$C_6$) alkyl, ($C_2$–$C_6$) alkenyl or ($C_2$–$C_6$) alkynyl;

$R_{12}$ is benzodioxolyl, 1,3-benzodioxol-5-yl, (trihalomethyl)phenyl, 4-(trihalomethyl)phenyl, (trifluoromethyl)phenyl, 4-(trifluoromethyl)phenyl, halophenyl, 4-halophenyl, fluorophenyl and 4-fluorophenyl; and A is benzeno or naphthaleno.

In yet another preferred embodiment, the compounds of the invention are compounds according to structural formula (II) or (III) which have the structure (VII) or (VIII):

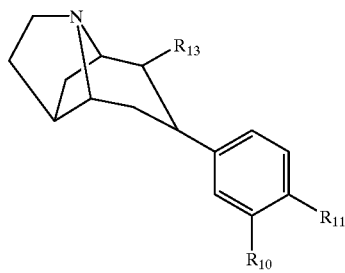

(VII)

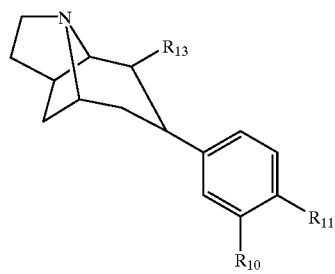

(VIII)

wherein:

$R_{10}$ and $R_{11}$ are as previously defined for structural formulae (IV)–(VI); and $R_{13}$ is —H, $(C_1-C_6)$ alkyl, $(C_1-C_6)$ alkenyl, $(C_1-C_6)$ alkynyl or $(C_5-C_{20})$ aryl.

In still another set of preferred embodiments, the compounds of the invention are compounds according to structural formula (I) which are selected from the following group of compounds:

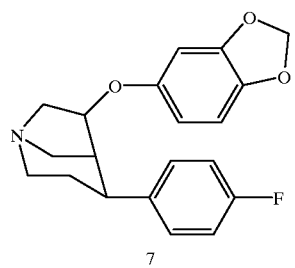

7

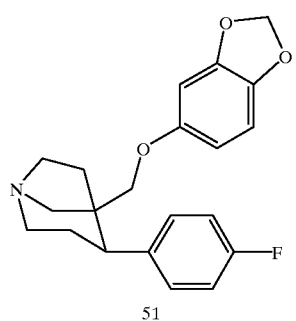

51

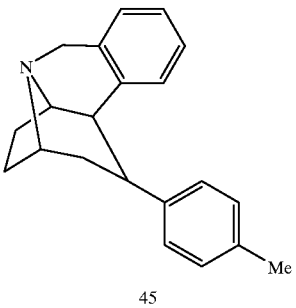

45

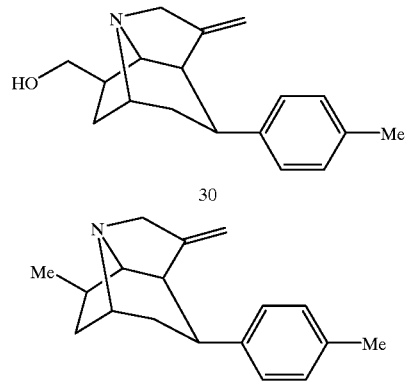

30

31

In still another set of preferred embodiments, the compounds of the invention are compounds according to structure (I) which are the (±) or (+) optical isomers of the following compound, in either the chair or boat conformation:

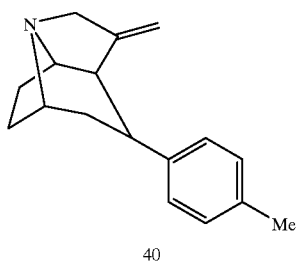

40

In still another set of preferred embodiments, the compounds of the invention are compounds according to structural formula (II) which are selected from the following group of compounds:

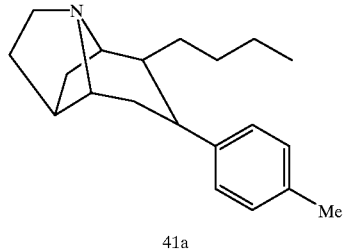

41a

-continued

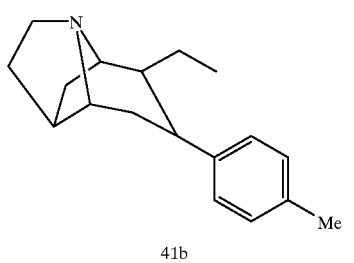

41b

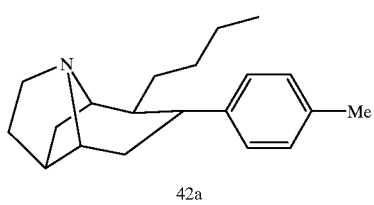

42a

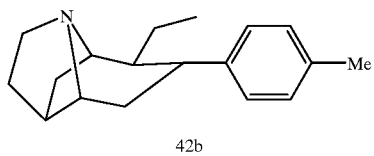

42b

In a final set of preferred embodiments, the compounds of the invention are compounds according to structural formula (III) which are selected from the following group of compounds:

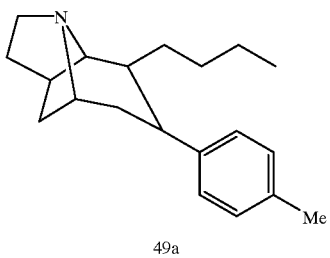

49a

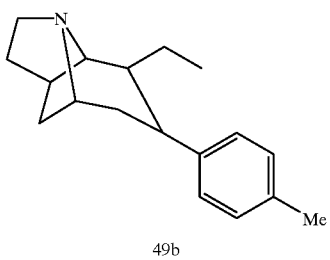

49b

-continued

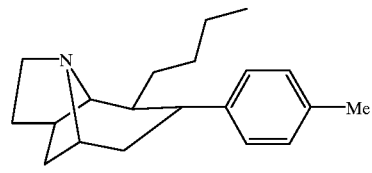

50a

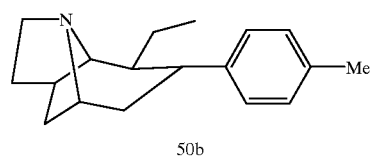

50b

The compounds of the invention may be in the form of free acids, free bases or pharmaceutically effective salts thereof. Such salts can be readily prepared by treating a compound with an appropriate acid. Such acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propanedioic acid, butanedioic acid, oxalic acid, fumaric acid, glycolic acid, malonic acid, etc. Conversely, the salt can be converted into the free base form by treatment with alkali.

In addition to the above-described compounds and their pharmaceutically acceptable salts, the invention may employ, where applicable, solvated as well as unsolvated forms of the compounds (e.g. hydrated forms).

Synthetic Methods

The compounds of the invention may be prepared by any processes known to be applicable to the preparation of chemical compounds. Suitable processes are well known in the art, and are described, for example, in WO 97/16451 and Smith et al., 1998, Tetrahedron Lett. 39:197–200, and the references cited therein. Preferred processes are illustrated by the representative examples. Necessary starting materials may be obtained commercially or by standard procedures of organic chemistry. Exemplary processes are illustrated below, as well as in the Examples section.

6-keto bicyclic analogs of the invention can be readily prepared as outline in Scheme (I), below:

SCHEME (I)

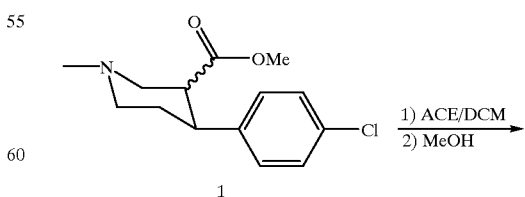

1

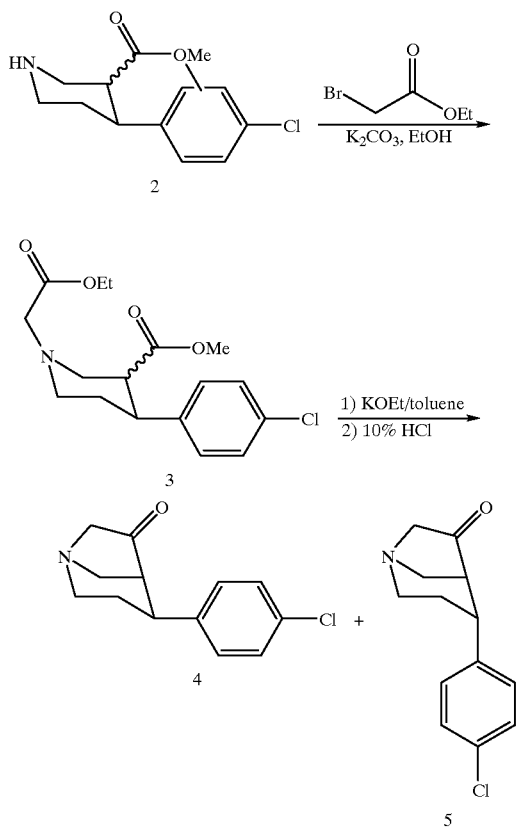

According to Scheme (I), an appropriately 4-substituted N-methyl-3-alkoxycarbonyl piperidine 1 prepared by addition of the appropriate 4-substituted phenylmagnesium bromide to arecoline as described in Kozikowski et al., 1998, J. Med. Chem. 41:1962–1969) is N-demethylated with chloroethyl chloroformate (ACE) to afford piperidine 2. Alkylation with ethyl bromoacetate in ethanol affords the diester 3 which undergoes the Dieckmann condensation to afford, after decarboxylation, a mixture of the bicyclic ketones 4 and 5.

Other bicyclic 6-keto analogs according to the invention can be prepared by manipulating the synthesis reagents. For example, 6-keto analogs having substituents other than 4-chlorophenyl at the 4-position can be readily prepared by starting with an appropriately 4-substituted N-methyl piperidine. Compounds containing additional bridge atoms can be prepared by reacting piperidine 2 with the appropriate alkyl bromoalkylester.

The enantiomers of both isomers 4 and 5 can be resolved by treatment with readily available chiral acids: (1R)-(−)-10-camphorsulfuric acid for ketone 4 and dibenzyl-1-tartaric acid for ketone 5.

Ketones 4 and 5 can be used to synthesize additional 6-substituted bicyclic analogs according to the invention as outlined in Schemes (II) and (III):

SCHEME (II)

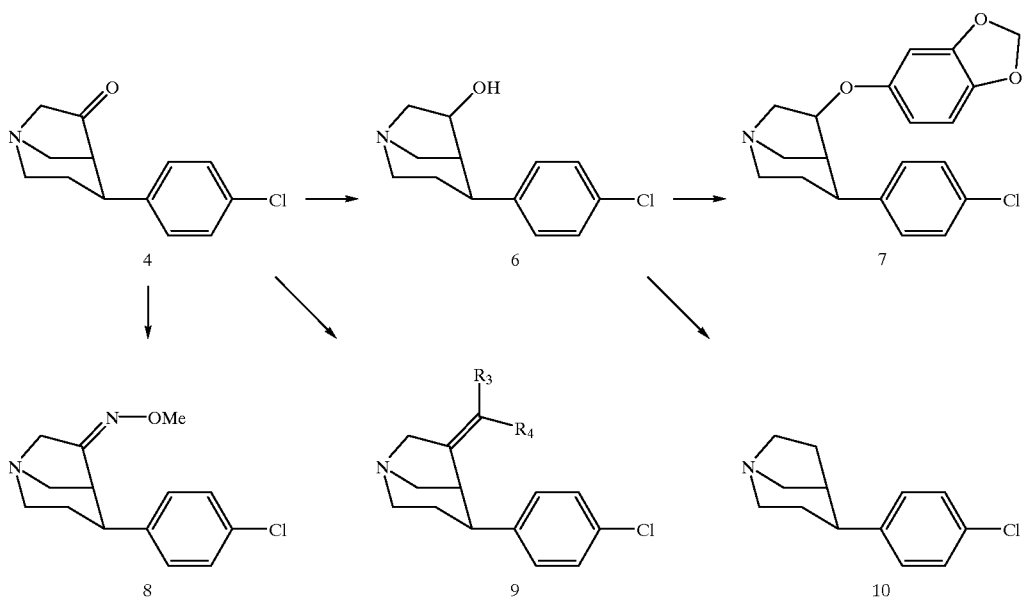

SCHEME (III)

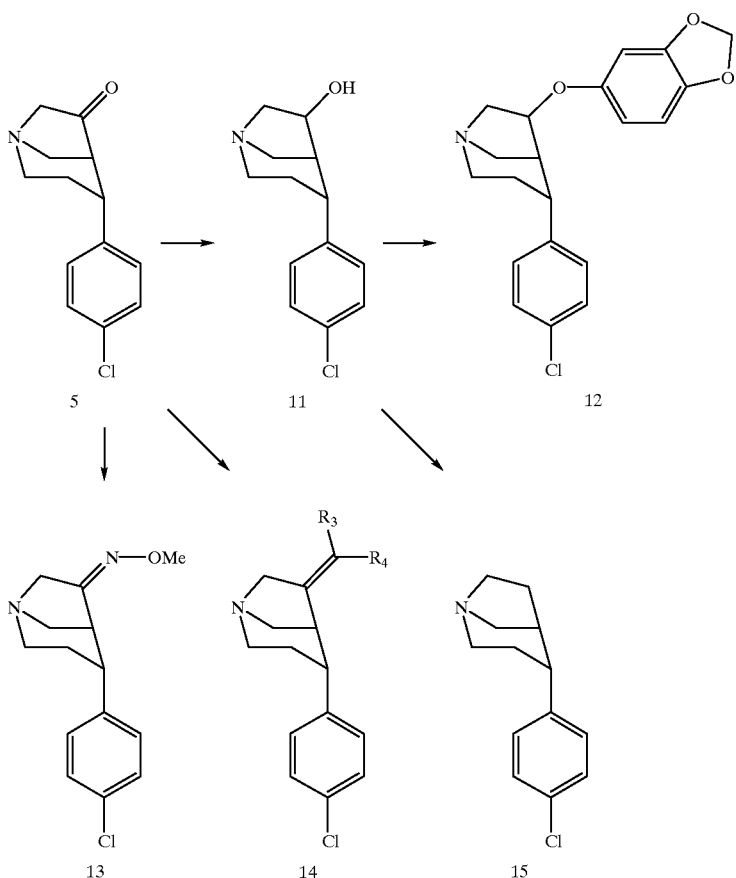

According to Scheme (II), ketone 4 can be readily reduced using diisobutylaluminum hydride (DIBAL) at −78° C. in methylene chloride to afford the endo-alcohol 6. This alcohol can then be either converted to the mesylate and coupled with the sodium salt of sesamol to afford the methylenedioxophenyl ether 7 or deoxygenated using the Barton-McCombie protocol to afford 10. Alternatively ketone 4 can be treated with O-methyl hydroxylamine hydrochloride to afford a mixture of the cis- and trans- oximes 8, that can be separated by chromatography. Ketone 4 can also be utilized in a Wittig or Horner-Emmons olefination to afford alkene 9 (where $R_3$ and $R_4$ are as defined for structure (I)).

According to Scheme (III), ketone 5 can be readily modified utilizing the conditions outlined for 4, above, to yield compounds 11, 12, 13, 14 (where $R_3$ and $R_4$ are as defined for structure (I)) and 15.

All of the above compounds can be prepared as either racemic mixtures or as pure enantiomers, depending upon whether racemates or pure enantiomers of ketones 4 and 5 are used as starting materials. Quite surprisingly, there was an unexpected inversion in the optical rotation of methylenedioxophenyl ether 7. As a consequence, enantiomerically pure (+)-7 is prepared from compound (−)-6; enantiomerically pure (−)-7 is prepared from compound (+)-6.

Additional analogs of compounds 10 and 15 containing substituents at the 3-position of the piperidine ring can be synthesized as outlined in Schemes (IV) and (V):

SCHEME (IV)

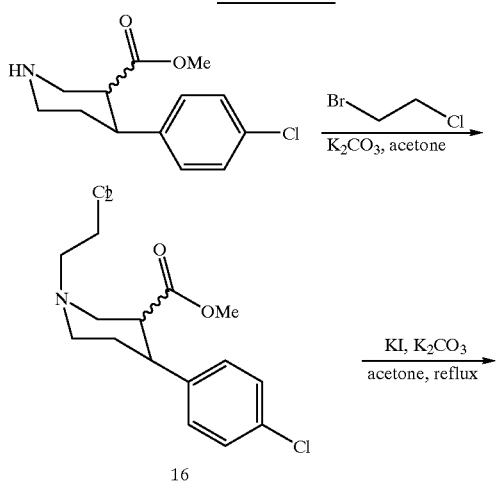

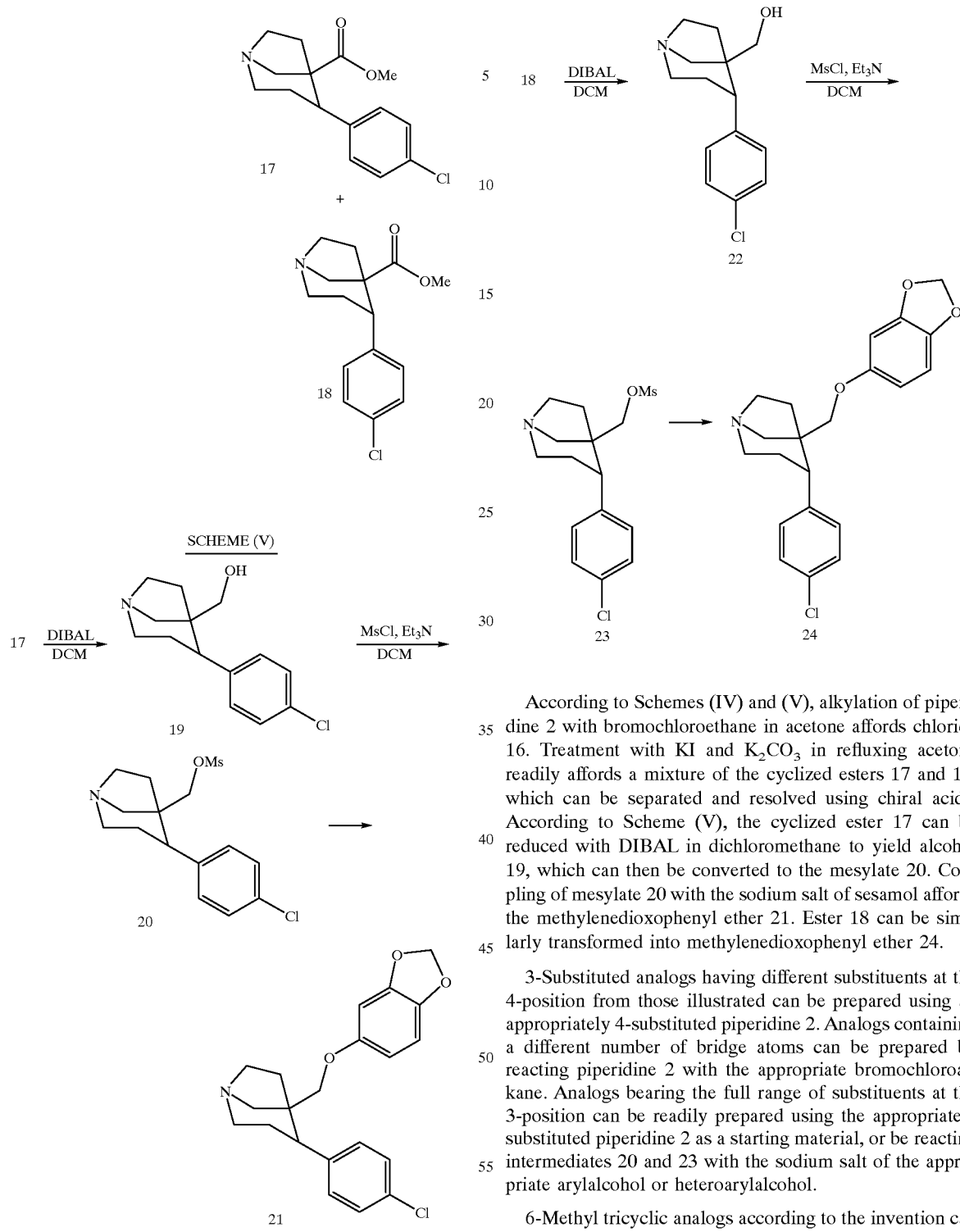

According to Schemes (IV) and (V), alkylation of piperidine 2 with bromochloroethane in acetone affords chloride 16. Treatment with KI and $K_2CO_3$ in refluxing acetone readily affords a mixture of the cyclized esters 17 and 18, which can be separated and resolved using chiral acids. According to Scheme (V), the cyclized ester 17 can be reduced with DIBAL in dichloromethane to yield alcohol 19, which can then be converted to the mesylate 20. Coupling of mesylate 20 with the sodium salt of sesamol affords the methylenedioxophenyl ether 21. Ester 18 can be similarly transformed into methylenedioxophenyl ether 24.

3-Substituted analogs having different substituents at the 4-position from those illustrated can be prepared using an appropriately 4-substituted piperidine 2. Analogs containing a different number of bridge atoms can be prepared by reacting piperidine 2 with the appropriate bromochloroalkane. Analogs bearing the full range of substituents at the 3-position can be readily prepared using the appropriately substituted piperidine 2 as a starting material, or be reacting intermediates 20 and 23 with the sodium salt of the appropriate arylalcohol or heteroarylalcohol.

6-Methyl tricyclic analogs according to the invention can be synthesized according to Scheme (VI):

SCHEME (VI)

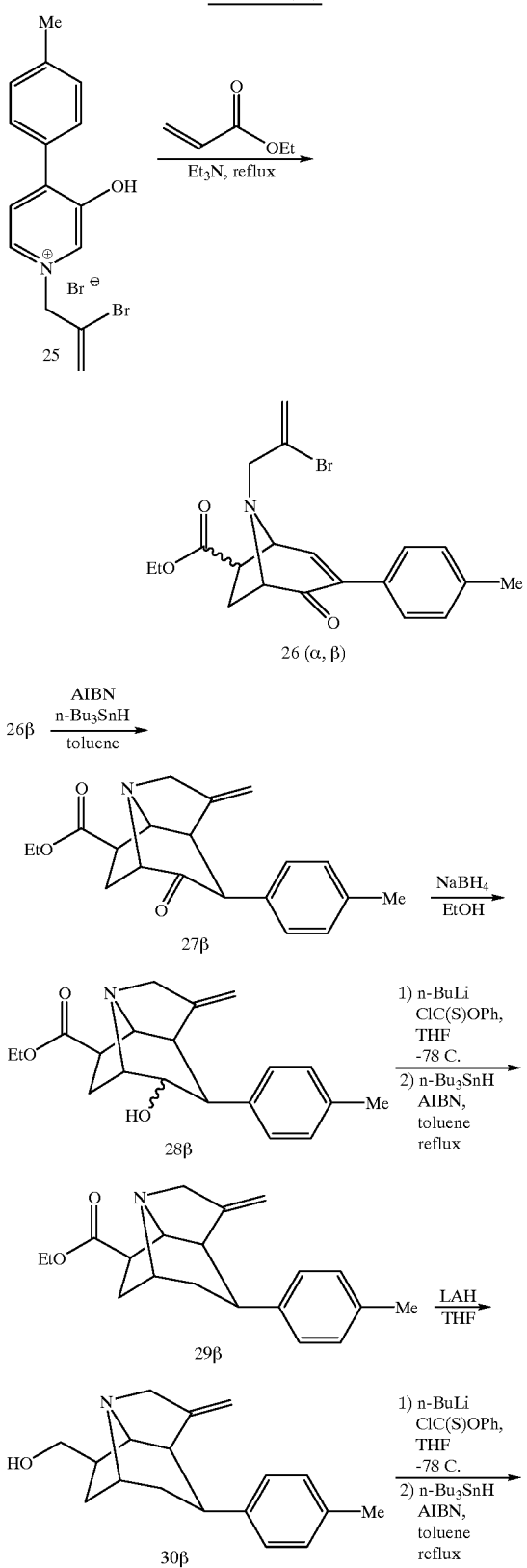

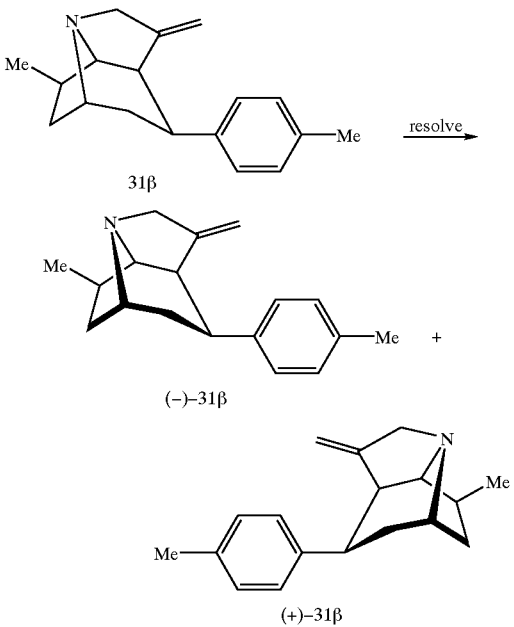

According to Scheme (VI), the dipolar cycloaddition of the betaine prepared in situ from pyridinium salt 25 (prepared as described in Smith et al., 1998, Tetrahedron Lett. 39:199–200) and ethyl acrylate affords a crude mixture of α and β esters 26α and 26β that can be separated by chromatography. The β-ester 26β undergoes a radical cyclization to afford ketoester 27α. The selective reduction of ketoester 27β with NaBH$_4$ in EtOH affords alcohol 28β. Conversion to the thionocarbonate and radical deoxygenation readily affords ester 29β. Reduction to the alcohol with LAH followed by conversion to the thionocarbonate and deoxygenation affords the 6β-methyl analog 31β as a racemic mixture. This racemic compound can be resolved using commercially available chiral acids to afford the enantiomeric pure tricyclic compounds (−)-31β and (+)-31β.

The α-analogs can be prepared as described above in Scheme (VI) using 26α as a starting material, as illustrated in Scheme (VIa):

SCHEME (VIa)

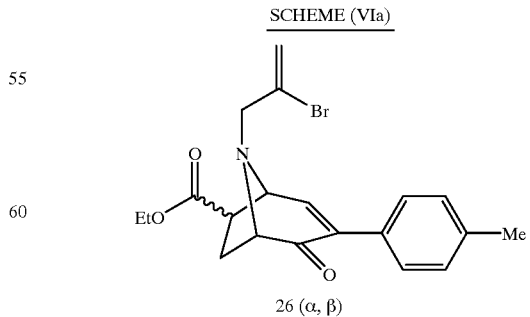

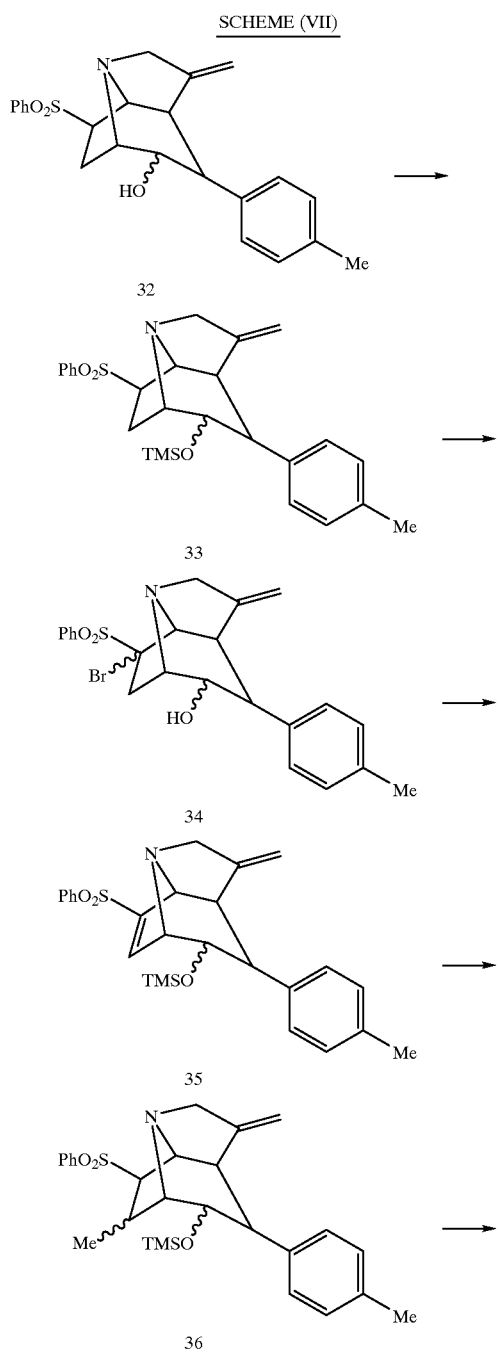

7-methyl tricyclic analogs can be prepared from intermediate 32 (prepared as described in Smith et al., 1998, Tetrahedron Lett. 39:199–200) as outlined in Scheme (VII):

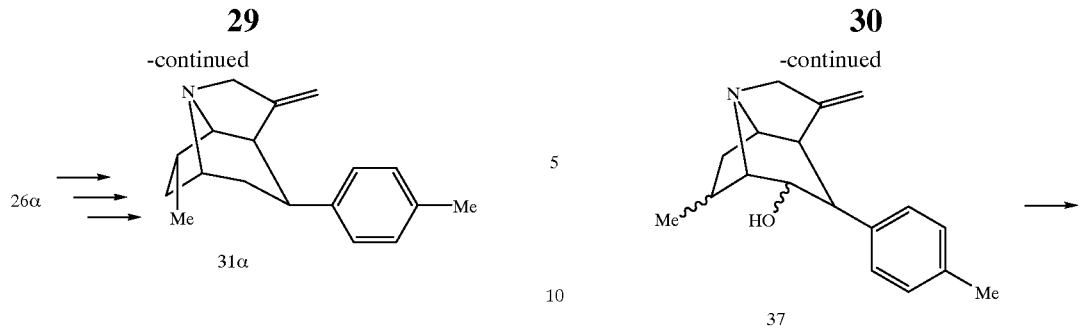

According to Scheme (VII), protection of the secondary alcohol as the trimethylsilyl (TMS) ether followed by bromination α to the sulfone affords bromide 34. Dehydrobromination followed by conjugate addition to the resulting alcohol furnishes a mixture of the 7α and 7β methyls (36). Reductive desulfonylation followed by deprotection of the silyl ether affords the alcohols 37 as a mixture of isomers. The two-step deoxygenation sequence affords a mixture of the 7β methyl compound 38 along with the 7α methyl compound 39.

Tricyclic analogs in which $X_1$, $X_2$, $W_1$ and $W_2$ taken together are an aryleno or heteroaryleno can be prepared as outline in Scheme (VIII):

SCHEME (VIII)

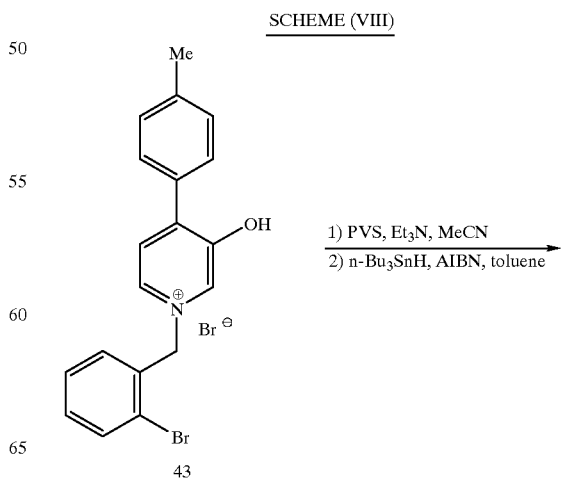

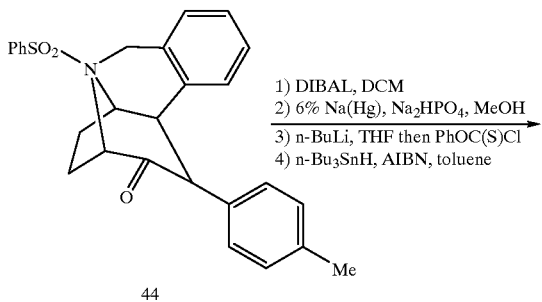

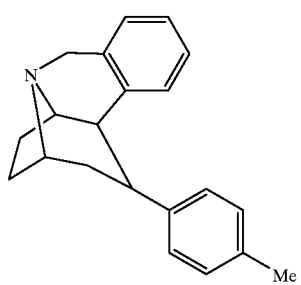

According to Scheme (VIII), pyridinium salt 43 can be readily prepared by the N-alkylation of 3-hydroxy-4-(p-tolyl)pyridine with 2-bromobenzyl bromide in THF. Using the tandem cycloaddition/radical cyclization methodology, the tricyclic ketone 44 is obtained as a single isomer. This intermediate is further converted to the desired benzeno bridged tropane 45 by a modification of the route previously discussed in Schemes (VI) and (VII).

Tricyclic analogs bearing other aryleno or heteroaryleno bridges can be readily obtained from the appropriate pyridinium salt, as will be apparent to those of skill in the art. Tricyclic analogs in which $X_2$ and $W_2$ are an alkeno group can be readily synthesized using the above-described methods with the following pyridinium salt as a starting material:

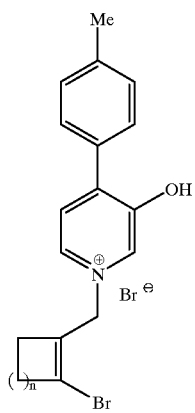

Back-bridged analogs according to the invention can be synthesized according to Scheme (IX):

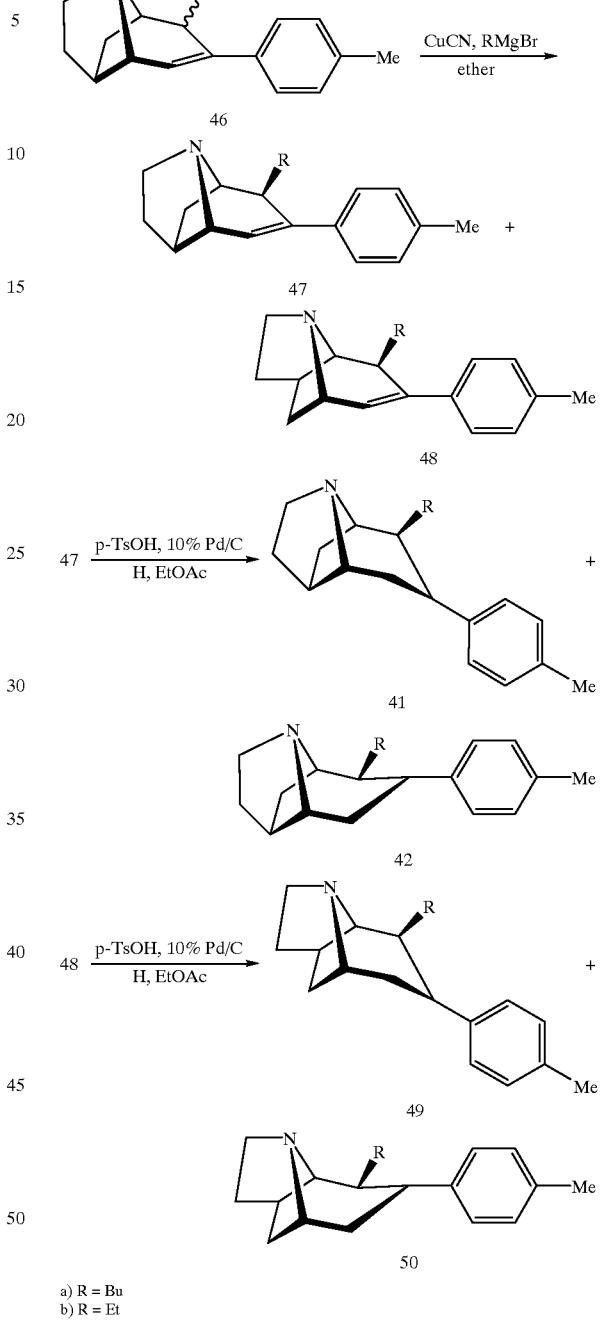

a) R = Bu
b) R = Et

In Scheme (IX), compounds in which R is butyl are designated "a" compounds, e.g., Compound "50a"; those in which R is ethyl are designated "b" compounds, e.g., Compound "50b". Compounds bearing other alkyl, alkenyl or akynyl substiuents at this position can be readily prepared by choosing the appropriate Grignard reagent.

Referring to Scheme (IX), the CuCN catalyzed cross coupling of allylic acetate 46 with the appropriate Grignard reagent affords a mixture of the 2β-olefins 47 and 48. These olefins can be readily separated and individually subjected to hydrogenation under acidic conditions to afford the desired 3β and 3α analogs.

Those of skill in the art will appreciate that the above-described syntheses can be used to synthesize the full range of compounds according to structural formulae (I), (II) and (III) by routine modification of the exemplified starting materials and reactants. Some of the compounds of the invention may contain functional group substituents that are reactive under the conditions used to synthesize the compounds. When present, such groups should be protected with an appropriate protecting group. Protecting groups suitable for the particular functional group and reaction conditions will be apparent to those of skill in the art. Suitable protecting groups, as well as methods for their attachment and detachment, are described, for example, in Greene & Wuts, 1991, Protective Groups in Organic Synthesis, John Wiley & Sons, New York.

Compounds of the invention may exist in (+) optical forms, (−) optical forms and racemic mixtures of (±) optical forms. Racemic mixtures can be resolved into the optical enantiomers by known methods, for example, by separation of diastereomeric salts thereof with an optically active acid, and librating the optically active amine compound by treatment with a base. Another method for resolving racemates into the optical entantiomers is based upon chromatography on an optically active matrix. Recemic compounds of the present invention can thus be resolved into their optical enantiomers, for example, by fractional crystallization of d- or 1- salts such as tartrates, mandelates or camphorsulphonates.

The compounds may also be resolved by the formation of diastereomeric amides by reaction of the compounds with an optically active activated carboxylic acid such as that derived from (+) or (−) phenylalanine, (+) or (−) phenylglycine, (+) or (−) camphoric acid or by the formation of diastereomeric carbamates by reaction of the compounds of the invention with an optically active chloroformate or the like. Additional methods for resolving the optical enantiomers will be apparent to those of skill in the art, and include, for example, the methods described in Collet & Eilan, 1981, Enantiomers, Racemates and Resolutions, John Wiley & Sons, New York.

Activity and Selectivity

An individual compound's relevant activity and potency as an agent to inhibit monoamine neurotransmitter re-uptake and/or to treat disorders associated with monoamine neurotransmitter re-uptake can be determined using a variety of standard techniques. In general, the active compounds of the invention are those which act as monoamine transporter antagonists (i.e., bind monoamine transporters) and/or inhibit monoamine neurotransmitter re-uptake. Active compounds of the invention will typically exhibit a $K_i$ for inhibition (or binding) in the range of $10^{-5}$ to 10 $\mu$M. Compounds which exhibit a 10-fold or greater difference in potentcy are considered selective for a particular transporter.

Formulation and Routes of Administration

The compounds described herein, or pharmaceutically acceptable addition salts or hydrates thereof, can be delivered to a subject, including humans, using a wide variety of routes or modes of administration. Suitable routes of administration include, but are not limited to, inhalation, transdermal, oral, rectal, transmucosal, intestinal and parenteral administration, including intramuscular, subcutaneous and intravenous injections, with oral administration being preferred.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, the compounds can be administered in cocktails containing other agents that are commonly used to treat such disorders, including other monoamine neurotransmitter inhibitors, such as methylphenidate, fluoxetine, paroxetine, citalopram, venlafaxine, imipramine and amitriptyline.

As a significant advantage of the compounds of the invention is their selectivity for inhibiting certain monoamine transporters, the compounds can be advantageously administered in combination. The specific combination utilized can be tailored to target the particular transporters thought to be involved in the mechanistic pathway of the disorder and/or to reduce the incidence of adverse side-effects. For example, where both serotonin and dopamine re-uptake are involved in a disorder, a mixture of the serotonin-selective front-bridged compounds of the invention and the dopamine-selective back-bridged compounds of the invention can be administered (either concurrently or non-concurrently) which is specifically tailored to treat the disorder, while at the same time reducing or minimizing adverse side-effects. The ability to determine combinations of compounds suitable to treat particular disorders is well-within the capabilities of those having skill in the art.

The active compound(s) may be administered per se or in the form of a pharmaceutical composition containing the active compound(s) and one or more pharmaceutically acceptable carriers, excipients or diluents. Administered compounds may be enantiomerically pure, or may be mixtures of enantiomers. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations previously described, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosages

Pharmaceutical compositions suitable for use with the present invention include compositions wherein the active ingredient is contained in an amount effective to achieve its intended purpose, either therapeutically or prophylactically. For example, when administered as an anti-depressant, such compositions will contain an amount of active ingredient effective to therapeutically treat depression and/or the symptoms associated with depresssion or to prophylactically to prevent the onset of depression. Of course, the actual amount effective for a particular application will depend upon a variety of factors including, inter alia, the condition being treated, the age and weight of the patient and the judgment of the prescribing physician.

For any compound described herein the therapeutically effective amount for use in humans can be readily determined from in vitro data or relevant animal models. For example, a dose for humans can be formulated to achieve a circulating concentration of active ingredient which produced a specified level of monoamine neurotransmitter re-uptake inhibition in in vitro tests. A particularly convenient concentration to achieve is that concentration of active ingredient which inhibits 50% of monoamine neurotransmitter re-uptake ($IC_{50}$); however, the desired level of inhibition will depend on the particular disease mechanism, and will be apparent to those of skill in the art. Where selective inhibition is desired, a dose can be formulated which yields a circulating concentration of active ingredient that produces a specified level of inhibition of the specific monoamine neurotransmitter re-uptake.

Alternatively, a dose for humans can be formulated to achieve a circulating concentration of active ingredient equal to the $K_i$ observed in in vitro tests. Again, where selectivity is desired, the $K_i$ for the particular transporter would be relevant.

A dose for humans can also be formulated to achieve a circulating concentration that has been found to be effective in animal models for the particular indication being treated. Useful animal models for depression and the other myriad psychological disorders that can be treated with the compounds described herein are well-known in the art, and can be found, for example, in Porsolt, 1993, Pharmacopsychiatry 26(1) :20–14.

A therapeutically effective dose can further be determined from animal or human data for compounds which are known to exhibit similar pharmacological activities, including other monoamine neurotransmitter re-uptake inhibitors such as methylphenidate, fluoxetine, paroxetine, citalopram, venlafaxine, imipramine and amitriptyline. The applied dose can be adjusted based on the relative bioavailability, potency and in vivo half-life of the administered compound as compared with these other agents.

Adjusting the dose to achieve maximal efficacy in humans based on the methods described above and other methods that are well-known in the art is well within the capabilities of the ordinarily skilled artisan. Of course, in the case of local administration, the systemic circulating concentration of administered compound will not be of particular importance. In such instances, the compound is administered so as to achieve a concentration at the local area effective to achieve the intended result.

For use in treating depression, patient doses for oral administration of the compounds described herein typically range from about 0.1 mg/day to 500 mg/day, more typically from about 1 mg/day to 100 mg/day, and most typically from about 10 mg/day to 50 mg/day. The actual dosage levels used are expected to differ depending on, inter alia, the indication and severity of disorder. The exact dosage can best be chosen by the individual physician in view of the patient's condition.

For other modes of administration, dosage amount and interval can be adjusted individually to provide plasma levels of the administered compound effective for the particular clinical indication being treated.

The compounds can be administered therapeutically to treat a variety of psychological and other disorders, such as depression, after the onset of symptoms. However, in many instances the compounds are expected to be administered prophylactically or chronically to treat or prevent a variety of psychological disorders, such as depression, prior to the onset of symptoms.

Combined with the teachings provided herein, by choosing among the various active compounds and weighing factors such as potency, relative bioavailability, patient body weight, severity of adverse side-effects, preferred mode of administration, and duration between injury and treatment, an effective therapeutic treatment regimen can be planned which does not cause substantial toxicity and yet is entirely effective to treat or prevent the clinical symptoms demonstrated by the particular patient.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, In: The Pharmacological Basis of Therapeutics).

The invention having been described, the following examples are intended to illustrate, not limit, the invention.

EXAMPLE: Compound Syntheses

This Example demonstrates preferred methods for synthesizing certain exemplary compounds according to the invention.

Starting materials were obtained from Aldrich Chemical Co. (St. Louis, Mo.) or from other commercial suppliers. Solvents were purified as follows: diethyl ether and THF were freshly distilled under nitrogen from sodium-benzophenone.

Infrared (IR) spectra were recorded on an ATI Mattson Genesis spectrometer. $^1$H and $^{13}$C Nuclear magnetic resonance (NMR) spectra were obtained with a Varian Unity Inova instrument at 300 and 75.46 MHz, respectively. $^1$H chemical shifts ($\delta$) are reported in ppm downfield from internal tetra-methylsilane (TMS). $^{13}$C chemical shifts are referenced to CDCl$_3$ (central peak, $\delta$=77.0 ppm), benzene-d$_6$ (central peak, $\delta$=128.0 ppm), or CDCl$_3$ (central peak, $\delta$=39.7 ppm).

Melting points were determined in Pyrex capillaries with a Thomas Hoover Unimelt apparatus and are uncorrected. Mass spectra were measured in the EI mode at an ionization potential of 70 eV. Thin-layer chromatography (TLC) was performed on Merck silica gel 60F$_{254}$ glass plates; column chromatography was performed using Merck silica gel (60–200 mesh). The following abbreviations are used: DMSO is dimethyl sulfoxide; ether is diethyl ether; THF is tetrahydrofuran; MeOH is methanol; EtOH is ethanol; EtOAc is ethyl acetate; Et$_3$N is triethylamine; KHMDS is potassium hexamethyldisilazane; AIBN is azo-bis-isobutyronitrile.

In all the syntheses that follow, the various compound reference numbers correspond to those used in Schemes (I)–(IX), supra. Unless otherwise noted, all reactions were performed under inert atmosphere.

6.1 Synthesis of (3SR, 4SR) Methyl 4-(4-Chlorophenyl)-piperidine-3-carboxylate (Compound (±)-2))

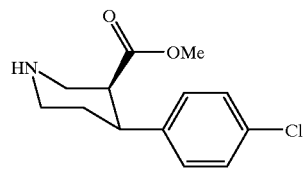

A solution of (3S, 4S) methyl 4-(4-chlorophenyl)-1-methylpiperidine 3-carboxylate (Compound (±)-1) (8.9 g, 33 mmol) and chloroethyl chloroformate (5.4 mL, 50 mL) in dichloromethane (30 mL) was heated to reflux for 3 h, cooled and diluted with a solution of 1M HCl in ether (40 mL). The resulting solution was filtered through a short column of silica gel with CH$_2$Cl$_2$ (100 mL) and the solvents removed. The residual oil was heated to reflux in MeOH (80 mL) for 16 h. The resulting mixture was cooled and diluted with water (50 mL) made basic with Na$_2$CO$_3$ and extracted with CH$_2$Cl$_2$ (3×100 mL). The pooled extracts were dried (Na$_2$SO$_4$) and concentrated. Chromatography (EtOAc/Et$_3$N, 9:1) afforded Compound (±)-2 (6.5 g, 78%) as a clear colorless oil: R$_f$ 0.1 (EtOAc/Et$_3$N, 9:1); MS m/z 253 (M$^+$), 57 (100); $^1$H NMR (CDCl$_3$) $\delta$ 1.63 (br s, 1H, J=13 Hz), 1.88 (br s, 1H), 2.34 (m, 1H), 2.67–2.77 (m, 2H), 2.95–3.00 (m, 2H), 3.28–3.37 (m, 2H), 3.44 (s, 3H), 7.12 (d, 2H, J=8.4 Hz), 7.34 (d, 2H, J=8.4 Hz); $^{13}$C NMR (CDCl$_3$) $\delta$ 26.7, 42.8, 45.7, 46.5, 49.1, 50.9, 128.3, 128.4, 132.1, 141.9, 173.7.

6.2 Synthesis of (3S, 4S) Methyl 4-(4-Chlorophenyl)-piperidine-3-carboxylate (Compound (−)-2))

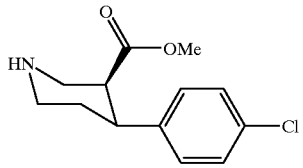

Prepared as described above from Compound (−)-1 to afford Compound (−)-2 (77%) as a clear colorless oil: $[\alpha]_D$−132 (c 1.1, EtOH); $R_f$ 0.1 (EtOAc/Et$_3$N, 9:1); MS m/z 253 (M$^+$), 57 (100); $^1$H NMR (CDCl$_3$) δ 1.63 (br s, 1H, J=13 Hz), 1.88 (br s, 1H), 2.34 (m, 1H), 2.67–2.77 (m, 2H), 2.95–3.00 (m, 2H), 3.28–3.37 (m, 2H), 3.44 (s, 3H), 7.12 (d, 2H, J=8.4 Hz), 7.34 (d, 2H, J=8.4 Hz); $^{13}$C NMR (CDCl$_3$) δ 26.7, 42.8, 45.7, 46.5, 49.1, 50.9, 128.3, 128.4, 132.1, 141.9, 173.7.

6.3 Synthesis of (3R, 4R) Methyl 4-(4-Chlorophenyl)-piperidine-3-carboxylate (Compound (+)-2))

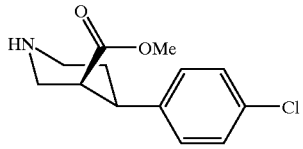

Prepared as described above from Compound (+)-1 to afford Compound (+)-2 (77%) as a clear colorless oil: $[\alpha]_D$+140 (c 1.2, EtOH). Spectral data same as for (−)-2.

6.4 Synthesis of (3SR, 4SR) Methyl 4-(4-Chlorophenyl)-1(ethoxycarbonylmethyl) piperidine-3-carboxylate (Compound (±)-3))

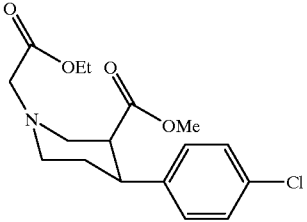

To solution of Compound (±)-2 (6.3 g, 25 mmol) and ethyl 3-bromoacetate (4.1 mL, 37 mmol) in EtOH (100 mL) was added K$_2$CO$_3$ (6.8 g, 49 mmol). The resulting suspension was stirred at 50° C. for 15 h and the resulting mixture was cooled and diluted with water (100 mL), satd. NaHCO$_3$ (100 mL) and extracted with CH$_2$Cl$_2$ (3×100 mL). The pooled extracts were dried (Na$_2$SO$_4$) and concentrated. Chromatography (hexanes/EtOAc, gradient 1:0 to 1:1) afford Compound (±)-3 (8.4 g, 100%) as a clear colorless oil: $R_f$ 0.5 (hexanes/EtOAc, 1:1); MS m/z 339 (M$^+$), 266 (100); ); $^1$H NMR (CDCl$_3$) δ 1.27 (t, 3H, J=7.2 Hz), 1.79–1.92 (m, 2H), 2.33–2.48 (m, 2H), 2.79 (dt, 1H, J=4.6, 11.7 Hz), 2.92–3.05 (m, 2H), 3.16–3.21 (m, 1H), 3.28(2, 2H), 3.42 (s, 3H), 4.16–4.22 (m, 2H), 7.12 (d, 2H, J=6.9 Hz), 7.23 (d, 2H, J=6.9 Hz).

6.5 Synthesis of (3S, 4S) Methyl 4-(4-Chlorophenyl)-1-(ethoxycarbonylmethyl) piperidine-3-carboxylate (Compound (−)-3)

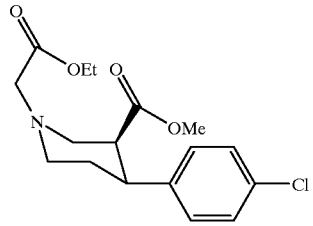

Prepared as described above from Compound (−)-2 to afford Compound (−)-3 (83%) as a waxy white solid: $R_f$ 0.6 (hexanes/EtOAc, 1:1); $[\alpha]_D$−42.3 (c 1.2, EtOH); MS m/z 339 (M$^+$), 266 (100); $^1$H NMR (CDCl$_3$) δ 1.29 (t, 3H, J=7.2 Hz), 1.82–1.87 (m, 1H), 2.55–2.72 (m, 2H), 2.76–2.91 (m, 2H), 3.00–3.04 (m, 2H), 3.23–3.42 (m, 3H), 3.56 (s, 3H), 4.16–4.22 (m, 2H), 7.26 (s, 4H); $^{13}$C NMR (CDCl$_3$) δ 14.2, 26.7, 41.2, 46.0, 51.3, 52.7, 55.1, 59.2, 60.4, 128.1, 129.1, 131.9, 141.5, 170.3, 172.3.

6.6 Synthesis of (3R, 4R) Methyl 4-(4-Chlorophenyl)-1-(ethoxycarbonylmethyl) piperidine-3-carboxylate (Compound (+)-3)

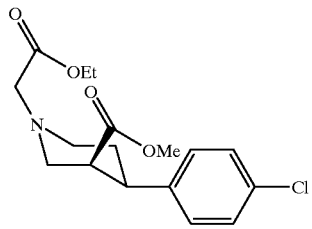

Prepared as described above from Compound (+)-2 to afford Compound (+)-3 as a white waxy solid: $[\alpha]_D$+37.5 (c 1.0, EtOH). Spectral data same as for (−)-3.

6.7 Synthesis of (4SR, 5SR)-4-(4-Chlorophenyl)-1-aza-bicyclo [3,2,1] octane-6-one (Compound (±)-4) and (4RS, 5SR) 4-(4-Chlorophenyl)-1-aza-bicyclo [3,2,1] octan-6-one (Compound (±)-5)

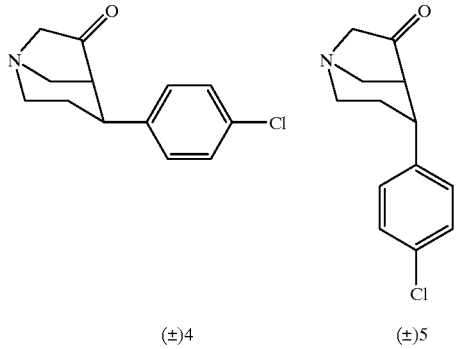

(±)4  (±)5

A solution of freshly dried EtOH (2.4 mL, 41 mmol) in toluene (20 mL) was carefully added to a suspension of 35% KH in mineral oil (4.7 g, 41 mmol) in toluene (30 mL). The resulting mixture was heated to reflux for 1 h and a solution of Compound (±)-3 in toluene (50 mL) was added and the flask was fitted with a Dean-Stark drying tube. The mixture was heated to reflux and the first 20 mL of solvents collected in the drying tube were removed. Reflux was continued for 4 h. The resulting suspension was cooled and washed with 10% HCl (2×100 mL). The pooled acid extracts were heated to reflux for 16 h and made basic with 10% NaOH. The crude product was extracted with $CH_2Cl_2$ (4×100 mL) and the extracts dried. Chromatography ($EtOAc/Et_3N$, 9:1) afforded Compound (+)-5 (660 mg, 17%) as a clear colorless oil: $R_f$ 0.15 ($EtOAc/Et_3N$, 9:1); $^1H$ NMR ($C_6D_6$) δ 1.13 (dd, 1H, J=4.4, 15.5 Hz), 1.63 (ddd, 1H, J=6.8, 13.6, 15.5 Hz), 1.91 (s, 1H), 2.39–2.49 (m, 2H), 2.62 (dd, 1H, J=3.1, 12.4 Hz), 2.79 (dd, 1H, J=3.2, 17.9 Hz), 2.85–3.05 (m, 3H), 7.29 (d, 2H, J=8.4 Hz), 7.37 (d, 2H, J=8.4 Hz); $^1H$ NMR ($CDCl_3$) δ 21.4, 40.2, 50.0, 52.2, 53.3, 61.5, 128.80, 128.84, 132/5. 140.4, 218.9.

Further elution afforded Compound (±)-4 (1.06 mg, 27%) as a clear colorless oil: $R_f$ 0.10 ($EtOAc/Et_3N$, 9:1); $^1H$ NMR ($C_6D_6$) β 1.06–1.11 (m, 1H), 1.32–1.47 (m, 1H), 1.91 (s, 1H), 2.41–2.50 (m, 2H), 2.59–2.66 (m, 2H), 2.74–2.90 (m, 2H), 6.91 (d, 2H, J=8.4 Hz), 7.16 (d, 2H, J=8.4 Hz); $^1H$ NMR ($C_6D_6$) β 16.6, 35.4, 37.8, 43.4, 49.8, 50.8, 117.9, 118.0, 121.9, 131.2, 206.8.

6.7.1 Resolution of Compound (±)-4 to Compound (-)-4 and Compound (+)-4

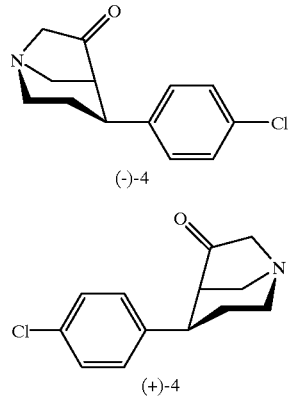

(-)-4

(+)-4

To a solution of Compound (±)-4 (1.0 g, 4.3 mmol) in EtOAc (50 mL) was added (1R)-(-)-10-camphorsulfonic acid (750 mg, 3.72 mmol). The resulting solution was stirred at rt for 16 h and the filtered. The white solids obtained were washed with EtOAc (10 mL) and suspended between satd. $NaHCO_3$ (50 mL) and EtOAc (75 mL). The organic layer was separated, washed with satd. $NaHCO_3$ (50 mL), brine (75 mL), dried ($Na_2SO_4$), and concentrated to afford (+)-4 as a white waxy solid: $[α]_D$+173 (c 1.1, $CHCl_3$). The combined mother liquors were similarly treated with (1S)-(+)-camphorsulfonic acid to afford Compound (-)-4 as a white waxy solid: $[α]_D$+162 (c 1.2, $CHCl_3$)

6.7.2 Resolution of Compound (±)-5 to Compound (-)-5 and Compound (+)-5

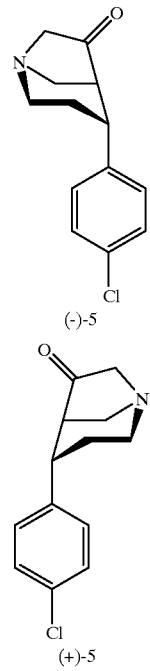

(-)-5

(+)-5

Crystalized as described above with dibenzoyl-1-tartaric acid to afford Compound (-)-5 as a clear colorless oil: $[α]_D$-9.2 (c 1.2, $CHCl_3$). The combined mother liquors were similarly treated with (1S)-(+)-camphorsulfonic acid to afford Compound (+)-5 as a white waxy solid: $[α]_D$+13 (c 1.2, $CHCl_3$).

6.8 Synthesis of (4R, 5R, 6R)-4-(4-Chlorophenyl)-1-azabicyclo [3.2.1] octan-6-ol (Compound (-)-6)

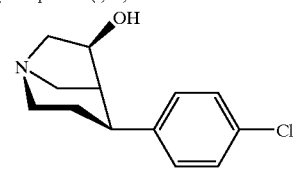

A 1M solution of DIBAL in hexanes (1.2 mL) was added dropwise to a solution of (-)-4 (140 mg, 0.59 mmol) in $CH_2Cl_2$ (20 mL) at -78° C. The resulting mixture was allowed to warm slowly to rt over 3 h. The reaction was quenched with satd. $NaHCO_3$ (ca 2 mL), stirred for 1 h, dried ($Na_2SO_4$) and filtered through celite. The solids obtained were washed with 10% MeOH in $CH_2Cl_2$ (100 mL) and the combined filtrates were concentrated to afford (-)-6 (138 mg, 97%) as a white solid: $[α]_D$-41 (c 1.0, EtOH); $R_f$ 0.2 ($MeOH/Et_3N$, 9:1); $^1H$ NMR ($CDCl_3$+ $CD_3OD$) δ 1.70 (brd, 1H, 13.2 Hz), 2.38 (s, 1H), 2.46–2.60 (m, 1H), 2.76 (s, 2H), 2.89–2.96 (m, 3H), 3.09 (dd, 1H, J=9.7, 17.0 Hz), 4.39–4.47 (m, 1H), 7.09–7.17 (m, 4H); $^{13}C$ NMR ($CDCl_3$+$CD_3OD$) δ 23.9, 43.4, 44.0, 54.4, 58.6, 60.1, 75.6, 127.7, 128.4, 131.0, 143.0.

6.9 Synthesis of (4S, 5S, 6S)-4-(4-Chlorophenyl)-1-azabicyclo [3.2.1] octan-6-ol (Compound (+)-6)

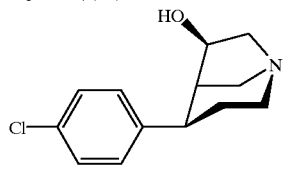

Prepared as described above from Compound (+)-4 to afford Compound (+)-6 (100%) as a white solid: [α]$_D$+43 (c 1.1, EtOH). Spectral data same as for (−)-6.

6.10 Synthesis of (4R, 5R, 6S)-4-(4-Chlorophenyl)-1-azabicyclo [3.2.1] octan-6-yl 3,4-methylenedioxyphenyl ether (Compound (+)-7))

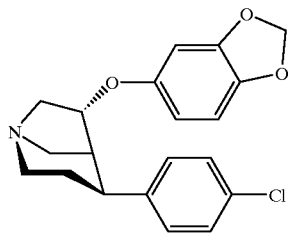

Methanesulfonyl chloride (110 mL, 1.5 mmol) was added dropwise to a solution of (−)-6 (130 mg, 0.548 mmol) in CH$_2$Cl$_2$ (10 mL) at 0° C. To this was added Et$_3$N and the resulting mixture was allowed to warm to rt over 3 h, diluted with ether (75 mL), washed with satd. NaHCO$_3$ (2×50 mL), water (50 mL), brine (50 mL), and dried (Na$_2$SO$_4$). The solvents were removed and the residue dried to afford 4α-(4-chlorophenyl)-1-azabicyclo[3.2.1]octan-6-yl methanesulfonate: R$_f$ 0.5 (MeOH/Et$_3$N, 9:1). A 0.5M solution of KHMDS in toluene (4.45 mL) was added to a solution of sesamol (345 mg, 2.50 mmol) in freshly distilled HMPA (2.5 mL). The resulting mixture was heated to 180° C. and the toluene was allowed to distill off. The resulting purple solution was cooled to rt and a solution of 4α-(4-chlorophenyl)-1-azabicyclo[3.2.1]octan-6-yl methanesulfonate in CH$_2$Cl$_2$ (5 mL) was added. The resulting mixture was slowly heated to 180° C. and the CH$_2$Cl$_2$ allowed to distill off. After 3 h at this temperature the resulting mixture was cooled, diluted with ether (75 mL), washed with satd. NaHCO$_3$ (50 mL), water (50 mL), brine (50 mL), and dried (Na$_2$SO$_4$). Chromatography (EtOAc/Et$_3$N, 9:1) afforded Compound (+)-7 (88 mg, 45%) as a white solid: [α]$_D$+4.0 (c 1.0, CHCl$_3$); R$_f$ 0.35 (EtOAc/Et$_3$N, 9:1); $^1$H NMR (C$_6$D$_6$) δ 0.75–0.94 (m, 2H), 1.83 (s, 1H), 2.06 (dd, 1H, J=3.4, 11.5 Hz), 2.22 (d, 1H, J=11.2 Hz), 2.27–2.44 (m, 2H), 2.65 (dd, 1H, J=5.0, 13.2 Hz), 2.79–2.84 (m, 2H), 3.78 (s, 1H), 4.97 (s, 1H), 5.03 (s, 1H), 5.45 (dd, 1H, J=2.2, 7.3 Hz), 5.81 (d, 1H, J=2.2 Hz), 6.17 (d, 1H, J=7.3 Hz), 6.41 (d, 2H, J=7.3 Hz), 7.20 (d, 2H, J=7.3 Hz); $^{13}$C NMR (C$_6$D$_6$) δ 13.2, 31.4, 36.4, 42.7, 48.4, 49.5, 67.5, 87.8, 90.3, 96.1, 97.3, 118.0, 118.1, 121.8, 131.5, 137.9, 142.6.

6.11 Synthesis of (4S, 5S, 6R)-4-(4-Chlorophenyl)-1-azabicyclo [3.2.1] octan-6-yl 3,4-methylenedioxyphenyl ether (Compound (−)-7))

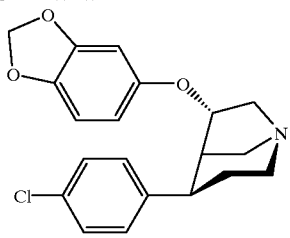

Prepared as described above from Compound (+)-6 to afford Compound (−)-7 (47%) as a white solid: [α]$_D$−3.6 (c 1.1, CHCl$_3$). Spectral data same as for (+)-7.

6.12 Synthesis of (4R, 5R)-4-(4-Chlorophenyl)-1-aza-bicyclo [3,2,1] octan-6-one O-methyl-oxime (Compound (−)-8))

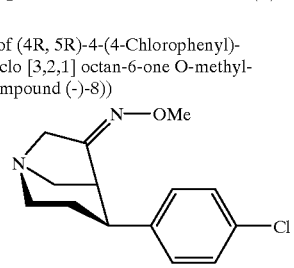

A solution of Compound (−)-4 (26 mg, 0.11 mmol) and methoxylamine hydrochloride (26 mg, 0.33 mmol) in absolute EtOH (5 mL) was heated to reflux. After 4 h the reaction mixture was cooled diluted with ether (25 mL) and 10% NH$_4$OH (25 mL). The ether layer was separated and washed with water (25 mL), brine (25 mL) and dried (Na$_2$SO$_4$). PTLC (EtOAc/Et$_3$N, 9:1) to afford Compound trans-(−)-8 (16.5 mg, 57%, 42:1, trans/cis by GC/MS) as a waxy solid: R$_f$0.15 (EtOAc/Et$_3$N, 9:1); [α]$_D$−21.8 (c 0.83, CHCl$_3$); MS 264 (M$^+$, 9), 233 (100); $^1$H NMR (CDCl$_3$) δ 1.61 (d, 1H, J=13.2 Hz), 1.92 (m, 1H), 2.72 (s, 1H), 3.02–3.11 (m, 5H), 3.52–3.54 (m, 2H), 3.80 (s, 3H), 7.18–7.28 (m, 4H); $^{13}$C NMR (CDCl$_3$) δ 25.4, 44.4, 46.1, 53.8, 54.3, 61.6, 61.7, 128.4, 128.8, 132.3, 141.5, 164.3. Toluenesulfonate salt as a white solid: mp=154–155° C.; $^1$H NMR (CDCl$_3$) δ 2.07–2.13 (m, 2H), 2.38 (s, 3H), 3.19 (s, 1H), 3.29 (dd, 1H, J=6.6, 10.7 Hz), 3.62–3.70 (m, 1H), 3.73–3.83 (m, 4H), 3.87 (s, 3H), 4.01 (d, 1H, J=17.6 Hz), 4.42 (dd, 1H, J=4.1, 17.6 Hz), 7.18–7.24 (m, 4H), 7.34 (d, 2H, J=8.5 Hz), 7.81 (d, 2H, J=8.1 Hz).

The cis (−)-8 isomer was obtained as a crude mixture containing 35% of trans-(−)-8 (5.0 mg, 17%) as a clear colorless oil; R$_f$0.11 (EtOAc/Et$_3$N, 9:1); [α]$_D$−67.6 (c 0.23, CHCl$_3$); $^1$H NMR (CDCl$_3$) δ 1.74–2.21 (m, 2H), 2.45 (s, 1H), 3.03–3.26 (m, 5H), 3.35–3.55 (m, 2H), 5.28 (s, 3H), 7.14–7.28 (m, 4H); $^{13}$C NMR (CDCl$_3$) δ 24.5, 44.1, 45.7, 54.4, 55.2, 60.6, 61.2, 127.9, 128.5, 132.3, 142.2, 165.7. Toluenesulfonate salt as a waxy white solid: $^1$H NMR (CDCl$_3$) δ 2.07–2.13 (m, 2H), 2.38 (s, 3H), 3.19 (s, 1H), 3.29 (dd, 1H, J=6.6, 10.7 Hz), 3.62–3.70 (m, 1H), 3.73–3.83 (m, 4H), 3.87 (s, 3H), 4.01 (d, 1H, J=17.6 Hz), 4.42 (dd, 1H, J=4.1, 17.6 Hz), 7.18–7.24 (m, 4H), 7.34 (d, 2H, J=8.5 Hz), 7.81 (d, 2H, J=8.1 Hz).

6.13 Synthesis of (4S, 5S)-4-(4-Chlorophenyl)-1-aza-bicyclo [3.2.1] octan-6-one O-methyl-oxime (Compound (+)-8))

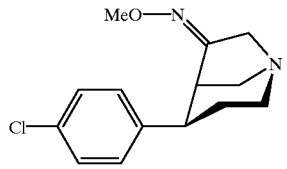

Prepared as described above from Compound (+)-4 to afford Compound (+)-8 as a white waxy solid: $[\alpha]_D$ −26 (c 1.4, CHCl$_3$). Spectral data same as for (−)-8.

6.14 Synthesis of (4R, 5S)-4-(4-Chlorophenyl)-1-aza-bicyclo [3.2.1] octan-6-one O-methyl-oxime (Compound (−)-13))

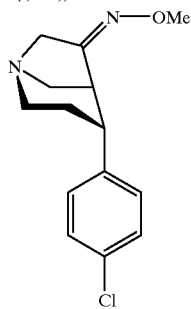

Prepared as described above from Compound (−)-5 to afford trans-(−)-13 (20.9 mg, 40%) as a clear colorless oil, and cis-(−)-13 (10 mg, 19%) as a clear colorless oil: trans-(−)-13: R$_f$ 0.5 (EtOAc/Et$_3$N, 9:1); $[\alpha]_D$ −46 (c 1.0, CHCl$_3$); MS 264 (M$^+$,9), 233 (100); $^1$H NMR (CDCl$_3$) δ 1.76 (dd, 1H, J=4.5, 15.5 HZ), 2.18 (M, 1H), 2.64 (DD, 1H, J=3.3, 12.1 HZ), 2.79 (DD, 1H, J=3.3, 3.8 Hz), 2.87 (dd, 1H, J=2.8, 12.4 Hz), 2.92 (dd, 1H, J=6.3, 14.2 Hz), 3.23–3.34 (m, 2H), 3.56 (d, 1H, J=18.3 Hz), 3.67 (dd, 1H, J=2.8, 18.3 Hz), 3.89 (s, 3H), 7.26 (m, 4H). $^{13}$C NMR (CDCl$_3$) δ 20.8, 42.5, 44.6, 52.2, 53.8, 54.0, 61.7, 128.7, 128.9, 132.1, 140.9, 165.5. Cis-(−)-13: R$_f$ 0.3 (EtOAc/Et$_3$N, 9:1); $[\alpha]_D$ −36(c 0.24, CHCl$_3$); MS 264 (M$^+$, 9), 233 (100); $^1$H NMR (CDCl$_3$) δ 1.86 (dd, 1H, J=4.7, 15.5 HZ), 2.24 (M, 1H), 2.71 (dd, 1H, J=3.3, 12.1 Hz), 2.95 (dd, 1H, J=2.4, 12.1 Hz), 3.06 (dd, 1H, J=6.3, 13.9 Hz), 3.32–3.43 (m, 2H), 3.56–3.78 (m, 3H), 3.95 (s, 3H), 7.32 (m, 4H). $^{13}$C NMR (CDCl$_3$) δ 21.0, 38.4, 42.4, 52.5, 53.9, 55.4, 61.9, 128.7, 129.0, 132.1, 140.9, 163.9;

6.15 Synthesis of (4S, 5R) 4-(4-Chlorophenyl)-1-aza-bicyclo [3.2.1] octan-6-one O-methyl-oxime (Compound (+)-13))

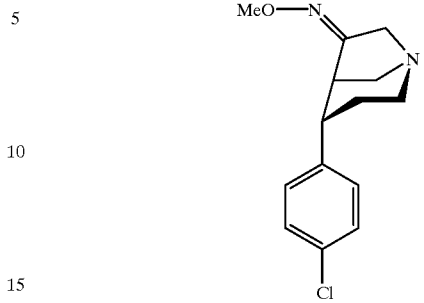

Prepared as described above from Compound (+)-5 to afford trans-(+)-13 as a clear colorless oil, and cis-(+)-13 as a clear colorless oil: trans-(+)-13: $[\alpha]_D$ +25 (c 0.76, CHCl$_3$). Cis-(+)-13: $[\alpha]_D$ +44 (c 0.24, CHCl$_3$).

6.16 Synthesis of (3SR, 4SR) Methyl 1-(2-chloroethyl)-4-(4-chlorophenyl)piperidine-3-carboxylate (Compound 16)

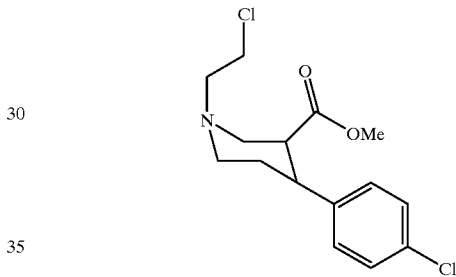

A suspension of Compound 2 (8.0 g, 32 mmol), 1-bromo-2-chloroethane (5.2 mL, 63 mmol), and K$_2$CO$_3$ (6.5 g, 47 mmol) in acetone (150 mL) was stirred at rt for 18 h. The solvents were removed and the resulting residue was suspended in water (200 mL) and extracted with ether (250 mL). The organic layer was separated and washed with satd. NaHCO$_3$ (200 mL), water (200 mL), brine (200 mL) and concentrated. Chromatography (hexanes/EtOAc/Et$_3$N, gradient) afforded Compound 16 (3.2 g, 32%) as a clear colorless oil: R$_f$ 0.35 (hexanes/EtOAc, 2:1); MS m/z 315 (M$^+$, 1.5), 266 (100); $^1$H NMR (CDCl$_3$) δ 1.81–1.88 (m, 2H), 2.26–2.34 (m, 2H), 2.38 (t, 1H, J=10.8 Hz), 2.81 (t, 2H, J=6.8 Hz), 2.82–2.97 (m, 2H), 3.04 (brd, 1H, J=11.2 Hz), 3.20 (brd, 1H, J=11.2 Hz), 3.46 (s, 3H), 3.61 (t, 2H, J=6.8 Hz), 7.13 (d, 2H, J=8.6 Hz), 7.27 (d, 2H, J=8.6 Hz); $^{13}$C NMR (CDCl$_3$) δ 32.8, 40.9, 44.3, 48.8, 51.5, 53.5, 56.0, 59.5, 128.5, 128.6, 132.2, 141.7, 173.1. Further elution afforded recovered Compound 2 (4.5 g, 56%) as a yellow oil.

6.17 Synthesis of (4RS, 5SR)-4-(4-Chlorophenyl)-5-methoxycarbonyl-1-azabicyclo [3.2.1] octane (Compound 17)

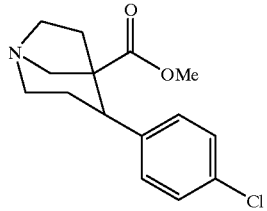

A suspension of Compound 16 (850 mg, 2.69 mmol), KI (166 mg, 1.0 mmol), and $K_2CO_3$ (370 mg, 2.69 mmol) in acetone (150 mL) was stirred at reflux for 18 h. The solvents were removed and the resulting residue was suspended in water (50 mL) and extracted with EtOAc (100 mL). The organic layer was separated and washed with satd. $NaHCO_3$ (50 mL), water (50 mL), brine (50 mL) and concentrated. Chromatography (EtOAc) to afford Compound 17 (440 mg, 58%) as a clear colorless oil: $R_f$ 0.15 (EtOAc); MS m/z 266 (100); $^1$H NMR ($CDCl_3$) δ 1.76–1.83 (m, 2H), 2.15–2.30 (m, 2H), 2.62 (s, 2H), 2.74–2.94 (m, 2H), 3.04 (d, 1H, J=11.2 Hz), 3.19 (d, 1H, J=9.8 Hz), 3.45 (s, 3H), 3.90 (m, 1H), 7.13 (d, 2H, J=8.3 Hz), 7.24 (d, 2H, J=8.3 Hz); $^{13}$C NMR ($CDCl_3$) δ 14.0 32.8, 44.2, 48.7, 51.2, 54.9, 54.6, 56.4, 128.4, 128.5, 132.0, 141.7, 173.5.

6.18 Synthesis of (1SR, 5SR, 6RS)-6-[(2'-bromoally)-7-ethoxycarbonyl-3-(p-tolyl)-8-azabicyclo [3.2.1] oct-2-en-3-one] (Compound 26β) and (1SR, 5SR, 6SR) 6-[(2'-bromoallyl)-7-ethoxycarbonyl-3-(p-tolyl)-8-azabicyclo [3.2.1] oct-2-en-3-one] (Compound 26α)

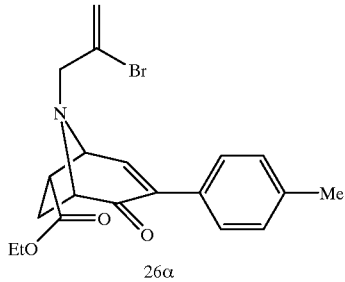

26α

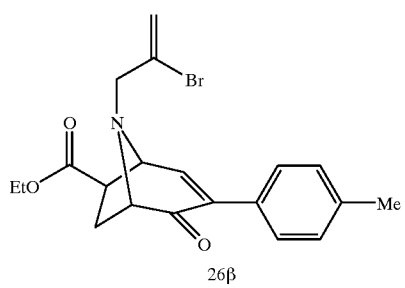

26β

A mixture of N-(2'-bromoallyl)-3-hydroxy-4-(p-tolyl) pyridinium bromide (11 g, 27 mmol), $Et_3N$ (7.5 mL, 54 mL) and hydroquinone (100 mg) in ethyl acrylate was heated to reflux for 1.5 h, cooled and diluted with ether (200 mL). The resulting suspension was filtered and the solids were washed with ether (100 mL). The combined filtrates were concentrated and subjected to chromatography (hexanes/EtOAc, 4:1) to afford Compound 26β (5.5 g, 52%) as a yellow oil:

$R_f$ 0.55 (hexanes/EtOAc, 4:1); $^1$H NMR ($CDCl_3$) δ 1.32 (t, 3H, J=7.2 Hz), 2.01 (dd, 1H, J=5.9, 13.8 Hz), 2.36 (s, 3H), 2.96 (ddd, 1H, J=4.3, 7.8, 13.8 Hz), 3.01 (dd, 1H, J=4.3, 9.3 Hz), 3.54 (s, 2H), 3.84 (d, 1H, J=7.8 Hz), 4.23 (m, 2H), 4.36 (d, 1H, J=5.1 Hz), 5.58 (s, 1H), 5.90 (s, 1H), 7.05 (d, 1H, J=5.1 Hz), 7.18 (d, 2H, J=8.1 Hz), 7.31 (d, 2H, J=8.1 Hz); 13C NMR ($CDCl_3$) δ 14.2, 21.1, 27.7, 47.1, 56.0, 60.6, 61.4, 68.9, 118.0, 128.0, 128.9, 129.6, 130.8, 138.2, 138.3, 143.0, 172.4, 197.0.

Further elution afforded Compound 26α (3.1 g, 29.1%) as a yellow oil: $R_f$ 0.50 (hexanes/EtOAc, 4:1); $^1$H NMR ($CDCl_3$) δ 1.26 (t, 3H, J=7.2 Hz), 2.11 (dd, 1H, J=5.9, 14.1 Hz), 2.35 (s, 3H), 2.51–2.67 (m, 1H), 3.46 (m, 2H), 3.51–2.63 (m, 1H), 3.78 (d, 1H, J=7.5 Hz), 4.16 (q, 2H, J=7.2 Hz), 4.27 (t, 1H, J=5.2 Hz), 5.60 (s, 1H), 5.84 (s, 1H), 6.94 (d, 1H, J=5.2 Hz), 7.17 (d, 2H, J=8.0 Hz), 7.26 (d, 2H, J=8.0 Hz).

6.19 Synthesis of (1RS, 2SR, 4RS, 6RS, 7SR)-6-Ethoxycarbonyl-10-methylene-2-(p-tolyl)-8-azatricyclo [5.2.0.0$^{4,8}$] decan-3-one (Compound 27β)

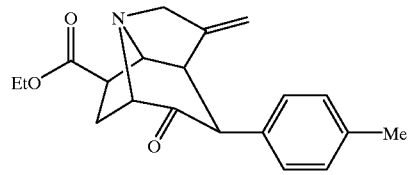

A solution of Compound 26β (3.8 g, 9.7 mmol), 2,2'-azobis(2-methylpropiononitrile) (AIBN) (1.26 g, 7.7 mmol), and n-$Bu_3$SnH (5.0 mL, 19.1 mmol) in benzene (50 mL) was heated to reflux for 6 h, cooled and concentrated. The resulting oil was chromatographed (hexanes.EtOAc, gradient 4:1 to 1:1) to afford Compound 27β (1.6 g, 49%) as a clear colorless oil: $R_f$ 0.17 (hexanes/EtOAc, 1:1); $^1$H NMR ($CDCl_3$) δ 1.30 (t, 3H, J=7.1 Hz), 2.16 (dd, 1H, J=9.6, 14.1 Hz), 2.33 (s, 3H), 2.76 (dd, 1H, J=6.7, 14.1 Hz), 2.96 (t, 1H, J=3.7 Hz), 3.54 (dd, 1H, J=6.7, 9.6 Hz), 3.68–3.75 (m, 3H), 3.94 (m, 2H), 4.25 (q, 2H, J=7.1 Hz), 4.47 (s, 1H), 4.93 (s, 1H), 6.97–7.18 (m, 4H); $^{13}$C NMR ($CDCl_3$) δ 14.2, 21.0, 33.2, 42.4, 52.9, 54.5, 56.7, 61.7, 73.8, 75.9, 128.4, 129.9, 132.0, 136.8, 147.7, 173.5, 210.8.

6.20 Synthesis of (1RS, 2SR, 4RS, 6SR, 7SR)-6-Ethoxycarbonyl-10-methylene-2-(p-tolyl)-8-azatricyclo [5.2.0.0$^{4,8}$] decan-3-one (Compound 27α)

Prepared as described above from Compound 26α to afford Compound 27α as a clear colorless oil: $R_f$ 0.10 (hexanes/EtOAc, 1:1); $^1$H NMR ($CDCl_3$) δ 1.37 (t, 3H, J=6.9 Hz), 2.30 (s, 3H), 2.36 (dd, 1H, J=4.7, 14.4 Hz), 2.63 (ddd, 1H, J=7.5, 12.1, 14.4 Hz), 3.05 (t, 1H, J=3.3 Hz), 3.64–3.78 (m, 4H), 3.87 (dd, 1H, J=3.2, 7.0 Hz), 4.04 (d, 1H, J=3.3 Hz), 4.25–4.41 (m, 2H), 4.47 (s, 1H), 4.92 (s, 1H), 6.94 (d, 2H, J=8.0 Hz), 7.08 (d, 2H, J=8.0 Hz); $^{13}$C NMR ($CDCl_3$) δ 14.4, 21.0, 31.7, 43.2, 52.7, 53.6, 56.4, 61.4, 68.3, 73.1, 109.8, 128.4, 129.8, 132.0, 136.7, 147.3, 172.8, 210.0.

6.21 Synthesis of (1RS, 2SR, 4RS, 6RS, 7RS)-6-Ethoxycarbonyl-10-methylene-2-(p-tolyl)-8-azatricyclo[5.2.0.0^{4,8}]decan-3-ol
(Compound 28β)

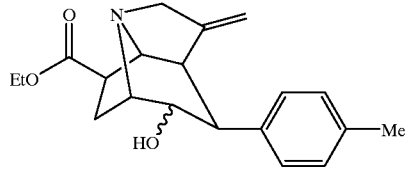

NaBH$_4$ (175 mg, 4.6 mmol) was added portionwise to a solution of Compound 27β (1.5 g, 4.6 mmol) in EtOH (25 mL). After 1 h at rt, the reaction was quenched with 10% NH$_4$Cl (100 mL) and extracted with CH$_2$Cl$_2$ (3×100 mL). Chromatography (EtOAc/Et$_3$N, 9:1) afforded Compound 28β (1.3 g, 86%) as a mixture of isomers (2:1 by NMR): R$_f$ 0.4 (EtOAc/Et$_3$N, 9:1); $^1$H NMR (CDCl$_3$, major isomer) δ 1.30 (t, 3H, J=7.4 Hz), 1.95 (s, 1H), 2.06 (dd, 1H, J=4.7, 13.8 Hz), 2.33 (s, 3H), 47-2.54 (m, 1H), 2.89 (s, 1H), 3.43–3.72 (m, 5H), 3.82 (s, 1H), 4.07–4.29 (m, 2H), 4.41 (d, 1H, J=11.0 Hz), 4.93 (s, 1H), 5.07 (s, 1H), 7.11 (d, 2H, J=8.4 Hz), 7.39 (d, 2H, J=8.4 Hz).

6.22 Synthesis of (1RS, 2SR, 4RS, 6SR, 7SR)-6-Ethoxycarbonyl-10-methylene-2-(p-tolyl)-8-azatricyclo[5.2.0.0^{4,8}]decan-3-ol
(Compound 28α)

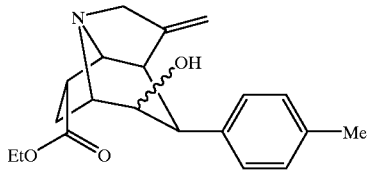

Prepared as described above from Compound 27α to afford Compound 28α as a clear colorless oil: R$_f$ 0.15 (EtOAc/Et$_3$N, 9:1); $^1$H NMR (CDCl$_3$) δ 1.24 (t, 3H, J=7.2 Hz), 1.84 (s, 1H), 2.13 (m, 1H), 2.33 (s, 3H), 2.54 (m, 1H), 2.96 (s, 1H), 3.14 (s, 1H), 3.41–3.52 (m, 2H), 3.61–3.67 (m, 2H), 3.83 (s, 1H), 4.04–4.34 (m, 2H), 4.46 (m, 1H), 4.93 (s, 1H), 5.05 (s, 1H), 7.14 (d, 2H, J=8.1 Hz), 7.35 (d, 2H, J=8.1 Hz).

6.23 Synthesis of (1RS, 2SR, 4RS, 6RS, 7SR)-6-Ethoxycarbonyl-10-methylene-2-(p-tolyl)-8-azatricyclo[5.2.0.0^{4,8}]decane
(Compound 29β)

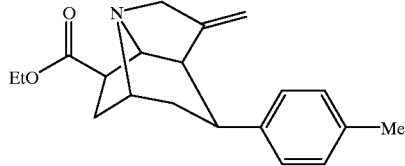

A 1M solution of LiHMDS in THF (4.0 mL) was added dropwise to a solution of Compound 28β (1.3 g, 4.0 mmol) in THF (50 mL) at −78° C. After 15 min at this temperature phenyl chlorothionoformate (1.1 mL, 7.94 mmol) was added and the resulting mixture was allowed to warm to rt over 90 min. This mixture was then diluted with satd. NaHCO$_3$ (100 mL) and extracted with EtOAc (100 mL). The organic layer was washed with water (100 mL), brine (100 mL), and concentrated. Chromatography (hexanes/EtOAc, gradient 2:1 to 0:1) afforded 6β-ethoxycarbonyl-10-methylene-2-(p-tolyl)-8-azatricyclo[5.2.0.0^{4,8}]decan-3-yl phenyl thionocarbonate (720 mg, 30%) as a clear colorless oil: R$_f$ 0.1 (hexanes/EtOAc, 1:1); $^1$H NMR (CDCl$_3$) δ 1.31 (t, 3H), 2.10 (dd, 1H), 2.37 (s, 3H), 2.75 (m, 1H), 2.80 (m, 1H), 3.22 (dd, 1H), 3.46 (m, 1H), 3.60 (m, 1H), 3.77 (d, 1H), 3.88 (d, 1H), 4.08 (m, 2H), 4.90 (s, 1H), 5.00 (s, 1H), 5.56 (d, 1H), 6.91 (m, 2H), 7.16 (m, 2H), 7.27–7.38 (m, 5H).

The above product, (700 mg, 1.5 mmol), AIBN (270 mg, 1.7 mmol) and n-Bu$_3$SnH (1.1 mL, 4.2 mmol) in benzene (50 mL) was heated to reflux for 2 h and the solvents were removed. The residual oil was chromatographed to afford Compound 29β (440 mg, 93%) as a clear colorless oil: R$_f$ 0.5 (EtOAc/Et$_3$N, 9:1); $^1$H NMR (CDCl$_3$) δ 1.31 (t, 3H, J=7.1 Hz), 1.42 (dd, 1H, J=4.5, 13.5 Hz), 1.98–2.09 (m, 2H), 2.34 (s, 3H), 2.61–2.69 (m, 2H), 3.18 (m, 1H), 3.30 (dd, 1H, J=6.3, 9.8 Hz), 3.54–3.59 (m, 3H), 3.74 (d, 1H, J=4.0 Hz), 4.25 (q, 2H, J=7.1 Hz), 4.27 (s, 1H), 4.80 (s, 1H), 7.05–7.14 (m, 4H); $^{13}$C NMR (CDCl$_3$) δ 14.3, 20.9, 28.8, 35.0, 38.4, 42.7, 52.3, 53.0, 60.7, 61.0, 70.0, 106.5, 127.7, 128.6, 135.7, 139.0, 149.1, 174.7.

6.24 Synthesis of (1RS, 2SR, 4RS, 6SR, 7SR)-6-Ethoxycarbonyl-10-methylene-2-(p-tolyl)-8-azatricyclo[5.2.0.0^{4,8}]decane
(Compound 29α)

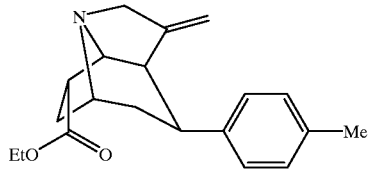

(1RS, 2SR, 4RS, 6SR, 7SR)-6-ethoxycarbonyl-10-methylene-2-(p-tolyl)-8-azatricyclo [5.2.0.0^{4-8}] decan-3-yl phenyl thiocarbonate was prepared from Compound 28α as described in the previous Example. The product was obtained as a clear colorless oil:

R$_f$ 0.2 (EtOAc); $^1$H NMR (CDCl$_3$) δ 1.30 (t, 3H), 2.29 (dd, 1H), 2.36 (s, 3H), 2.63 (m, 1H), 2.87 (s, 1H), 3.42 (dd, 1H), 3.55 (m, 1H), 3.61 (m, 1H), 3.71 (d, 1H), 3.86 (d, 1H), 4.12 (d, 2H) , 4.27 (m, 2H), 4.91 (s, 1H), 5.54 (s, 1H), 6.94 (d, 2H) 7.13 (d, 2H), 7.26 (m, 2H), 7.36 (m, 3H).

The 6α-ethoxycarbonyl-10-methylene-2-(p-tolyl)-8-azatricyclo[5.2.0.0^{4,8}]decan-3-yl phenyl thionocarbonate was reacted with a 1M solution of LiHMDS as described in the previous Example to afford Compound 29α as a clear colorless oil: R$_f$ 0.4 (EtOAc/Et$_3$N, 9:1); $^1$H NMR (CDCl$_3$) δ 1.38 (t, 3H, J=7.1 Hz), 1.44 (m, 1H), 2.05 (ddd, 1H, J=3.2, 10.0, 13.0 Hz), 2.21 (dd, 1H, J=5.0, 13.4 Hz), 2.33 (s, 3H), 2.56 (ddd, 1H, J=7.0, 12.0, 13.4 Hz), 2.76 (m, 1H), 3.10 (m, 1H), 3.50–3.59 (m, 4H), 3.67 (m, 1H), 4.25 (s, 1H), 4.27–4.39 (m, 2H), 4.79 (s, 1H), 6.98 (d, 2H, J=8.0 Hz), 7.09 (d, 2H, J=8.0 Hz); $^{13}$C NMR (CDCl$_3$) δ 14.5, 21.0, 29.4, 32.7, 37.5, 43.3, 51.5, 53.1, 60.3, 60.9, 68.4, 106.3, 127.6, 128.5, 135.8, 139.1, 148.6, 173.7.

6.25 Synthesis of (1RS, 2SR, 4RS, 6RS, 7SR)-6-
Hydroxymethyl-10-methylene-2-(p-tolyl)-8-
azatricyclo[5.2.0.0$^{4,8}$]decane
(Compound 30β)

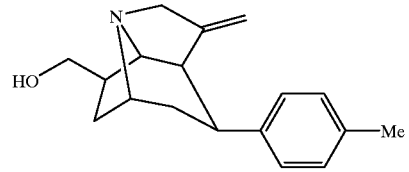

Lithium aluminum hydride (98 mg, 2.6 mmol) was added portionwise to a solution of Compound 29β (400 mg, 1.3 mmol) in ether (10 mL). After 30 min at rt the reaction was carefully quenched with satd. NaHCO$_3$ (50 mL) and extracted with ether (100 mL). The organic layer was washed with water (50 mL), brine (50 mL), dried (Na$_2$SO$_4$), and concentrated. The residual oil was chromatographed (EtOAc/i-PrOH/Et$_3$N, gradient, 9:0:1 to 4:4:1) to afford Compound 30β (160 mg, 45%) as a clear colorless oil: R$_f$ 0.2 (EtOAc/i-PrOH/Et$_3$N, 4:4:1); $^1$H NMR (CDCl$_3$) δ 1.41 (dd, 1H, J=4.4, 13.7 Hz), 1.89–2.06 (m, 3H), 2.31 (s, 3H), 2.55 (s, 1H), 2.67 (m, 1H), 3.25 (m, 1H), 3.33 (d, 1H, J=4.2 Hz), 3.47 (s, 1H), 3.55 (s, 1H), 3.64–3.77 (m, 3H), 4.23 (s, 1H), 4.76 (s, 1H), 4.76 (s, 1H), 7.05 (m, 4H); $^{13}$C NMR (CDCl$_3$) δ 20.9, 29.1, 34.6, 38.3, 39.7, 52.5, 52.9, 60.8, 66.6, 70.4, 106.3, 127.6, 128.5, 139.3, 149.3.

6.26 Synthesis of (1RS, 2SR, 4RS, 6SR, 7SR)-6-
Hydroxymethyl-10-methylene-2-(p-tolyl)-8-
azatricyclo[5.2.0.0$^{4,8}$]decane
(Compound 30α)

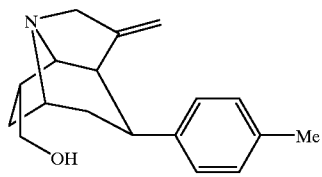

Prepared as described above from Compound 29α to afford Compound 30α as a clear colorless oil: R$_f$ 0.2 (EtOAc/i-PrOH/Et$_3$N, 4:4:1); $^1$H NMR (CDCl$_3$) δ 1.41 (dd, 1H, J=4.8, 13.7 Hz), 1.51 (dd, 1H, J=6.3, 13.2 Hz), 2.06 (ddd, 1H, J=3.1, 11.2, 13.9 Hz), 2.34 (s, 3H), 2.53 (ddd, 1H, J=7.5, 12.0, 13.2 Hz), 2.68 (s, 1H), 2.91 (m, 1H), 3.39–3.44 (m, 2H), 3.57 (m, 3H), 4.07–4.14 (m, 2H), 4.21 (s, 1H), 4.75 (s, 1H), 4.76 (s, 1H), 7.08 (m, 4H); $^{13}$C NMR (CDCl$_3$) δ 20.9, 29.4, 33.8, 37.6, 42.0, 50.6, 52.4, 60.1, 62.6, 68.8, 106.3, 127.6, 128.5, 135.6, 139.1, 149.3.

6.27 Synthesis of (1RS, 2SR, 4RS, 6SR, 7SR)-10-
Methylene-6-methyl-2-(p-tolyl)-8-
azatricyclo[5.2.0.0$^{4,8}$]decane
(Compound 31β)

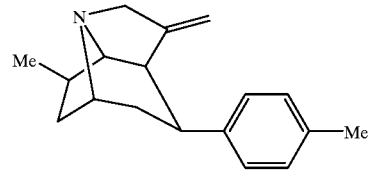

A 1M solution of LiHMDS in THF (360 μl) was added dropwise to a solution of Compound 30β (94 mg, 0.33 mmol) in THF (10 mL) at −78° C. After 15 min at this temperature phenyl chlorothionoformate (100 μl, 0.725 mmol) was added and the resulting mixture was allowed to warm to rt over 90 min. This mixture was then diluted with satd. NaHCO$_3$ (25 mL) and extracted with EtOAc (25 mL). The organic layer was washed with water (25 mL), brine (25 mL), and concentrated. Chromatography (EtOAc/Et$_3$N, gradient 1:0 to 9:1) afforded 10-methylene-6β-(phenoxythiocarboxymethyl)-2-(p-tolyl)-8-azatricyclo [5.2.0.0$^{4,8}$]decane (110 mg, 80%) as a clear colorless oil. R$_f$ 0.6 (EtOAc/Et$_3$N, 9:1); $^1$H NMR (CDCl$_3$) δ 1.51 (dd, 1H, J=4.6, 14.0 Hz), 1.99–2.13 (m, 3H), 2.32 (s, 3H), 2.68 (s, 1H), 3.04 (m, 1H), 3.27 (m, 1H), 3.55 (d, 1H, J=3.8 Hz), 3.69 (m, 3H), 4.29 (s, 1H), 4.63 (m, 2H), 4.84 (m, 1H), 7.04–7.15 (m, 5H), 7.29 (m, 1H), 7.40 (m, 2H); $^{13}$C NMR (CDCl$_3$) δ 20.9, 28.6, 34.4, 36.1, 38.0, 52.1, 52.3, 60.8, 69.8, 76.4, 107.8, 121.9, 126.5, 127.6, 128.7, 129.5, 135.9, 138.2, 146.7, 153.3, 194.7.

The above product (90 mg, 0.22 mmol), AIBN (40 mg, 0.24 mmol) and n-Bu$_3$SnH (160 μl, 0.61 mmol) in benzene (10 mL) were heated to reflux for 2 h and the solvents were removed. The residual oil was chromatographed to afford Compound 31β (41 mg, 74%) as a clear colorless oil: R$_f$ 0.3 (EtOAc/Et$_3$N, 9:1); $^1$H NMR (CDCl$_3$) δ 1.28 (d, 3H, J=6.9 Hz), 1.39 (dd, 1H, J=6.0, 13.8 Hz), 1.81–1.89 (m, 1H), 1.97–2.10 (m, 2H), 2.38 (s, 3H), 2.56–2.64 (m, 2H), 3.13 (d, 1H, J=3.9 Hz), 3.26–3.34 (m, 1H), 3.57 (s, 1H), 3.62 (s, 2H), 4.27 (s, 1H), 4.81 (s, 1H), 7.09–7.24 (m, 4H); $^{13}$C NMR (CDCl$_3$) δ 20.9, 23.4, 29.0, 31.9, 38.4, 40.8, 52.8, 53.1, 61.9, 75.0, 105.8, 127.7, 128.5, 135.4, 139.7, 150.3.

6.28 Resolution of (1RS, 2SR, 4RS, 7RS)-10-
Methylene-2-(p-tolyl)-8-azatricyclo[5.2.0.0$^{4,8}$]
decane (Compound (±)-40) to yield Compound
(−)-40 and Compound (+)-40

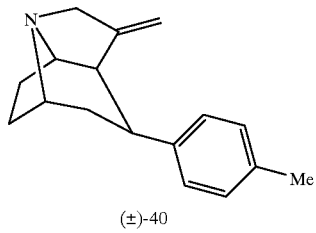

(±)-40

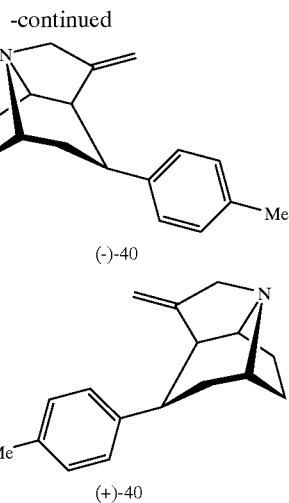

(−)-40

(+)-40

A solution of Compound (±)-40 (126 mg, 0.526 mmol; prepared as described in Smith et al., 1998, Tetrahedron Lett. 39:197–200) in EtOAc (5 mL) was added to a solution of (1S)-(+)-10-camphorsulfonic acid in EtOAc (5 mL). The resulting solution was stirred for 30 min at rt and then cooled to −10° C. The crystals obtained were recryatallized from EtOAc, dissolved in EtOAc (75 mL) and washed with satd. $NaHCO_3$ (2×25 mL), water (25 mL) and brine (25 mL) and dried ($Na_2SO_4$). The solvents were removed to afford Compound (−)-40 as a white waxy solid. $[\alpha]_D$ −14.0 (c=3.2, $CHCl_3$), 95% ee by HPLC. Anal. $[C_{17}H_{21}N.1.08C_7H_8O_3S]$ calcd: C 68.82, H 6.99, N 3.30; found: C 68.77, H 6.91, N 3.14.

The pooled mother liquors were dissolved in EtOAc (75 mL) and washed with sat $NaHCO_3$ (2×25 mL), water (25 mL) and brine (25 mL) and dried ($Na_2SO_4$). The resulting residue was resolved similarly using (1R)-(−)-10-camphorsulfonic acid to afford Compound (+)-40 as a white waxy solid. $[\alpha]_D$ +15.8 (c 2.9, $CHCl_3$), >98% ee by HPLC. Anal. $[C_{17}H_{21}N.1.13C_7H_8O_3S]$ calcd: C 68.07, H 6.87, N 3.08; found: C 68.06, H 6.75, N 3.09.

6.29 Synthesis of 1-(2-Bromobenzyl)-3-hydroxy-4-(p-tolyl)pyridinium bromide (Compound 43)

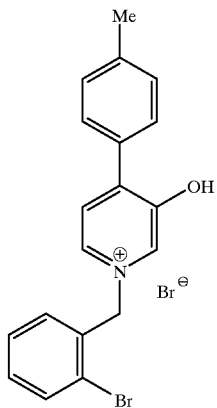

A solution of 3-hydroxy-4-(p-tolyl)pyridine (2.5 g, 13 mmol) and 2-bromobenzyl bromide (14 g, 54 mmol) in THF (10 mL) was heated to reflux for 20 h. The resulting mixture was cooled, diluted with EtOAc (100 mL) and stirred for 30 min. The suspension was filtered and the solids were washed with EtOAc (2×25 mL) and dried to afford Compound 43 (5.7 g, 97%) as a white solid: mp 199–201° C.; $^1$H NMR (DMSO-$d_6$) δ 2.40 (s, 3H), 6.01 (s, 2H), 7.37–7.59 (m, 5 H), 7.70–7.81 (m, 3H), 8.18 (d, 1H, J=6.1 Hz), 8.52 (s, 1H), 8.77 (d, 1H, J=6.1 Hz); $^{13}$C NMR (DMSO-$d_6$) δ 21.5, 62.9, 124.2, 127.9, 129.2, 129.8, 129.9, 130.0, 132.1, 132.2, 133.5, 133.9, 136.8, 141.1, 143.8, 154.1.

6.30 Synthesis of (1RS, 2SR, 4RS, 6RS, 7SR)-6-Benzenesulfonyl-10,11-benzeno-2-(p-tolyl)-8-azatricyclo[5.4.0.0$^{4,8}$]undecan-3-one (Compound 44)

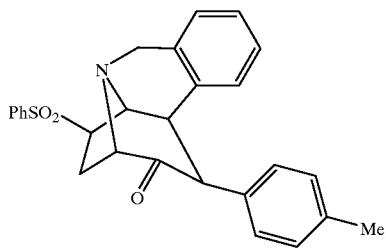

A mixture of Compound 43 (8.40 g, 19.3 mmol), triethylamine (8.1 mL, 58 mmol) and phenyl vinyl sulfone (2.7 g, 16 mmol) in acetonitrile (100 mL) was heated to reflux for 2.5 h and concentrated. The resulting residue was suspended in EtOAc (100 mL) and filtered. The solids obtained were washed with EtOAc (2×50 mL) and the pooled filtrates were concentrated. Chromatography (hexanes/EtOAc, 3:1) afforded (1SR, 5SR, 6RS)-6-(benzenesulfonyl)-8-(2-bromobenzyl)-3-(p-tolyl)-8-azabicyclo[3.2.1]oct-3-en-2-one (6.2 g, 74%) as a yellow solid: $R_f$ 0.4 (hexanes/EtOAc, 3:1); mp 155–159° C.; $^1$H NMR (CDCl$_3$) δ 2.10 (dd, 1H, J=9.3, 12.3 Hz), 2.37 (s, 3H), 2.87 (ddd, 1H, J=4.3, 7.6, 12.5 Hz), 3.71 (dd, 1H, J=4.3, 9.3 Hz), 3.79 (d, 1H, J=7.7 Hz), 3.99 (m, 2H), 4.40 (d, 1H, J=5.2 Hz), 6.99 (d, 1H, J=5.2 Hz), 7.12–7.37 (m, 7H), 7.54–7.59 (m, 3H), 7.67 (m, 1H), 7.89 (m, 2H). $^{13}$C NMR (CDCl$_3$) δ 21.2, 27.3, 51.0, 58.9, 67.4, 68.9, 123.8, 127.6, 128.1, 128.7, 128.8, 129.0, 129.3, 129.4, 130.4, 132.6, 133.9, 136.5, 138.2, 138.6, 139.6, 140.9, 196.6.

The above product (1.7 g, 3.3 mmol), AIBN (1.1 g, 6.5 mmol) and n-Bu$_3$SnH (6.9 mL, 26 mmol) in toluene (50 mL) was heated to reflux. After 20 h, the reaction mixture was cooled and the solvents were removed. Chromatography (hexanes/EtOAc, gradient, 4:1 to 0:1) followed by crystalization (hexanes/CH$_2$Cl$_2$) afforded Compound 44 (770 mg, 53%) as a white crystaline solid: mp 111–113° C.; $R_f$ 0.63 (hexanes/EtOAc, 1:1); $^1$H NMR (CDCl$_3$) δ 2.26 (s, 3H), 2.28 (dd, 1H, J=9.4, 14.6 Hz), 2.74 (ddd, 1H, J=6.5, 7.0, 14.6 Hz), 3.34 (dd, 1H, J=2.0, 7.0 Hz), 3.96 (d, 1H, J=7.0 Hz), 4.04 (d, 1H, J=7.0 Hz), 4.14–4.25 (m, 3H) , 4.40 (d, 1H, J=18 Hz), 5.94 (d, 1H, J=7.4 Hz), 6.36 (d, 2H, J=8.0 Hz), 6.80 (dd, J=7.4, 7.7 Hz), 6.89 (d, 2H, J=8.0 Hz), 7.04 (d, 1H, J=7.6 Hz), 7.18 (dd, 1H, J=7.6, 8.0 Hz), 7.58–7.73 (m, 3H), 8.0 (m, 2H); $^{13}$C NMR (CDCl$_3$) δ 21.1, 30.3, 48.5, 50.7, 53.9, 58.0, 65.9, 71.6, 125.1, 125.4, 127.7, 128.1, 128.9, 129.3, 130.3, 130.7, 131.2, 132.8, 133.4, 134.0, 136.8, 137.5, 108.5.

6.31 Synthesis of (1RS, 2SR, 4SR, 7RS)-10,11-Benzo-2-(p-tolyl)-8-azatricyclo [5.4.0.0⁴,⁸]undecane (Compound 45)

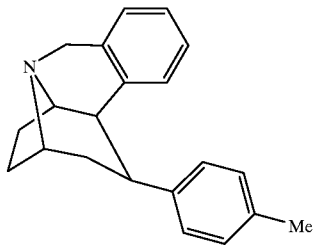

A 1.0M solution of DIBAL in hexanes (5.0 mL) was added dropwise to a solution of Compound 44 (750 mg, 1.7 mmol) in CH$_2$Cl$_2$ (25 mL) at −78° C. The resulting mixture was allowed to warm to rt over 3 h and carefully quenched with saturated NaHCO$_3$ (25 mL). The resulting mixture was filtered through a pad of Celite and the solids obtained were washed with CH$_2$Cl$_2$ (200 mL). The organic layers were separated and dried (Na$_2$SO$_4$). Chromatography (ether) afforded 6-(benzenesulfonyl)-10,11-benzo-2-(p-tolyl)-8-azatricyclo[5.4.0.0$^{4,8}$]undecan-3-ol (315 mg, 42%) as a white foam: R$_f$ 0.43 (ether); $^1$H NMR (CDCl$_3$) δ 1.59 (br s, 1H), 1.96 (dd, 1H, J=9.4, 14.4 Hz), 2.26 (s, 3H), 2.54 (ddd, 1H, J=6.1, 8.3, 14.4 Hz), 2.73 (s, 1H), 3.09 (s, 1H), 3.61 (m, 1H), 3.76 (d, 1H, J=6.1 Hz), 3.85 (dd, 1H, J=8.3, 9.4 Hz), 3.90 (s, 1H), 4.21 (d, 1H, J=8.1 Hz), 4.59 (d, 1H, J=8.1 Hz), 6.40 (d, 1H, J=7.7 Hz), 6.75 (d, 2H, J=7.5 Hz), 6.89 (dd, 1H, J=7.3, 7.7 Hz), 6.97 (d, 2H, J=7.5 Hz), 7.02 (d, 1H, J=7.3 Hz), 7.17 (t, 1H, J=7.4 Hz), 7.52–7.64 (m, 3H), 7.93 (m, 2H); $^{13}$C NMR (CDCl$_3$) δ 20.9, 29.9, 40.5, 43.3, 49.3, 58.2, 64.0, 65.8, 71.8, 124.0, 125.0, 126.7, 128.7, 128.8, 129.0, 130.0, 131.5, 133.6, 135.5, 135.8, 136.6, 137.4, 137.8.

The above products (300 mg, 0.67 mmol) and anhydrous Na$_2$HPO$_4$ (480 mg, 3.4 mmol) in MeOH (10 mL) was stirred at rt for 30 min. To this mixture was added 6% Na(Hg) (1.4 g, 3.4 mmol) and the resulting mixture was stirred for 3 h and carefully poured into 10% NH$_4$Cl (100 mL). The crude product was extracted with CH$_2$Cl$_2$ (3×100 mL) and chromatographed (EtOAc/Et$_3$N, 9:1) to afford (IRS, 2SR, 4RS, 6RS, 7SR)-10,11-benzo-2-(p-tolyl)-8-azatricyclo [5.4.0.0$^{4,8}$]undecan-3-ol (140 mg, 68%) as a white solid: mp=147–149° C.; R$_f$ 0.05 (EtOAc/Et$_3$N, 9:1); $^1$H NMR (CDCl$_3$) δ 1.60 (m, 1H), 1.97 (m, 1H), 2.17 (m, 1H), 2.30 (s, 3H), 2.70 (d, 1H, J=3.9 Hz), 3.35 (t, 1H, J=4.0 Hz), 3.49 (d, 1H, J=3.6 Hz), 3.66 (d, 1H, J=4.0 Hz), 3.72 (d, 1H, J=5.3 Hz), 4.46 (d, 1H, J=18 Hz), 4.81 (d, 1H, J=18 Hz), 6.49 (d, 1H, J=7.5 Hz), 6.85 (d, 2H, J=8.0 Hz), 6.91 (dd, 1H, J=7.1, 7.5 Hz), 7.01 (d, 2H, J=8.0 Hz), 7.09 (d, 1H, J=7.5 Hz), 7.18 (dd, 1H, J=7.1, 7.5 Hz); $^{13}$C NMR (CDCl$_3$) δ 20.9, 26.9, 27.0, 41.8, 42.4, 49.6, 56.8, 64.0, 73.5, 124.0, 125.1, 126.5, 128.6, 130.1, 131.4, 136.4, 136.9, 137.4, 137.8.

A 2.1 M solution of n-BuLi in hexanes (490 μL) was added dropwise to a solution of 10,11-benzo-2-(p-tolyl)-8-azatricyclo[5.4.0.0$^{4,8}$]undecan-3-ol (130 mg, 0.43 mmol) and i-Pr$_2$NH (100 μL, 0.53 mmol) in anhydrous THF (20 mL) at −78° C. After 5 min phenyl chlorothionoformate (150 μL, 1.1 mmol) was added dropwise and the resulting mixture was allowed to warm to rt for 3 h and carefully poured into sat. NaHCO$_3$ (50 mL). The crude product was extracted with EtOAc (3×25 mL). The combined extracts were washed with satd. NaHCO$_3$ (50 mL) and brine (50 mL). Chromatography (EtOAc) afforded (1RS, 2SR, 4RS, 6RS, 7SR)-10, 11-benzo-2-(p-tolyl)-8-azatricyclo[5.4.0.0$^{4,8}$]undecan-3-yl phenyl thionocarbonate (28 mg, 15%) as a colorless oil: R$_f$ 0.28 (EtOAc); $^1$H NMR (CDCl$_3$) δ 1.81 (m, 1H), 2.05 (m, 1H), 2.27 (m, 2H), 2.32 (s, 3H), 2.69 (dd, 1H, J=2.5, 4.1 Hz), 3.61 (m, 2H), 3.99 (dd, 1H, J=1.9, 7.2 Hz), 4.55 (s, 2H), 5.36 (dd, 1H, J=1.9, 3.5 Hz), 6.37 (d, 1H, J=7.5 Hz), 6.72 (d, 2H, J=8.0 Hz), 6.92–7.05 (m, 5H), 7.14–7.24 (m, 3H), 7.33 (m, 2H); $^{13}$C NMR (CDCl$_3$) δ 21.0, 26.8, 27.0, 42.2, 49.7, 56.7, 60.8, 84.2, 122.0, 123.9, 125.1, 126.4, 126.8, 128.3, 129.4, 130.6, 131.5, 135.3, 136.0, 136.5, 137.5, 153.3, 194.3.

A solution of (1RS, 2SR, 4RS, 6RS, 7SR)-10,11-benzo-2-(p-tolyl)-8-azatricyclo[5.4.0.0$^{4,8}$]undecan-3-yl phenyl thionocarbonate (26 mg, 0.062 mmol), AIBN (10 mg, 0.062 mmol) and n-Bu$_3$SnH (82 μL, 0.31 mmol) in toluene (5 mL) was heated to reflux for 2 h and then concentrated. The crude residue obtained was subjected to PTLC (hexanes/EtOAc/Et$_3$N, 5:4:1) to Compound 45 (14 mg, 75%) as a white solid: R$_f$ 0.15 (hexanes/EtOAc/Et$_3$N, 5:4:1); $^1$H NMR (CDCl$_3$) δ 1.31 (m, 1H), 1.75–2.23 (m, 4H), 2.28 (s, 3H), 3.45–3.51 (m, 2H), 3.62 (m, 1H), 4.24 (m, 1H), 4.45 (m, 1H), 5.97 (m, 1H), 6.60 (d, 2H, J=8.0 Hz), 6.76 (m, 1H), 6.95 (d, 2H, J=8.0 Hz), 7.10 (m, 2H). p-Toluenesulfonate salt: $^1$H NMR (CDCl$_3$) δ 1.65 (m, 1H), 2.03–2.16 (m, 2H), 2.29 (s, 3H), 2.32 (m, 1H), 2.37 (s, 3H), 2.70 (m, 2H), 3.09 (m, 1H), 3.51 (m, 1H), 4.10 (m, 1H), 4.31 (m, 1H), 4.57 (d, 1H, J=7.9 Hz), 4.94 (dd, 1H, J=6.2, 8.0 Hz, ), 6.05 (d, 1H, J=7.7 Hz), 6.56 (d, 2H, J=7.9 Hz), 6.87 (t, 1H, J=7.3 Hz), 6.98 (d, 2H, J=7.9 Hz), 7.16–7.23 (m, 5H), 7.81 (d, 1H, J=8.1 Hz). $^{13}$C NMR (CDCl$_3$) δ 21.0, 21.3, 25.2, 25.7, 26.4, 37.7, 43.9, 46.7, 58.0, 62.7, 125.0, 126.5, 127.7, 127.9, 128.4, 128.8, 130.8, 131.2, 136.1, 136.9, 140.1, 142.0. Anal. [C$_{21}$H$_{23}$N.1.2C$_7$H$_8$O$_3$S] calcd: C 69.79, H 6.50, N 2.77; found: C 69.72, H 6.36, N 2.70.

6.32 Synthesis of (1RS, 5RS, 7SR)-4-Acetoxy-3-(4-tolyl)-10-azatricyclo [5.3.0.0$^{5,10}$]dec-2-ene (Compound 46)

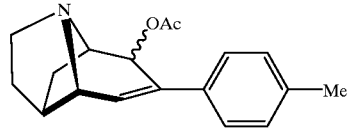

Compound 46 was synthesized as reported in Smith et al., 1998, Tetrahedron Let. 39:197–200.

6.33 Synthesis of (4SR, 5RS, 7SR)-4-Ethyl-3-(4-tolyl)-10-azatricyclo [5.3.0.0$^{5,10}$]dec-2-ene (Compound 47b)

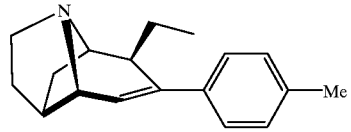

A 1.0M solution of ethylmagnesium bromide in THF (6 mL) was added dropwise to a solution of Compound 46 (560 mg, 2 mmol) and CuCN (56 mg) in anhydrous ether (20 mL) at −20° C. The resulting mixture was stirred at this temperature for 30 min and then allowed to warm to rt for 3 h. The reaction was quenched with 10 NH$_4$OH (20 mL) and extracted with CH$_2$Cl$_2$ (3×50 mL). The organic extracts were washed with water (50 mL), brine (50 mL) and dried (Na$_2$SO$_4$). Chromatography (Et$_2$O/Et$_3$N, 9:1) afforded Compound 47b (38 mg, 27%) as a clear colorless oil: R$_f$ 0.79 (Et$_2$O/Et$_3$N, 9:1); $^1$H NMR (CDCl$_3$) δ 0.94 (t, 3H, J=8.0 Hz), 1.21–1.36 (m, 2H), 1.43–1.52 (m, 2H), 1.60–1.69 (m, 2H), 2.18 (m, 1H), 2.32 (s, 3H), 2.40 (m, 1H), 2.57 (m, 1H), 3.04–3.16 (m, 3H), 5.92 (d, 1H, J=5.7 Hz), 7.10 (d, 2H, J=8.1 Hz), 7.21 (d, 2H, J=8.1 Hz); $^{13}$C NMR (CDCl$_3$) δ 12.6, 20.9, 24.8, 31.9, 34.3, 44.7, 49.4, 52.3, 62.1, 65.7, 122.6, 125.7, 35 128.9, 136.5, 137.4, 139.3.

6.34 Synthesis of (1RS, 3RS, 4SR, 7SR)-4-Ethyl-3-(4-tolyl)-10-azatricyclo [5.3.0.0$^{5,10}$]decane (Compound 42b)

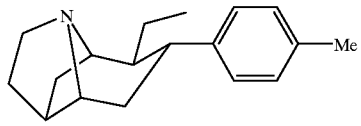

A suspension of Compound 47b (130 mg, 0.52 mmol), p-toluenesulfonic acid monohydrate (200 mg, 1.0 mmol) and a catalytic amount of 10% Pd/C in EtOAc (15 mL) was shaken under H$_2$ (50 psi) for 3 h, degassed and filtered through Celite. The solids obtained were washed with EtOH (2×10 mL) and the combined filtrates were diluted with satd. NaHCO$_3$ (50 mL) and extracted with EtOAc (2×50 mL). The organic extracts were dried (Na$_2$SO$_4$) and concentrated. PTLC (hexanes/EtOAc/Et$_3$N, 5:4:1) afforded Compound 42b (53 mg, 41%) as a clear colorless oil: $^1$H NMR (CDCl$_3$) δ 0.80 (t, 3H, J=7.8 Hz), 1.11–1.59 (m, 8H), 2.02 (m, 1H), 2.25 (m, 1H), 2.30 (s, 3H), 2.43 (m, 1H), 2.61 (m, 1H), 2.79 (m, 1H), 2.98 (m, 2H), 7.08 (s, 4H); p-Toluenesulfonate salt: $^1$H NMR (CDCl$_3$) δ 0.77 (t, 3H, J=7.8 Hz), 1.38 (m, 1H), 1.54–1.72 (m, 4H), 2.05 (m, 1H), 2.11 (m, 2H), 2.24 (m, 1H), 2.31 (s, 3H), 2.37 (s, 3H), 2.64 (s, 1H), 2.87 (m, 1H), 3.09 (m, 1H), 3.52 (t, 1H, J=5.1 Hz), 3.87 (m, 1H), 3.96 (d, 1H, J=9.5 Hz), 6.95 (d, 2H, J=7.8 Hz), 7.07 (d, 2H, J=7.8 Hz), 7.24 (d, 2H, J=8.0 Hz), 7.85 (d, 2H, J=8.0 Hz). $^{13}$C NMR (CDCl$_3$) δ 11.9, 20.9, 21.3, 25.0, 27.9, 30.0, 35.9, 39.2, 40.4, 50.8, 52.3, 63.6, 65.9, 125.0, 127.7, 128.7, 129.2, 136.5, 139.4, 139.8, 142.7. Anal. [C$_{18}$H$_{25}$N.1.05C$_7$H$_8$O$_3$S] calcd: C 69.50, H 7.68, N 3.17; found: C 69.25, H 7.64, N 3.02.

6.35 Synthesis of (1RS, 2SR, 3SR, 5SR, 7SR)-2-Butyl-3-(4-methylphenyl)-10-azatricyclo [5.3.0.0$^{3,8}$]decane (Compound 49a) and (1RS, 2SR, 3RS, 5SR, 7SR)-2-Butyl-3-(4-methylphenyl)-10-azatricyclo [5.3.0.0$^{3,8}$] decane (Compound 50a)

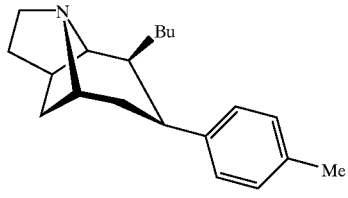
49a

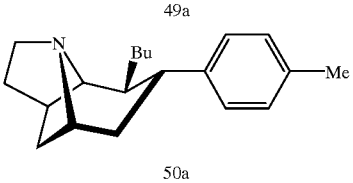
50a

A suspension of Compound 48a (630 mg, 2.2 mmol), p-toluenesulfonic acid monohydrate (850 mg, 4.4 mmol) and a catalytic amount of 10% Pd/C in EtOAc (25 mL) was shaken under H$_2$ (50 psi) for 3 h, degassed and filtered through Celite. The solids obtained were washed with EtOH (2×10 mL) and the combined filtrates were diluted with NaHCO$_3$ (50 mL) and extracted with EtOAc (2×50 mL). The organic extracts were dried (Na$_2$SO$_4$) and concentrated. Chromatography (hexanes/EtOAc/Et$_3$N, 5:4:1) afforded, as the first product to elute, Compound 49a (160 mg, 26%) as a clear colorless oil. $^1$H NMR (CDCl$_3$) δ 0.72 (t, 3H,J=7.8 Hz), 0.90–1.02 (m, 3H), 1.10–1.25 (m, 3H), 1.44–1.52 (m, 3H), 2.24–2.47 (m, 2H), 2.31 (s, 3H), 2.72 (s, 1H), 2.95 (m, 1H), 3.17–3.22 (m, 2H), 7.07 (s, 4H) . p-Toluenesulfonate salt: $^1$H NMR (CDCl$_3$) δ 0.77 (t, 3H, J=7.9 Hz), 0.97–1.13 (m, 2H), 1.24 (m, 1H), 1.48–1.72 (m, 6H), 1.93–2.08 (m, 2H), 2.24 (m, 1H), 2.35 (s, 3H), 2.38 (s, 3H), 2.76 (t, 1H, J=8.0 Hz), 2.87 (s, 1H), 3.18 (m, 1H), 3.42 (s, 1H), 3.79 (m, 1H), 4.08 (m, 1H), 6.97 (d, 2H, J=7.8 Hz), 7.10 (d, 2H, J=7.8 Hz), 7.19 (d, 2H, J=8.0 Hz), 7.82 (d, 2H, J=8.0 Hz). $^{13}$C NMR (CDCl$_3$) δ 13.8, 21.0, 21.3, 22.1, 26.6, 29.2, 29.4, 30.1, 31.1, 34.4, 38.8, 39.2, 51.2, 63.3, 70.3, 77.2, 126.1, 127.7. 128.7, 129.2, 136.5, 136.6, 139.7, 142.7. Anal. [C$_{20}$H$_{29}$N.1.15C$_7$H$_8$O$_3$S] calcd: C 69.13, H 7.86, N 2.97; found: C 69.34, H 8.06, N 2.81.

Further elution provided Compound 49a (330 mg, 54%) as a clear colorless oil. $^1$H NMR (CDCl$_3$) δ 0.81 (t, 3H, J=6.6 Hz), 1.10–1.28 (m, 8H), 1.47–1.62 (m, 4H), 2.28 (m, 1H), 2.34 (s, 3H), 2.43–2.53 (m, 2H), 2.67 (s, 1H), 2.76 (m, 1H), 2.91–3.01 (m, 2H), 7.08 (m, 4H). p-Toluenesulfonate salt: $^1$H NMR (CDCl$_3$) δ 0.77 (t, 3H, J=7.2 Hz), 1.02–1.28 (m, 6H), 1.46 (dd, 1H, J=9.1, 13.7 Hz), 1.71 (m, 1H), 1.81 (m, 1H), 2.04–2.27 (m, 4H), 2.33 (s, 3H), 2.38 (s, 3H), 2.64 (s, 1H), 2.74 (m, 1H), 3.02 (m, 1H), 3.19 (m, 1H), 3.51 (s, 1H), 3.77 (m, 2H), 6.94 (d, 2H, J=7.8 Hz), 7.09 (d, 2H, J=7.8 Hz), 7.20 (d, 2H, J=8.1 Hz), 7.85 (d, 2H, J=8.1 Hz) $^{13}$C NMR (CDCl$_3$) δ 13.8, 20.9, 21.3, 27.7, 28.5, 32.8, 36.3, 39.2, 39.3, 39.7, 39.8, 50.5, 60.0, 71.3, 125.9, 127.7, 128.7, 129.3, 136.3, 139.3, 139.7, 142.7. Anal. [C$_{20}$H$_{29}$N.1.05C$_7$H$_8$O$_3$S] calcd: C 70.49, H 8.08, N 2.99; found: C 70.18, H 8.09, N 2.86.

Other Compounds

Other compounds of the invention can be readily synthesized by routine modification of the synthetic pathways described herein or in the literature. Exemplary methods include those described in WO 97/16451; Smith et al., 1998, Tetrahedron Lett. 39:197–200; Prakash et. al., 1998, Med. Chem. Res. 8(1/2):43–58; Keverline-Frantz et. al., 1998, J. Med. Chem., 41:247–257; Davies et al. 1996, J. Med. Chem., 39:2554–2558 and Orlek et. al., 1991, J. Med. Chem., 34:2726–2735, as well as the references cited in all of the above.

EXAMPLE: X-RAY CRYSTALLOGRAPHY INDICATES THE STEREOCHEMISTRY OF THE NITROGEN LONE PAIR INFLUENCES SELECTIVITY

Experimental Protocol

Compounds (−)-40 and 50a were synthesized and crystallized as described in Examples 6.28 and 6.35, respectively. Compound 42a was prepared and crystallized as described in Smith et al., supra, and their structures determined by X-ray crystallography. The X-ray crystal structure of Compound (−)-40 is provided in FIG. 1, the crystal structure of Compound 42a is provided in FIG. 2 and the x-ray crystal structure of Compound 50a is provided in FIG. 3.

Results

Figure 2:
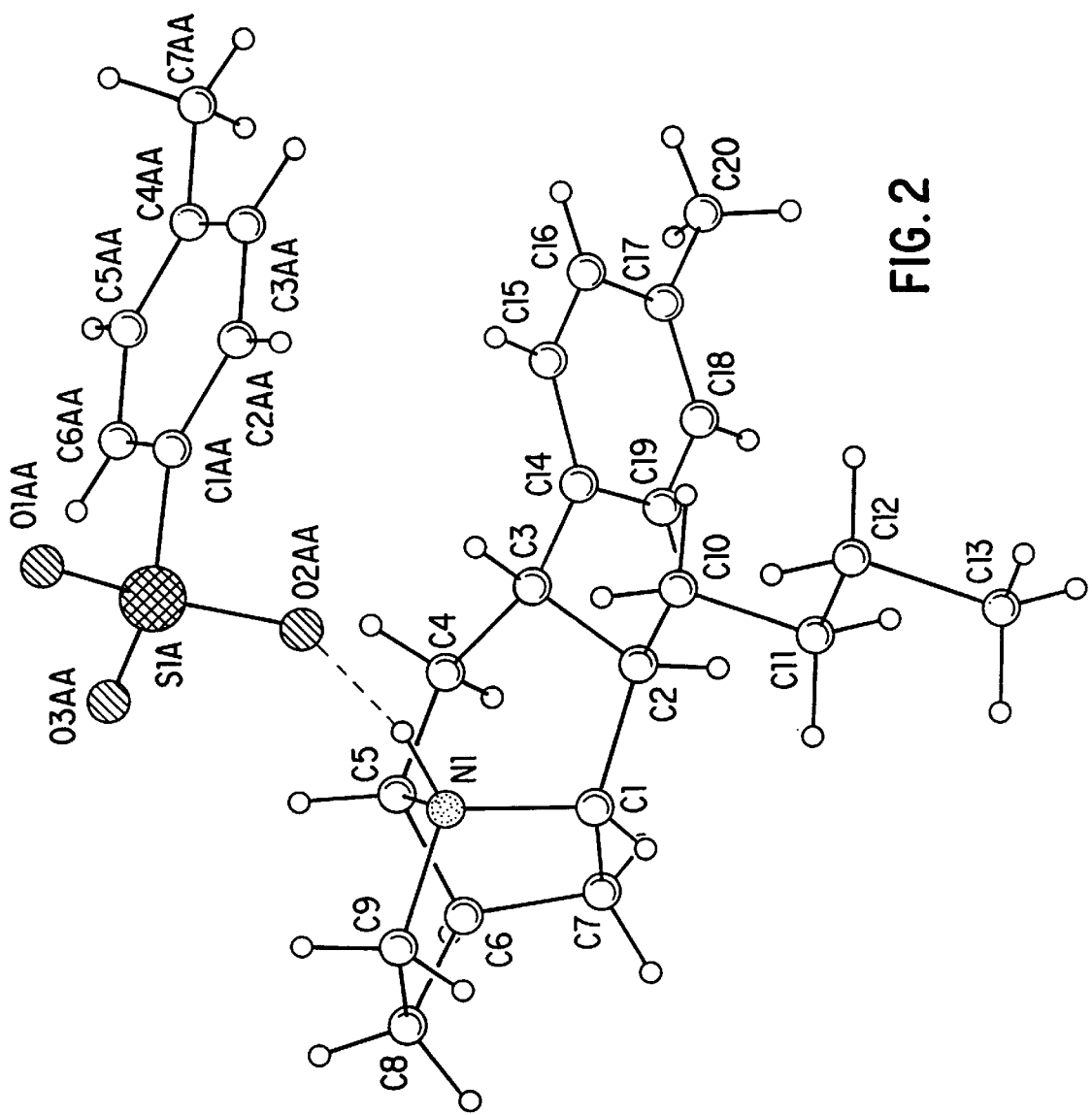
FIG. 2 shows the structure of (1SR, 3SR, 4RS, 5SR, 7RS)-4-butyl-3-(4-methylphenyl)-10-azatricyclo[$5.3.0.0^{3,8}$] decane (Compound 42a), as determine by x-ray crystallography.
Figure 3:
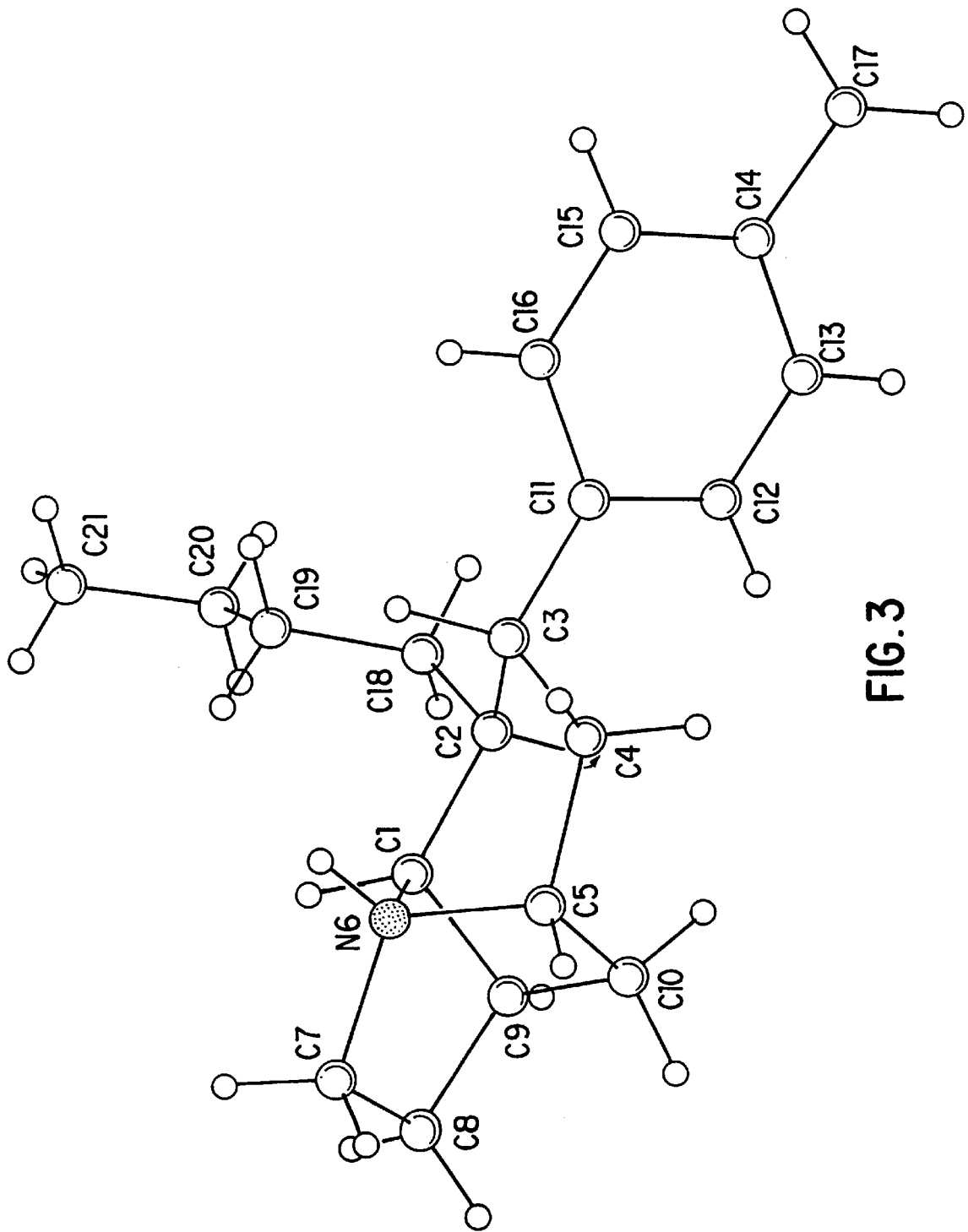
FIG. 3 shows the structure of (1SR, 2SR, 3RS, 5RS, 7SR)-2-butyl-methylphenyl)-10-azatricyclo [$5.3.0.0^{5,10}$] decane (Compound 50a), as determine by x-ray crystallography.

Referring to FIGS. 1, 2 and 3, an examination of the crystal structures of compounds (−)-40, 42a and 50a shows a striking good overlap of the C(1), N(8), C(5) (using the numbering system of cocaine) and the centroid of the phenyl substituent with a nitrogen to centroid distance of 5.55–5.62 Å. This is in close agreement with the value of 5.64 Å for the recently reported 2β-carbomethyoxy-3α-(3,4-dichlorophenyl) tropane (Meltzer et al., 1997, 40:2661–2673). These data strongly suggest that the differences found in the binding are due to the stereochemistry of the nitrogen lone pair, rather than the slight changes in conformation of the tropane skeleton arising from the introduction of the tether.

EXAMPLE: Biological Activity

This example demonstrates the re-uptake inhibition of the compounds of the invention, and the selectivity for the serotonin and dopamine transporters of the front-bridged and back-bridged compounds of the invention respectively.

Experimental Protocol

Various isomeric forms of front-bridged Compounds 4, 5, 29, 30, 31, 40 and 50a and back-bridged Compounds 41, 42a, 42b, 49a and 50a were assayed for binding at the dopamine transporter and for inhibition of monamine re-uptake at the dopamine, serotonin and norepinephrine transporters. Mazindol binding were measured as previously described in Johnson et. al., 1992, Eur. J. Pharmacol., Mol. Pharmacol. Sect., 227:411–415. Reuptake inhibition was measured essentially as described in Yi et. al., 1991, Neuropharmacol. 29:475–486, except that an identical Krebs-Ringer-HEPES buffer was used for binding and all uptake assays (Slusher et al., 1997, Drug Alcohol Depend. 48:43–50).

Results

The results of the biological assays are shown in TABLE 1, infra:

All of the compounds tested showed high binding affinity at the dopamine transporter with about 2.5- to 104-fold greater potency than cocaine. In the inhibition of monoamine reuptake, these rigid cocaine analogs are generally more potent than cocaine. This increased potency is most evident at the DAT, where the rigid analogs are 2.8- to 190-fold more active than cocaine. A somewhat smaller spread in activities was noted at the NET with up to a 78-fold increase in activity. The SAR of the activity at the 5-HT transporter is much more complicated. The most active compound (+)-40 is about 100-fold more active while 29β and 29α are 52- and 25-fold less active than cocaine, respectively.

A comparison of the ratio of the reuptake inhibition at the 5-HTT and at the DAT for the rigidified analogs reveals a dramatic difference between the 7-unsubstituted front-bridged (40 and 45) and back-bridged structures (41a, 42a, 42b, 49a and 50a), with the former exhibiting up to 77-fold greater activity at the 5-HTT while the latter show up to 44-fold higher activity at the DAT. While the front-bridged analogs showed up to 25-fold selectivity for the NET over the DAT, the back-bridged analogs did not show such a dramatic reversal in NET/DAT selectivity as seen for the 5-HTT/DAT selectivity.

Based on x-ray crystallography data, the noted selectivity is presumed to be the result of the stereochemistry of the nitrogen lone pair, with the front-bridged analogs exhibiting a strong preference for the serotonin transporter and the back-bridged analogs exhibiting a slightly lesser preference for the dopamine receptor. Interestingly, the NET was significantly less influenced by the orientation of the nitrogen lone pair.

Based on previous reports, it is quite surprising that the back-bridged analogs exhibit affinity for the DAT. All tropane analogs with substituents on the 2-carbon bridge reported previously exhibit substantially reduced activity at the DAT, presumably due to adverse steric interactions in this region. Thus, the stereochemical preference of the DAT for an orientation of the lone-pair over the 3-carbon bridge is likely to be underestimated by using the data for the back-bridged compounds of the present studies. This steric argument is further apparent in the 7-substituted front

TABLE 1

ACTIVITY AT MONOAMINE TRANSPORTERS; $K_i \pm SE$ (nM)

| Compound | [$^3$H]Mazindol Binding | [$^3$H]DA Uptake | [$^3$H]5-HT Uptake | [$^3$H]NE Uptake | 5-HT/DA |
|---|---|---|---|---|---|
| cocaine | 375 ± 68.18 | 422.7 ± 146.5 | 154.7 ± 0.40 | 83.3 ± 1.5 | 0.37 |
| (−)-40 | 54.3 ± 10.2 | 60.3 ± 0.4 | 1.76 ± 23 | 5.24 ± 0.07 | 0.029 |
| (+)-40 | 79 ± 19 | 113.6 ± 28.17 | 1.48 ± 0.07 | 4.62 ± 0.31 | 0.013 |
| (±)-40 | 61.7 ± 8.5 | 60.27 ± 0.43 | 2.32 ± 0.23 | 2.69 ± 0.12 | 0.038 |
| 29β | 620 ± 0.03 | 1420 ± 140 | 8030 ± 510 |  | 5.65 |
| 30β | 186.1 ± 37.9 | 491.7 ± 44.2 | 97.73 ± 18.94 |  | 0.20 |
| 31β | 46.97 ± 2.32 | 211.4 ± 6.91 | 28.54 ± 1.32 |  | 0.14 |
| 29α | 4140 ± 600 | 20100 ± 1560 | 3920 ± 3200 |  | 4.9 |
| 30α | 3960 ± 580 | 8850 ± 370 | 695.7 ± 3.2 | 1150 ± 30 | 0.08 |
| 45 | 6.86 ± 0.43 | 23.95 ± 1.33 | 1.77 ± 0.04 | 1.06 ± 0.03 | 0.074 |
| 42a | 4.00 ± 0.07 | 2.23 ± 0.12 | 13.98 ± 0.58 | 2.99 ± 0.17 | 6.3 |
| 41a | 17.15 ± 1.13 | 10.15 ± 1.43 | 78.85 ± 0.87 | 15.0 ± 0.4 | 7.77 |
| 42b | 3.61 ± 0.43 | 11.33 ± 1.09 | 25.73 ± 4.27 | 4.43 ± 0.01 | 2.3 |
| 50a | 148.8 ± 5.75 | 148.8 ± 2.13 | 810.2 ± 79.5 | 51.7 ± 12 | 5.4 |
| 49a | 13.67 ± 0.79 | 14.18 ± 0.02 | 618.1 ± 86.9 | 3.84 ± 0.35 | 44 |
| (−)-4 | 10500 ± 930 | 16500 ± 970 | 1890 ± 440 | 70900 ± 18000 | 0.11 |
| (+)-4 | 18500 ± 2700 | 27600 ± 1000 | 4630 ± 760 | 38300 ± 4610 | 0.16 |
| (−)-5 | 9740 ± 160 | 9050 ± 460 | 11900 ± 610 | 4650 ± 440 | 1.3 |
| (+)-5 | 6770 ± 500 | 10500 ± 450 | 25100 ± 3600 | 4530 ± 410 | 2.4 | bridged compounds (29, 30 and 31). While the introduction of a substituent at the 7-position results in decreased reuptake potency at both transporters, except in the case of the more bulky ethyl ester substituent, the selectivity for the 5-HTT is retained. Additionally in this 7-substituted series a discrepancy between the binding affinity and the reuptake potency in noted. In particular the 7β-methyl compound 31β is 4.5-fold more active in binding than reuptake inhibition, suggesting partial agonist activity. In contrast to the cocaine series, the binding potencies of (±)-40 and (+)-40 are only slightly decreased from that of the (−)-40 (cocaine-like) enantiomer. This has recently been noted for other cocaine analogs. (Lomenzo et al., 1997, J. Med. Chem. 40:4406–4414).

The bicyclic compounds tested show reduced potency compared with both the tricyclic analogs and cocaine. The introduction of additional substituents, that are known to increase activity in the cocaine and WIN series, will provide analogs in this series with increased potency. The influence of the direction of the nitrogen lone pair is still readily apparent in the bicyclic compounds. A comparison of the crystal structures for the cis compound (−)-4 and trans (+)-5 with those of (−)- 40, 42a, and 50a demonstrates that the nitrogen lone pair in (−)-4 is fixed in the same direction as that in the front-bridged series, and show the expected 6.4 to 8.8-fold selectivity for the 5-HTT over the DAT. Conversely for the trans isomers (−)-5 and (+)-5 the nitrogen lone pair is directed in space in a manner similar to that for the back-bridged tricyclic series, and exhibit a 1.3 and 2.4-fold selectivity for the DAT. Cis- Compounds (−)-4 and (+)-4 also exhibit dramatically improved 5-HTT/NET selectivity being 38- and 8.8 fold more active at the 5-HTT.

EXAMPLE: Formulations

The following examples provide exemplary, not limiting, formulations for administering the compounds of the invention to mammalian, especially human, patients. Any of the compounds described herein, or pharmaceutical salts or hydrates thereof, may be formulated as provided in the following examples.

Tablet Formulation

Tablets each containing 60 mg of active ingredient are made up as follows:

| | |
|---|---|
| Active Compound | 60 mg |
| Starch | 45 mg |
| Microcrystalline Cellulose | 45 mg |
| Sodium carboxymethyl starch | 4.5 mg |
| Talc | 1 mg |
| Polyvinylpyrrolidone (10% in water) | 4 mg |
| Magnesium Stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50–60° C. and passed through a No. 18 mesh U.S. sieve. The sodium carboxymethyl starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed by wet granulation followed by compression.

Gelatin Capsules

Hard gelatin capsules are prepared using the following ingredients:

| | |
|---|---|
| Active Compound | 250 mg/capsule |
| Starch dried | 200 mg/capsule |
| Magnesium Stearate | 10 mg/capsule |

The above ingredients are mixed and filled into hard gelatin capsules in 460 mg quantities.

Aerosol Solution

An aerosol solution is prepared containing the following components:

| | |
|---|---|
| Active Compound | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Suppositories

Suppositories each containing 225 mg of active ingredient are made as follows:

| | |
|---|---|
| Active Compound | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Suspensions

Suspensions each containing 50 mg of medicament per 5 mL dose are made as follows:

| | |
|---|---|
| Active Compound | 50 mg |
| Sodium carboxymethylcellulose | 50 mg |
| Syrup | 1.25 mL |

-continued

| | |
|---|---|
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

All cited references are hereby incorporated in their entireties by reference herein.

What is claimed is:

1. A compound, or a pharmaceutically acceptable salt thereof, having the structure:

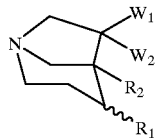

wherein:

$W_1$ and $W_2$ taken together form =O, =S, =NOR$_3$, =N—CN, =N—NR$_3$R$_4$, =CR$_3$R$_4$ or (C$_3$–C$_8$) alkeno, or $W_1$ and $W_2$ are each independently selected from the group consisting of —H, halogen, —OR$_3$, —SR$_3$, —N—NR$_3$R$_4$ or —(CH$_2$)$_o$—O—(CH$_2$)$_o$-R$_7$ where each o is independently 0, 1, 2 or 3;

$R_1$ is phenyl or phenyl independently substituted with one or more $R_6$;

$R_2$ is —H, (C$_2$–C$_6$) alkyl, (C$_2$–C$_6$) alkenyl, (C$_2$–C$_6$) alkynyl, (C$_5$–C$_{20}$) aryl, 5–20 membered heteroaryl or —(CH$_2$)$_q$—O—(CH$_2$)$_q$—R$_7$ where each q is independently 0, 1, 2 or 3;

$R_3$ and $R_4$ are each independently selected from the group consisting of —H, (C$_1$–C$_6$) alkyl, (C$_2$–C$_6$) alkenyl, (C$_2$–C$_6$) alkynyl, (C$_5$–C$_{20}$) aryl, (C$_5$–C$_{20}$) aryl independently substituted with one or more $R_6$, 6–26 membered heteroaryl and 6–26 membered heteroaryl independently substituted with one or more $R_6$;

each $R_6$ is independently selected from the group consisting of halogen, —CF$_3$, —CN, (C$_1$–C$_6$) alkyl, (C$_2$–C$_6$) alkenyl, (C$_2$–C$_6$) alkynyl, (C$_1$–C$_6$) alkoxy and (C$_3$–C$_6$) cycloalkoxy; and $R_7$ is (C$_5$–C$_{20}$) aryl, (C$_5$–C$_{20}$) aryl independently substituted with one or more $R_6$, 5–20 membered heteroaryl and 5–20 membered heteroaryl independently substituted with one or more $R_6$.

2. The compound or salt of claim 1 which is a (±) racemic mixture.

3. The compound or salt of claim 1 which is the (+) optical isomer.

4. The compound or salt of claim 1 which is the (−) optical isomer.

5. The compound or salt of claim 1 in which $R_1$ is phenyl or phenyl independently substituted with one or more halogen, (C$_1$–C$_6$) alkyl, (C$_2$–C$_6$) alkenyl, (C$_2$–C$_6$) alkynyl or (C$_1$–C$_6$) alkoxy groups.

6. The compound or salt of claim 5 in which the phenyl is mono-substituted at the para position or disubstituted at the ortho and para positions.

7. The compound or salt of claim 5 in which $R_1$ is phenyl, methylphenyl, chlorophenyl, fluorophenyl, iodophenyl, methoxyphenyl, dichlorophenyl, dimethoxyphenyl or ethyl-iodophenyl.

8. The compound or salt of claim 1 which has the structure:

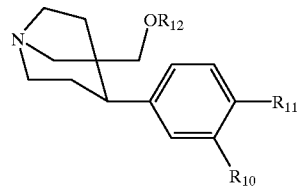

wherein:

$R_{10}$ is halogen, —F, —Cl, —Br, —I, methyl, (C$_1$–C$_6$) alkyl, (C$_2$–C$_6$) alkenyl or (C$_2$–C$_6$) alkynyl;

$R_{11}$ is halogen, —F, —Cl, —Br, —I, methyl, (C$_1$–C$_6$) alkyl, (C$_2$–C$_6$) alkenyl or (C$_2$–C$_6$) alkynyl;

$R_{12}$ is benzodioxolyl, 1,3-benzodioxol-5-yl, (trihalomethyl)phenyl, 4-(trihalomethyl)phenyl, (trifluoromethyl)phenyl, 4-(trifluoromethyl)phenyl, halophenyl, 4-halophenyl, fluorophenyl and 4-fluorophenyl.

9. The compound or salt of claim 1 which has the structure:

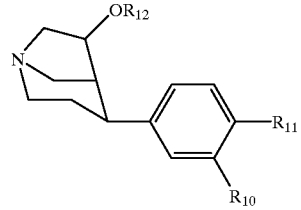

wherein:

$R_{10}$ is halogen, —F, —Cl, —Br, —I, methyl, (C$_1$–C$_6$) alkyl, (C$_2$–C$_6$) alkenyl or (C$_2$–C$_6$) alkynyl;

$R_{11}$ is halogen, —F, —Cl, —Br, —I, methyl, (C$_1$–C$_6$) alkyl, (C$_2$–C$_6$) alkenyl or (C$_2$–C$_6$) alkynyl;

$R_{12}$ is benzodioxolyl, 1,3-benzodioxol-5-yl, (trihalomethyl)phenyl, 4-(trihalomethyl)phenyl, (trifluoromethyl)phenyl, 4-(trifluoromethyl)phenyl, halophenyl, 4-halophenyl, fluorophenyl and 4-fluorophenyl.

10. A pharmaceutical composition comprising a compound or salt according to anyone of claims 1–4, or 5–9 and a pharmaceutically acceptable carrier, excipient, or diluent.

11. The compound of claim 1 in which:

$R_1$ is phenyl independently substituted with one or more halogen, (C$_1$–C$_6$) alkyl, (C$_2$–C$_6$) alkenyl, (C$_2$–C$_6$) alkynyl or (C$_1$–C$_6$) alkoxy;

$R_2$ is —$(CH_2)_q$—O—$(CH_2)_q$—$R_7$ where each q is independently 0, 1, 2 or 3; and $W_1$ and $W_2$ are each —H.

12. The compound of claim 11 in which the phenyl is mono-substituted.

13. The compound of claim 11 in which the phenyl is di-substituted.

14. The compound of claim 11 in which the ($C_1$–$C_6$) alkyl is methyl.

15. The compound of claim 11 in which the halogen is selected from the group consisting of fluoro, chloro and bromo.

16. The compound of claim 11 in which the ($C_2$–$C_6$) alkenyl is isopropenyl.

17. The compound of claim 1 in which:

$R_1$ is phenyl independently substituted with one or more halogen, ($C_1$–$C_6$) alkyl, ($C_2$–$C_6$) alkenyl, ($C_2$–$C_6$) alkynyl or ($C_1$–$C_6$) alkoxy;

$R_2$ is —$(CH_2)_q$—O—$(CH_2)_q$—$R_7$ where each q is independently 0, 1, 2 or 3; and $W_1$ and $W_2$ taken together are =$CH_2$.

18. The compound of claim 17 in which the phenyl is mono-substituted.

19. The compound of claim 17 in which the phenyl is di-substituted.

20. The compound of claim 17 in which the ($C_1$–$C_6$) alkyl is methyl.

21. The compound of claim 17 in which the halogen is selected from the group consisting of fluoro, chloro and bromo.

22. The compound of claim 17 in which the ($C_2$–$C_6$) alkenyl is isopropenyl.

23. The compound of claim 1 which has the structure:

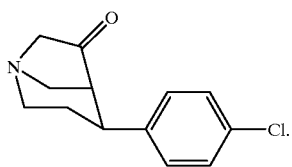

4

24. The compound of claim 23 which is the (−) isomer.
25. The compound of claim 23 which is the (+) isomer.

26. The compound of claim 1 which has the structure:

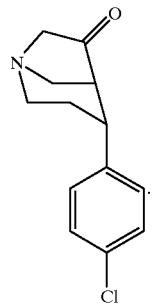

5

27. The compound of claim 25 which is the (−) isomer.
28. The compound of claim 26 which is the (+) isomer.
29. The compound of claim 1 which has the structure:

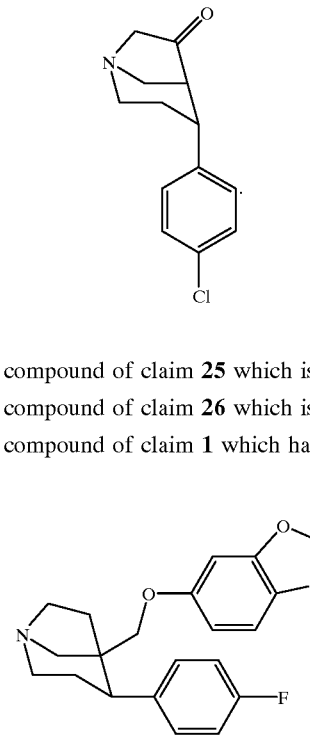

7

30. The compound of claim 1 which has the structure:

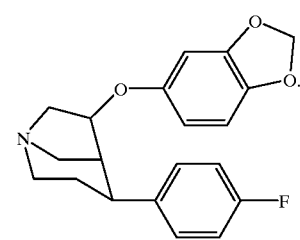

51

* * * * *

UNITED STATES PATENT AND TRADEMARK OFFICE
CERTIFICATE OF CORRECTION

PATENT NO. : 6,150,376

DATED : November 21, 2000

INVENTOR(S) : Kozikowski et al.

It is certified that errors appear in the above-identified patent and that said Letters Patent is hereby corrected as shown below:

In the title [54], insert --Novel-- before "Bi-";
Column 63, line 46 after "--H", replace "$(C_2-C_6)$" with --$(C_1-C_6)$--;
Column 64, line 46 after "1-4", delete "or"; and
Column 64, line 46 after "5-9", insert --or 11-30--

Signed and Sealed this

Eighth Day of May, 2001

Attest:

NICHOLAS P. GODICI

Attesting Officer     Acting Director of the United States Patent and Trademark Office